(12) United States Patent
Horvitz et al.

(10) Patent No.: US 7,138,510 B1
(45) Date of Patent: Nov. 21, 2006

(54) CLONING SEQUENCING AND CHARACTERIZATION OF TWO CELL DEATH GENES AND USES THEREFOR

(75) Inventors: H. Robert Horvitz, Cambridge, MA (US); Junying Yuan, Newton, MA (US); Shai Shaham, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 679 days.

(21) Appl. No.: 08/984,178

(22) Filed: Dec. 3, 1997

Related U.S. Application Data

(63) Continuation of application No. 08/287,669, filed on Aug. 9, 1994, now abandoned, and a division of application No. 07/979,638, filed on Nov. 20, 1992, now abandoned, which is a continuation-in-part of application No. 07/897,788, filed on Jun. 12, 1992, now abandoned.

(51) Int. Cl.
*C07H 21/02* (2006.01)

(52) U.S. Cl. .................................. 536/23.5; 536/23.1
(58) Field of Classification Search .............. 536/23.1, 536/24.31, 24.33, 24.3; 800/8, 3; 435/91.1, 435/455
See application file for complete search history.

(56) References Cited

U.S. PATENT DOCUMENTS

| 4,855,319 A | 8/1989 | Mikolajczak et al. ....... 514/473 |
| 5,196,333 A | 3/1993 | Chalfie et al. ........... 435/240.1 |
| 6,087,160 A * | 7/2000 | Yuan et al. ............... 435/320.1 |

FOREIGN PATENT DOCUMENTS

WO WO 91/19007 12/1991

OTHER PUBLICATIONS

Hengartner Mo et al. Nature 356:494–499, 1992.*
Sumrada et al. Genbank accession No. U43503, J. Bacteriology 160: 1078–1087, 1984.*
Yuan J et al Cell 75:641–652, 1993.*
Wilson R et al Nature 368:32–38, 1994.*
Ellis et al., "Genetic Control of Programmed Cell Death in the Nematode *C. elegans*", Cell 44:817–829 (1986). Yuan and Horvitz, "The *Caenorhabditis elegans* Genes ced–3 and ced–4 Act Cell Autonomoust to Cause Programmed Cell Death", Ann. Rev. Cell Biol. 134:33–41 (1991).
Ellis et al., "Mechansims and Functions of Cell Death", Ann. Rev. Cell Biol. 7:663–698 (1991).

Yuan and Horvitz, "The *Caenorhabditis elegans* cell death gene ced–4 encodes a novel protein and is expressed during the period of extensive programmed cell death", Development 116:309–320 (1992).
Ellis et al., "Genes Required for the Engulfment of Cell Corpses During Programmed Cell Death in *Caenorhabditis elegans*", Genetics 192:79–97 (1991).
Ellis and Horvitz, "Two *C. elegans* gene control the programmed deaths of specific cells in the pharynz", Development 112:591–603 (1991).
Avery and Horvitz, "A Cell that Dies During Wild–Type *C. elegans* Development can Function as a Neuron in a ced–3 Mutant", Cell 51:1071–1078 (1987).
Vaux et al., "Prevention of Programmed Cell Death in *Caenorhabditis elegans* by Human bcl–2", Science 258:1955–1957 (1992).
Vaux "Toward an Understanding of the molecular Mechanisms of Physiological Cell Death", Proc. Natl. Acad. Sci. USA 90:786–789 (1993).
Driscoll and Chalfie, "Developmental and Abnormal Cell Death in *C. elegans*", Trends in Neuroscience 15:15–19 (1992).
Driscoll, "Molecular Genetics of Cell Death in the Nematode *Caenorhabditis elegans*", J. of Neurobiology 23:1327–1351 (1992).
Freeman et al. "Cell Death Genes in Invertebrates and (maybe) Vertebrates", Current Opinion in Neurobiology 3:25–31 (1993).
Ledoux et al., "Isolation of Nematode Homologs of the *C. elegans* Cell Death Genes ced–3", Neurobiology of Aging 13:S47 (1992).
Yuan, "Genetic and Molecular Studies of ced 3 and ced 4 Two Genes that Control Programmed Cell Deaths with Nematode Celigri", Chapters 3 and 4 of Ph.D. Thesis (1990).
Siemeister et al., Plant Molecular Biology 14:825–822 (1990).

* cited by examiner

*Primary Examiner*—Ram R. Shukla
(74) *Attorney, Agent, or Firm*—Clark & Elbing LLP

(57) ABSTRACT

Described herein are genes shown to be essential for programmed cell death in *C. elegans*, their encoded products (RNA and polypeptides), antibodies directed against the encoded polypeptides; probes for identifying structurally related genes and bioassays for identifying functionally related cell death genes from various organisms; methods and agents for altering (increasing or decreasing) the activity of the cell death-genes and, thus, of altering cell death; and uses therefor. Specifically, two genes shown to be essential for almost all of the cell deaths which occur in the development of *C. elegans*, referred to as ced-3 and ced-4, have been cloned, sequenced and characterized.

6 Claims, 23 Drawing Sheets

FIG. 1A

```
     GAATTCGCGTCGAATCATTGTCTGTTCGGTATCGATTCAGAAACCGAAACTTGTGATCGA
   1 ------------------+---------+---------+---------+---------+   60
     TAACAAGTCATTCAAACACGGCGAAGATGTCTATGCGTATAACAGAATATTTGGAGAAAT
  61 ---------+---------+---------+---------+---------+---------+  120
     GCTCGCAAAACTCGAAATTGTCACCGATAAATGATTAACTTGAAGGGGCTAATGTAAGT
 121 ---------+---------+---------+---------+---------+---------+  180
     TATCTGATGTTTCTACAATTAAAAAAATTGTTTTTTTTCCAAATTAATTTTCGAAGATT
 181 ---------+---------+---------+---------+---------+---------+  240
     AACGAAAAACGATTAAAAATCAATAAAACGCAATAAAGAGGGCTTGGCTTTCTTTTTAAT
 241 ---------+---------+---------+---------+---------+---------+  300
     TTAAATTATAATTTTTCTGATTGTTGTATGAAGCTACAAAATGTACTGTTTTGTATTTG
 301 ---------+---------+---------+---------+---------+---------+  360
     AATATTGTATTACAGGGTTGGGATTCTCGGCAAATATCAGCGACAGTGGAAGATTTAGAA
 361 ---------+---------+---------+---------+---------+---------+  420
     GAAGGACGTGTGACAATCACTAAGTCAAAGAGGGAAAGGATAAAGGATTGTGATATTTCA
 421 ---------+---------+---------+---------+---------+---------+  480
     CTGTTTTACTCATTCGCTTTTTAAATAAGAACTATATGCCGATTTGCCGATATATTTTG
 481 ---------+---------+---------+---------+---------+---------+  540
     TTTATTAGGCCTCTCACATTCCTGTACAATGTTTCTACCAAATAAACTGCATTTTTATCT
 541 ---------+---------+---------+---------+---------+---------+  600
     GAAAATTCGAATTTATTTTTGTCTACTTTTTACTCGTTGCATTCGAGATCAGCATATCTT
 601 ---------+---------+---------+---------+---------+---------+  660
     CCGGTCTATTTATATTCAACGATTTTTATAAATTAGTACTCCTTCATGTTTAATTTCATT
 661 ---------+---------+---------+---------+---------+---------+  720
     TTATCTGTAAGCTTTACTGTATTTTTTTAAAATCTTTCTTGCTTCTATCTGATTATACAA
 721 ---------+---------+---------+---------+---------+---------+  780
     TGTTCTTTACTCATTTTCAAGGTATTTTTATGCCTCACAATTTATGCACATTTCGGGCTT
 781 ---------+---------+---------+---------+---------+---------+  840
     GGAGATTTATCCTCTATATTACATGCCTGTTTTTTAAAGGATATAATGTTTAACAAATA
 841 ---------+---------+---------+---------+---------+---------+  900
     ATTTTTTATCAATGCTATTGTATATTCTCCAGCTAACCGTTGTTTCGAAAACATCACCTA
 901 ---------+---------+---------+---------+---------+---------+  960
     GCATTTTAAAATTCACAAAATCTTGCTTCCTTATAATCAAGAAGATTTTTCAGATGCTCT
 961 ---------+---------+---------+---------+---------+---------+ 1020
                                                         M   L   C
                                                         1↓
     GCGAAATCGAATGCCGCGCTTTGAGCACGGCACACACGAGGCTCATCCACGACTTTGAAC
1021 ---------+---------+---------+---------+---------+---------+ 1080
       E   I   E   C   R   A   L   S   T   A   H   T   R   L   I   H   D   F   E   P
                          10                          20
                                                              T n1162
                                                              ↑
     CACGTGACGCATTGACTTATTTAGAAGGCAAAAACATTTTCACAGAAGATCATTCTGAAC
1081 ---------+---------+---------+---------+---------+---------+ 1140
       R   D   A   L   T   Y   L   E   G   K   N   I   F   T   E   D   H   S   E   L
                          30                          40
     TTATCAGTAAAATGTCAACTCGCCTCGAGAGGATCGCCAATTTTCTTCGAATCTATCGAC
1141 ---------+---------+---------+---------+---------+---------+ 1200
       I   S   K   M   S   T   R   L   E   R   I   A   N   F   L   R   I   Y   R   R
                          50                          60
     GTCAAGCTTCTGAACTTGGACCACTCATCGACTTTTTCAACTACAACAATCAAAGTCACC
1201 ---------+---------+---------+---------+---------+---------+ 1260
       Q   A   S   E   L   G   P   L   I   D   F   F   N   Y   N   N   Q   S   H   L
                          70                          80
```

FIG. 1B

```
     TTGCTGATTTCCTCGAAGACTACATCGATTTTGCGATAAATGAGCCAGATCTACTTCGTC
1261 ---------+---------+---------+---------+---------+---------+ 1320
       A  D  F  L  E  D  Y  I  D  F  A  I  N  E  P  D  L  L  R  P
                      90                         100

CAGTAGTGATTGCTCCACAATTTTCCCGACAAATGCTCGATAGGAAACTATTGCTTGGGA
1321 ---------+---------+---------+---------+---------+---------+ 1380
       V  V  I  A  P  Q  F  S  R  Q  M  L  D  R  K  L  L  L  G  N
                     110                         120
                                                    T n2274
                                                    ↑
     ATGTTCCAAAACAAATGACATGCTATATTCGAGAGTATCACGTGGATCGAGTGATCAAAA
1381 ---------+---------+---------+---------+---------+---------+ 1440
       V  P  K  Q  M  T  C  Y  I  R  E  Y  H  V  D  R  V  I  K  K
                     130                         140
                              | Intron 1
     AGCTCGACGAGATGTGTGATTTAG|GTGAGAAAACTGGAAGCTCTCGTGTTTATTATAATC
1441 ---------+---------+---------+---------+---------+---------+ 1500
       L  D  E  M  C  D  L  D
                     150

TTGCTTAAACTTCAG|ACTCCTTTTTTCTGTTTCTACACGGCCGAGCTGGATCCGGAAAAT
1501 ---------+---------+---------+---------+---------+---------+ 1560
                         S  F  F  L  F  L  H  G  R  A  G  S  G  K  S
                                                      160
                                                    | Intron 2
     CAGTAATTGCATCACAAGCTCTTTCGAAATCTGACCAACTTATTGGAAT|GTGAGTGGTAT
1561 ---------+---------+---------+---------+---------+---------+ 1620
       V  I  A  S  Q  A  L  S  K  S  D  Q  L  I  G  I
              170                         180
     TATCTGAATCTACGGATCTTCATTCTATTACAG|AAATTATGATTCAATCGTTTGGCTCAA
1621 ---------+---------+---------+---------+---------+---------+ 1680
                                         N  Y  D  S  I  V  W  L  K
                                                            190

AGATAGTGGAACAGCTCCAAAATCTACATTCGATTTATTTACGGATATTTTGCTGATGCT
1681 ---------+---------+---------+---------+---------+---------+ 1740
       D  S  G  T  A  P  K  S  T  F  D  L  F  T  D  I  L  L  M  L
                     200                         210
       A n1920/n2247
       ↑ Intron 3
     AAA|GTGAGTGAATAGAGTGCATGTAACATTCAGCATGATTTTGAAATTATGAAAATTTGA
1741 ---------+---------+---------+---------+---------+---------+ 1800
       K
     CCTGGTTAGCTTTTAATTTGATATTTCGTGACGCTTGCATGTTTTGTGTGTTTGAAGACG
1801 ---------+---------+---------+---------+---------+---------+ 1860
     AGCCCGTGTTGTGAGCGACACGGATGACTCGCATTCGATCACCGACTTCATTAACCGTGT
1861 ---------+---------+---------+---------+---------+---------+ 1920
           A n2273
           ↑
     TCTTTCAAG|AAGCGAAGACGATCTTCTCAATTTCCCATCGGTGGAGCATGTCACGTCAGT
1921 ---------+---------+---------+---------+---------+---------+ 1980
                   S  E  D  D  L  L  N  F  P  S  V  E  H  V  T  S  V
                                        220
```

FIG. 1C

```
              ↓ Intron 4
     TGTACTCAAAAGGATGGTAAGTTGCTTGCCGATTCTGGTACAATATCTTAAATTATTGGT
1981 ---------+---------+---------+---------+---------+---------+ 2040
     V  L  K  R  M 230 ↓
     TTTTAGATCTGCAACGCACTCATTGATCGTCCAAATACTTTATTCGTATTTGATGACGTA
2041 ---------+---------+---------+---------+---------+---------+ 2100
         I  C  N  A  L  I  D  R  P  N  T  L  F  V  F  D  D  V
                         240                                250
                  A n1948   T n1947
                     ↑       ↑
     GTTCAAGAAGAAACAATTCGTTGGGCTCAGGAGCTACGTCTTCGATGTCTTGTAACTACT
2101 ---------+---------+---------+---------+---------+---------+ 2160
     V  Q  E  E  T  I  R  W  A  Q  E  L  R  L  R  C  L  V  T  T
                         260                                270

CGTGACGTGGAAATATCAAATGCTGCTTCTCAAACATGCGAATTCATTGAAGTGACATCA
2161 ---------+---------+---------+---------+---------+---------+ 2220
     R  D  V  E  I  S  N  A  A  S  Q  T  C  E  F  I  E  V  T  S
                         280                                290

TTGGAAATCGATGAATGTTATGATTTTCTAGAAGCTTATGGAATGCCGATGCCTGTTGGA
2221 ---------+---------+---------+---------+---------+---------+ 2280
     L  E  I  D  E  C  Y  D  F  L  E  A  Y  G  M  P  M  P  V  G
                         300                                310
                                              Tc4 n1416
                                                 ↓
     GAAAAAGAAGAAGATGTGCTTAATAAAACAATCGAACTAAGCAGTGGAAATCCAGCAACG
2281 ---------+---------+---------+---------+---------+---------+ 2340
        E  K  E  E  D  V  L  N  K  T  I  E  L  S  S  G  N  P  A  T
                            320                                330
                                                           ↓ Intron 5
     CTTATGATGTTTTTCAAGTCTTGTGAACCGAAAACATTTGAAAAGTGAGTGGGACATACC
2341 ---------+---------+---------+---------+---------+---------+ 2400
     L  M  M  F  F  K  S  C  E  P  K  T  F  E  K
                         330

AATTTGAGACTTTTAAAATAATTTATTCTACAATAAAAGTTAATCAAAAAGTTTCATAGC
2401 ---------+---------+---------+---------+---------+---------+ 2460
     TGATTGTCTTTAAATTTTACGAATTGAGGATCAAAATCAAGAATTAGGATCCTGGCACGA
2461 ---------+---------+---------+---------+---------+---------+ 2520
     GAGAAAACTGTGTAGCTACCGTACCCGAGAGATTTTCTTGATATTTGCCATCGATTTAAT
2520 ---------+---------+---------+---------+---------+---------+ 2580
     TTTTTAAGAAAATTATCGTTTTACATAATTGAACAAGAGATACACGGTCTCGACCCGACG
2581 ---------+---------+---------+---------+---------+---------+ 2640
     GAAATTTTTAAATGAAAGCGAGTATGAGCCTGTTTTCATTATTTTTCGATTTTCTCTTG
2641 ---------+---------+---------+---------+---------+---------+ 2700
     TTGTTTCTTTTTATTTAAAGCCTTTTATTTTGAAACAAGTCTAAAAATATTAAAAACTGA
2701 ---------+---------+---------+---------+---------+---------+ 2760
     ATAAAATATTTAAAAAAAATCAAGTAAAATAGAAAAACAGCAAGGCTGGAGACTACTGTA
2760 ---------+---------+---------+---------+---------+---------+ 2820
     CTTCTTAAATCCGCATACTCTTTTTATTTAATCATTTTCCGGAATGTCGAAACGAAATAA
2821 ---------+---------+---------+---------+---------+---------+ 2880
     TACATTTTTAGTCCAAAATCGCTAGGTATATTCTTAAAATTATCAAACATTTTGCATTCA
```

FIG. 1D

```
2881 +---------+---------+---------+---------+---------+---------+ 2940
      GAATGGCACAGCTTAATAACAAATTGGAAAGTCGAGGATTAGTCGGTGTTGAATGTATCA
2941 +---------+---------+---------+---------+---------+---------+ 3000
        M  A  Q  L  N  N  K  L  E  S  R  G  L  V  G  V  E  C  I  T
              340                      350

CCCCTTACTCGTACAAGTCACTCGCAATGGCTCTTCAAAGATGTGTTGAAGTTTTGTCAG
3001 ----------+---------+---------+---------+---------+---------+ 3060
        P  Y  S  Y  K  S  L  A  M  A  L  Q  R  C  V  E  V  L  S  D
              360                      370

ATGAGGATCGAAGTGCTCTTGCTTTCGCAGTTGTGATGCCTCCTGGAGTTGATATACCCG
3061 ----------+---------+---------+---------+---------+---------+ 3120
        E  D  R  S  A  L  A  F  A  V  V  M  P  P  G  V  D  I  P  V
              380                      390
              A n1894
               ↑
      TCAAGCTATGGTCATGTGTTATTCCAGTTGATATTTGTTCAAATGAAGAAGAACAATTGG
3121 ----------+---------+---------+---------+---------+---------+ 3180
        K  L  W  S  C  V  I  P  V  D  I  C  S  N  E  E  E  Q  L  D
              400                      410
                                              Intron 6
      ATGATGAAGTTGCGGATCGGTTGAAAAGACTCAGCA|GTATGAGTCTTGAAATTTGAAGA
3181 ----------+---------+---------+------+---+---------+---------+ 3240
        D  E  V  A  D  R  L  K  R  L  S  K
                    420

TTTAAATTAACACTTAAAATTTCAG|ACGTGGAGCTCTTCTCAGTGGAAAACGAATGCCCG
3241 ----------+---------+----+----+---------+---------+---------+ 3300
                                  R  G  A  L  L  S  G  K  R  M  P  V
                                      430                      440

TTTTGACATTCAAAATTGATCATATTATCCATATGTTCTTGAAACACGTCGTTGATGCAC
3301 ----------+---------+---------+---------+---------+---------+ 3360
        L  T  F  K  I  D  H  I  I  H  M  F  L  K  H  V  V  D  A  Q
                          450                      460
              |Intron 7
      AAACTATCGC|GTATGCTGAAAATGTCTCAACTTTCAATTAAATTTTAAATTTTCAG|AAT
3361 ----------+-+--------+---------+---------+---------+-------+-+ 3420
        T  I  A                                                  N
      GGAATCTCAATTCTCGAGCAGCGTCTTCTTGAAATAGGAAACAATAATGTATCAGTACCG
3421 ----------+---------+---------+---------+---------+---------+ 3480
        G  I  S  I  L  E  Q  R  L  L  E  I  G  N  N  V  S  V  P
              470                      480

GAGCGACATATACCATCACATTTCCAAAAATTCCGTCGTTCATCAGCCAGTGAGATGTAT
3481 ----------+---------+---------+---------+---------+---------+ 3540
        E  R  H  I  P  S  H  F  Q  K  F  R  R  S  A  S  E  M  Y
              500                      510

CCAAAAACTACAGAAGAAACTGTGATCCGTCCTGAAGACTTCCCAAAGTTCATGCAATTG
3541 ----------+---------+---------+---------+---------+---------+ 3600
        P  K  T  T  E  E  T  V  I  R  P  E  D  F  P  K  F  M  Q  L
              520                      530

CACCAGAAATTCTATGACTCCCTCAAAAATTTTGCATGCTGTTAAAACCTATCGTGTACA
3601 ----------+---------+---------+---------+---------+---------+ 3660
        H  Q  K  F  Y  D  S  L  K  N  F  A  C  C  *
              540

ATATTGCCTGTATATTCCCCTCGAAATACGTTTATACTTTTTCGCACGAGTTTTCTCATT
```

FIG. 1E

```
3661 ---------+---------+---------+---------+---------+---------+ 3720
     TTTTCATTTGTACTTGTTTTATTTCTCTCCAAAATTTCAGATCTATCCCAAATGTTCTTA
3721 ---------+---------+---------+---------+---------+---------+ 3780
     AATTTAATGTTTTCTACAGATACTCAACACATCTTGTTTCATCTCATCCTTGCTTTTTTT
3781 ---------+---------+---------+---------+---------+---------+ 3840
     TTTCAAATATATTCAGTTTCTTTTATAATTTTAATTAATCGAATTAATACATTCACGTAA
3841 ---------+---------+---------+---------+---------+---------+ 3900
     AGAATTTCGTGGACTATTATTTTATCGCATCCAAATGATTTATTCCCTATTGTTCGAAAC
3901 ---------+---------+---------+---------+---------+---------+ 3960
     TTCCAAATTGATCATTTTAAACACGCCTCATTAAATTGAAAGTCGTACTTTTAGTCTCG
3961 ---------+---------+---------+---------+---------+---------+ 4020
     AACATGAAGTAAGTTATTTTCTGTGTTCTAAATTCAAAGTGCATTCCAAAAGGACATTTG
4021 ---------+---------+---------+---------+---------+---------+ 4080
     ATGAGTTTTCACGAAAACCGTAATTTTTACAATTTCCTTTCAGTTTTGAAGATGTTCGAT
4081 ---------+---------+---------+---------+---------+---------+ 4140
     TTCTTTCCTCTGTTGGCGTCATTACTACATTTGCTTTGCTGCTTCACTTTATCGAGATTC
4141 ---------+---------+---------+---------+---------+---------+ 4200
     TTGCCATCAATGGAGTTCCATCTAGACCGATAGCAGTCTTCATATCATTATCCCTGTATA
4201 ---------+---------+---------+---------+---------+---------+ 4260
     TTGTACTGTTTCAGTATTTTAACTTATCGATTACGTACTATATTCAGTGGTTCACTGTTT
4261 ---------+---------+---------+---------+---------+---------+ 4320
     TCGGTCAATGGGTGACACGTGCTCGACGANNAATTTTCAACGAACGCAATCTCCTAGTCA
4320 ---------+---------+---------+---------+---------+---------+ 4380
     CTTATCAACCAAGAGCCCTCACCCATG
4380 ---------+---------+------- 4407
```

FIG. 3

|  | 10 | 12 | 14 |  |  | 18 |  |  | 21 |
|---|---|---|---|---|---|---|---|---|---|
|  | X | Y | Z |  |  | -X |  |  | -Z |
| Calcium-binding loop concensus | D | N | S |  |  | T |  |  | E |
|  |  | D | N |  |  | S |  |  |  |
|  |  |  | D |  |  | E |  |  |  |
|  |  |  |  |  |  | Q |  |  |  |
|  |  |  |  |  |  | D |  |  |  |
|  |  |  |  |  |  | N |  |  |  |

| EF-hand consensus | O * O * O G * * O * * E |
|---|---|
| ced-4 sequence 1 | Y N N Q S H L A D F L E |
| sequence 2 | S L E I D E C Y D F L E |
| Parvalbumin (carp) | D Q D K S G F I E E D E |
| (hake) | D Q D K D D F I G E D E |
| (ray) | D S D G D H K I G V D E |
| SCBP (Amphioxus I) | D I N K D D V V S W E E |
| ICaBP (bovine) | A K E G D P Q L S K E E |
|  | D K N G D G E V S F E E |
| Troponin C (rabbit) | D A D G G G D I S V K E |
|  | D E D G S G T I D F E E |
|  | D R N A D G Y I D A E E |
|  | D K N N D G R I D F D E |
| Calmodulin (bovine) | D K D G N G T I T T K E |
| Trypsinogen | L G E D N I N VVE G N E |
| Fibrinogen | D N D N D K F EGN C A E |
| Villin | G V D P S R K E N H L S |
| GBP | D L N K D G Q I Q _ I E |

FIG. 4A
ced-3 Genomic Sequence

```
     AGATCTGAAATAAGGTGATAAATTAATAAATTAAGTGTATTTCTGAGGAAATTTGACTGT
   1 ---------+---------+---------+---------+---------+---------+  60
     TTTAGCACAATTAATCTTGTTTCAGAAAAAAAGTCCAGTTTTCTAGATTTTTCCGTCTTA
  61 ---------+---------+---------+---------+---------+---------+ 120
     TTGTCGAATTAATATCCCTATTATCACTTTTTCATGCTCATCCTCGAGCGGCACGTCCTC
 121 ---------+---------+---------+---------+---------+---------+ 180
     AAAGAATTGTGAGAGCAAACGCGCTCCCATTGACCTCCACACTCAGCCGCCAAAACAAAC
 181 ---------+---------+---------+---------+---------+---------+ 240
     GTTCGAACATTCGTGTGTTGTGCTCCTTTTCCGTTATCTTGCAGTCATCTTTTGTCGTTT
 241 ---------+---------+---------+---------+---------+---------+ 300
     TTTTCTTTGTTCTTTTTGTTGAACGTGTTGCTAAGCAATTATTACATCAATTGAAGAAAA
 301 ---------+---------+---------+---------+---------+---------+ 360
     GGCTCGCCGATTTATTGTTGCCAGAAAGATTCTGAGATTCTCGAAGTCGATTTTATAATA
 361 ---------+---------+---------+---------+---------+---------+ 420
     TTTAACCTTGGTTTTTGCATTGTTTCGTTTAAAAAAACCACTGTTTATGTGAAAAACGAT
 421 ---------+---------+---------+---------+---------+---------+ 480
     TAGTTTACTAATAAAACTACTTTTAAACCTTTACCTTTACCTCACCGCTCCGTGTTCATG
 481 ---------+---------+---------+---------+---------+---------+ 540
     GCTCATAGATTTTCGATACTCAAATCCAAAAATAAATTTACGAGGGCAATTAATGTGAAA
 541 ---------+---------+---------+---------+---------+---------+ 600
     CAAAAACAATCCTAAGATTTCCACATGTTTGACCTCTCCGGCACCTTCTTCCTTAGCCCC
 601 ---------+---------+---------+---------+---------+---------+ 660
     ACCACTCCATCACCTCTTTGGCGGTGTTCTTCGAAACCCACTTAGGAAAGCAGTGTGTAT
 661 ---------+---------+---------+---------+---------+---------+ 720
     CTCATTTGGTATGCTCTTTTCGATTTTATAGCTCTTTGTCGCAATTTCAATGCTTTAAAC
 721 ---------+---------+---------+---------+---------+---------+ 780
     AATCCAAATCGCATTATATTTGTGCATGGAGGCAAATGACGGGGTTGGAATCTTAGATGA
 781 ---------+---------+---------+---------+---------+---------+ 840
     GATCAGGAGCTTTCAGGGTAAACGCCCGGTTCATTTGTACCACATTTCATCATTTTCCT
 841 ---------+---------+---------+---------+---------+---------+ 900
     GTCGTCCTTGGTATCCTCAACTTGTCCCGGTTTTGTTTTCGGTACACTCTTCCGTGATGC
 901 ---------+---------+---------+---------+---------+---------+ 960
     CACCTGTCTCCGTCTCAATTATCGTTTAGAAATGTGAACTGTCCAGATGGGTGACTCATA
 961 ---------+---------+---------+---------+---------+---------+ 1020
     TTGCTGCTGCTACAATCCACTTTCTTTTCTCATCGGCAGTCTTACGAGCCCATCATAAAC
1021 ---------+---------+---------+---------+---------+---------+ 1080
     TTTTTTTTCCGCGAAATTTGCAATAAACCGGCCAAAAACTTTCTCCAAATTGTTACGCAA
1081 ---------+---------+---------+---------+---------+---------+ 1140
     TATATACAATCCATAAGAATATCTTCTCAATGTTTATGATTTCTTCGCAGCACTTTCTCT
1141 ---------+---------+---------+---------+---------+---------+ 1200
     TCGTGTGCTAACATCTTATTTTTATAATATTTCCGCTAAAATTCCGATTTTTGAGTATTA
1201 ---------+---------+---------+---------+---------+---------+ 1260
     ATTTATCGTAAAATTATCATAATAGCACCGAAAACTACTAAAAATGGTAAAAGCTCCTTT
1261 ---------+---------+---------+---------+---------+---------+ 1320
                                                         Repeat 1
                                                   ---------------
     TAAATCGGCTCGACATTATCGTATTAAGGAATCACAAAATTCTGAGAATGCGTACTGCGC
1321 ---------+---------+---------+---------+---------+---------+ 1380
     ------------------------------------
     AACATATTTGACGGCAAAATATCTCGTAGCGAAAACTACAGTAATTCTTTAAATGACTAC
1381 ---------+---------+---------+---------+---------+---------+ 1440
```

FIG. 4B

```
                                                        Repeat 1
     ------------------------>        <-------
     TGTAGCGCTTGTGTCGATTTACGGGCTCAATTTTTGAAAATAATTTTTTTTTTCGAATTT
1441 ---------+---------+---------+---------+---------+---------+ 1500

------------------------------------------------------------
     TGATAACCCGTAAATCGTCACAACGCTACAGTAGTCATTTAAAGGATTACTGTAGTTCTA
1501 ---------+---------+---------+---------+---------+---------+ 1560

-----,------------------------------------------
     GCTACGAGATATTTTGCGCGCCAAATATGACTGTAATACGCATTCTCTGAATTTTGTGTT
1561 ---------+---------+---------+---------+---------+---------+ 1620
     TCCGTAATAATTTCACAAGATTTTGGCATTCCACTTTAAAGGCGCACAGGATTTATTCCA
1621 ---------+---------+---------+---------+---------+---------+ 1680
     ATGGGTCTCGGCACGCAAAAAGTTTGATAGACTTTTAAATTCTCCTTGCATTTTTAATTC
1681 ---------+---------+---------+---------+---------+---------+ 1740
     AATTACTAAAATTTTCGTGAATTTTTCTGTTAAAATTTTTAAAATCAGTTTTCTAATATT
1741 ---------+---------+---------+---------+---------+---------+ 1800
     TTCCAGGCTGACAAACAGAAACAAAAACACAACAAACATTTTAAAAATCAGTTTTCAAAT
1801 ---------+---------+---------+---------+---------+---------+ 1860
     TAAAAATAACGATTTCTCATTGAAAATTGTGTTTATGTTTGCGAAAATAAAAGAGAACT
1861 ---------+---------+---------+---------+---------+---------+ 1920
     GATTCAAAACAATTTTAACAAAAAAAAAACCCCAAAATTCGCCAGAAATCAAGATAAAAAA
1921 ---------+---------+---------+---------+---------+---------+ 1980
     TTCAAGAGGGTCAAAATTTTCCGATTTTACTGACTTTCACCTTTTTTTTCGTAGTTCAGT
1981 ---------+---------+---------+---------+---------+---------+ 2040
     GCAGTTGTTGGAGTTTTTGACGAAAACTAGGAAAAAAATCGATAAAAATTACTCAAATCG
2041 ---------+---------+---------+---------+---------+---------+ 2100
     AGCTGAATTTTGAGGACAATGTTTAAAAAAAAACACTATTTTTCCAATAATTTCACTCAT
2101 ---------+---------+---------+---------+---------+---------+ 2160

-----
     TTTCAGACTAAATCGAAAATCAAATCGTACTCTGACTACGGGTCAGTAGAGAGGTCAACC
     ------
2161 ---------+---------+---------+---------+---------+---------+ 2220

ATCAGCCGAAGATGATGCGTCAAGATAGAAGGAGCTTGCTAGAGAGGAACATTATGATGT
2221 ---------+---------+---------+---------+---------+---------+ 2280
                       M  M  R  Q  D  R  R  S  L  L  E  R  N  I  M  M  F
                       1                           10
                                  T (n1040)
                                    |
     TCTCTAGTCATCTAAAAGTCGATGAAATTCTCGAAGTTCTCATCGCAAAACAAGTGTTGA
2281 ---------+---------+---------+---------+---------+---------+ 2340
        S  S  H  L  K  V  D  E  I  L  E  V  L  I  A  K  Q  V  L  N
                 20                          30
                                  |Intron 1
     ATAGTGATAATGGAGATATGATTAATGTGAGTTTTTAATCGAATAATAATTTTAAAAAAA
2341 ---------+---------+---------+---------+---------+---------+ 2400
        S  D  N  G  D  M  I  N
                 40
```

FIG. 4C

```
              AATTGATAATATAAAGAATATTTTTGCAGTCATGTGGAACGGTTCGCGAGAAGAGACGGG
2401     ---------+---------+---------+---------+---------+---------+ 2460
                                    S  C  G  T  V  R  E  K  R  R  E
                                                    50
                          A (n718)
                              |
         AGATCGTGAAAGCAGTGCAACGACGGGGAGATGTGGCGTTCGACGCGTTTTATGATGCTC
2461     ---------+---------+---------+---------+---------+---------+ 2520
          I  V  K  A  V  Q  R  R  G  D  V  A  F  D  A  F  Y  D  A  L
                60                            70
                                                              |Intron 2
         TTCGCTCTACGGGACACGAAGGACTTGCTGAAGTTCTTGAACCTCTCGCCAGATCGTAGG
2521     ---------+---------+---------+---------+---------+---------+ 2580
            R  S  T  G  H  E  G  L  A  E  V  L  E  P  L  A  R  S
                      80                            90

TTTTTAAAGTTCGGCGCAAAAGCAAGGGTCTCACGGAAAAAAGAGGCGGATCGTAATTTT
2581     ---------+---------+---------+---------+---------+---------+ 2640
         GCAACCCACCGGCACGGTTTTTTCCTCCGAAAATCGGAAATTATGCACTTTCCCAAATAT
2641     ---------+---------+---------+---------+---------+---------+ 2700
         TTGAAGTGAAATATATTTTATTTACTGAAAGCTCGAGTGATTATTTATTTTTTAACACTA
2701     ---------+---------+---------+---------+---------+---------+ 2760
         ATTTTCGTGGCGCAAAAGGCCATTTTGTAGATTTGCCGAAAATACTTGTCACACACACAC
2761     ---------+---------+---------+---------+---------+---------+ 2820

ACACACATCTCCTTCAAATATCCCTTTTTCCAGTGTTGACTCGAATGCTGTCGAATTCGA
2821     ---------+---------+---------+---------+---------+---------+ 2880
                                              V  D  S  N  A  V  E  F  E
                                                                   100

GTGTCCAATGTCACCGGCAAGCCATCGTCGGAGCCGCGCATTGAGCCCCGCCGGCTACAC
2881     ---------+---------+---------+---------+---------+---------+ 2940
          C  P  M  S  P  A  S  H  R  R  S  R  A  L  S  P  A  G  Y  T
                      110                           120

TTCACCGACCCGAGTTCACCGTGACAGCGTCTCTTCAGTGTCATCATTCACTTCTTATCA
2941     ---------+---------+---------+---------+---------+---------+ 3000
            S  P  T  R  V  H  R  D  S  V  S  S  V  S  S  F  T  S  Y  Q
                      130                           140

GGATATCTACTCAAGAGCAAGATCTCGTTCTCGATCGCGTGCACTTCATTCATCGGATCG
3001     ---------+---------+---------+---------+---------+---------+ 3060
            D  I  Y  S  R  A  R  S  R  S  R  A  L  H  S  S  D  R
                      150                           160
                                                              | Intron 3
         ACACAATTATTCATCTCCTCCAGTCAACGCATTTCCCAGCCAACCTTGTATGTTGATGCG
3061     ---------+---------+---------+---------+---------+---------+ 3120
            H  N  Y  S  S  P  P  V  N  A  F  P  S  Q  P  S
                      170
```

FIG. 4D

```
              Repeat 1
       _____
       AACACTAAATTCTGAGAATGCGCATTACTCAACATATTTGACGCGCAAATATCTCGTAGC
3121   ---------+---------+---------+---------+---------+---------+ 3180

_____
       GAAAAATACAGTAACCCTTTAAATGACTATTGTAGTGTCGATTTACGGGCTCGATTTTCG
3181   ---------+---------+---------+---------+---------+---------+ 3240

-->
       AAACGAATATATGCTCGAATTGTGACAACGAATTTTAATTTGTCATTTTTGTGTTTTCTT
3241   ---------+---------+---------+---------+---------+---------+ 3300

Repeat 1
                        <---------------------------------
       TTGATATTTTTGATCAATTAATAAATTATTTCCGTAAACAGACACCAGCGCTACAGTACT
3301   ---------+---------+---------+---------+---------+---------+ 3360

_____
       CTTTTAAAGAGTTACAGTAGTTTTCGCTTCAAGATATTTGAAAAGAATTTTAAACATTT
3361   ---------+---------+---------+---------+---------+---------+ 3420

TGAAAAAAAATCATCTAACATGTGCCAAAACGCTTTTTTCAAGTTTCGCAGATTTTTTGA
3421   ---------+---------+---------+---------+---------+---------+ 3480

Repeat 2
       _____
       TTTTTTTTCATTCAAGATATGCTTATTAACACATATAATTATCATTAATGTGAATTTCTTG
3481   ---------+---------+---------+---------+---------+---------+ 3540

_____
       TAGAAATTTTGGGCTTTTCGTTCTAGTATGCTCTACTTTTGAAATTGCTCAACGAAAAAA
3541   ---------+---------+---------+---------+---------+---------+ 3600

_____
       TCATGTGGTTTGTTCATATGAATGACGAAAAATAGCAATTTTTTATATATTTTCCCCTAT
3601   ---------+---------+---------+---------+---------+---------+ 3660

_____
       TCATGTTGTGCAGAAAAATAGTAAAAAAGCGCATGCATTTTTCGACATTTTTTACATCGA
3661   ---------+---------+---------+---------+---------+---------+ 3720

_____-->
       ACGACAGCTCACTTCACATGCTGAAGACGAGAGACGCGGAGAAATACCACACATCTTTCT
3721   ---------+---------+---------+---------+---------+---------+ 3780

Repeat 2
       <-----------------------------------------------
       GCGTCTCTCGTCTTCAGCATGTGAAATGGGATCTCGGTCGATGTAAAAAAATGTCGAATA
3781   ---------+---------+---------+---------+---------+---------+ 3840

_____
       ATGTAAAAAAATGCATGCGTTTTTTTACACTTTTCTGCACAAATGAATAGGGGGAAAATGT
3841   ---------+---------+---------+---------+---------+---------+ 3900
```

FIG. 4E

```
           ATTAAAATACATTTTTTGTATTTTTCAACATCACATGATTAACCCCATTATTTTTTCGTT
3901     ---------+---------+---------+---------+---------+---------+ 3960

GAGCAACTTAAAAAGTAGAGAATATTAGAGCGAAAACCAAAATTTCTTCAAGATATTACC
3961     ---------+---------+---------+---------+---------+---------+ 4020

TTTATTGATAATTATAGATGTTAATAAGCATATCTTGAATGAAAGTCAGCAAAAATATGT
4021     ---------+---------+---------+---------+---------+---------+ 4080
           GCGAAACACCTGAAAAAAATCAAAAATTCTGCGAAAATTGAAAAAATGCATTAAAATACA
4081     ---------+---------+---------+---------+---------+---------+ 4140
           TTTTTGCATTTTTCTACATCACATGAATGTAGAAAATTAAAAGGGAAATCAAAATTTCTA
4141     ---------+---------+---------+---------+---------+---------+ 4200
           GAGGATATAATTGAATGAAACATTGCGAAATTAAAATGTGCGAAACGTCAAAAAAGAGGA
4201     ---------+---------+---------+---------+---------+---------+ 4260
                                                      |
           AATTTGGGTATCAAAATCGATCCTAAAACCAACACATTTCAGCATCCGCCAACTCTTCAT
4261     ---------+---------+---------+---------+---------+---------+ 4320
                                                     S   A   N   S   S   F
                                                                180

TCACCGGATGCTCTTCTCTCGGATACAGTTCAAGTCGTAATCGCTCATTCAGCAAAGCTT
4321     ---------+---------+---------+---------+---------+---------+ 4380
             T   G   C   S   S   L   G   Y   S   S   R   N   R   S   F   S   K   A   S
                         190                                 200

CTGGACCAACTCAATACATATTCCATGAAGAGGATATGAACTTTGTCGATGCACCAACCA
4380     ---------+---------+---------+---------+---------+---------+ 4440
              G   P   T   Q   Y   I   F   H   E   E   D   M   N   F   V   D   A   P   T   I
                             210                                 220

TAAGCCGTGTTTTCGACGAGAAAACCATGTACAGAAACTTCTCGAGTCCTCGTGGAATGT
4441     ---------+---------+---------+---------+---------+---------+ 4500
              S   R   V   F   D   E   K   T   M   Y   R   N   F   S   S   P   R   G   M   C
                             230                                 240

GCCTCATCATAAATAATGAACACTTTGAGCAGATGCCAACACGGAATGGTACCAAGGCCG
4501     ---------+---------+---------+---------+---------+---------+ 4560
              L   I   I   N   N   E   H   F   E   Q   M   P   T   R   N   G   T   K   A   D
                             250                                 260

ACAAGGACAATCTTACCAATTTGTTCAGATGCATGGGCTATACGGTTATTTGCAAGGACA
4561     ---------+---------+---------+---------+---------+---------+ 4620
              K   D   N   L   T   N   L   F   R   C   M   G   Y   T   V   I   C   K   D   N
                             270                                 280

| Intron 4
           ATCTGACGGGAAGGGTACGGCGAAATTATATTACCCAAACGCGAAATTTGCCATTTTGCG
4621     ---------+---------+---------+---------+---------+---------+ 4680
              L   T   G   R
```

FIG. 4F

```
         Repeat 3
     ------------------->
     CCGAAAATGTGGCGCCCGGTCTCGACACGACAATTTGTGTTAAATGCAAAAATGTATAAT
4681 ---------+---------+---------+---------+---------+---------+ 4740
     TTTGCAAAAAACAAAATTTTGAACTTCCGCGAAAATGATTTACCTAGTTTCGAAATTTTC
4741 ---------+---------+---------+---------+---------+---------+ 4800
     GTTTTTTCCGGCTACATTATGTGTTTTTTCTTAGTTTTTCTATAATATTTGATGTAAAAA
4801 ---------+---------+---------+---------+---------+---------+ 4860
     ACCGTTTGTAAATTTTCAGACAATTTTCCGCATACAAAACTTGATAGCACGAAATCAATT
4861 ---------+---------+---------+---------+---------+---------+ 4920
     TTCTGAATTTTCAAAATTATCCAAAAATGCACAATTTAAAATTTGTGAAAATTGGCAAAC
4921 ---------+---------+---------+---------+---------+---------+ 4980
     GGTGTTTCAATATGAAATGTATTTTTAAAAACTTTAAAAACCACTCCGGAAAAGCAATAA
4981 ---------+---------+---------+---------+---------+---------+ 5040
     AAATCAAAACAACGTCACAATTCAAATTCAAAAGTTATTCATCCGATTTGTTTATTTTTG
5041 ---------+---------+---------+---------+---------+---------+ 5100
     CAAAATTTGAAAAAATCATGAAGGATTTAGAAAAGTTTTATAACATTTTTTCTAGATTTT
5101 ---------+---------+---------+---------+---------+---------+ 5160
     TCAAAATTTTTTTTAACAAATCGAGAAAAAGAGAATGAAAAATCGATTTTAAAAATATCC
5161 ---------+---------+---------+---------+---------+---------+ 5220

Repeat 3
     <--------------------------------------------
     ACAGCTTCGAGAGTTTGAAATTACAGTACTCCTTAAAGGCGCACACCCCATTTGCATTGG
5221 ---------+---------+---------+---------+---------+---------+ 5280

--------------------------------------------
     ACCAAAAATTTGTCGTGTCGAGACCAGGTACCGTAGTTTTTGTCGCAAAAATTGCACCAT
5281 ---------+---------+---------+---------+---------+---------+ 5340
     TGGACAATAAACCTTCCTAATCACCAAAAAGTAAAATTGAAATCTTCGAAAAGCCAAAAA
5341 ---------+---------+---------+---------+---------+---------+ 5400
     ATTCAAAAAAAAAGTCGAATTTCGATTTTTTTTTTGGTTTTTTGGTCCCAAAAACCAAAA
5401 ---------+---------+---------+---------+---------+---------+ 5460
     AAATCAATTTTCTGCAAAATACCAAAAAGAAACCCGAAAAAATTTCCCAGCCTTGTTCCT
5461 ---------+---------+---------+---------+---------+---------+ 5520
                          |
     AATGTAAACTGATATTTAATTTCCAGGGAATGCTCCTGACAATTCGAGACTTTGCCAAAC
5521 ---------+---------+---------+---------+---------+---------+ 5580
                                   G  M  L  T  I  R  D  F  A  K  H
                                   290                         300

ACGAATCACACGGAGATTCTGCGATACTCGTGATTCTATCACACGGAGAAGAGAATGTGA
5581 ---------+---------+---------+---------+---------+---------+ 5640
      E  S  H  G  D  S  A  I  L  V  I  L  S  H  G  E  E  N  V  I
                              310                         320

TTATTGGAGTTGATGATATACCGATTAGTACACACGAGATATATGATCTTCTCAACGCGG
5641 ---------+---------+---------+---------+---------+---------+ 5700
        I  G  V  D  D  I  P  I  S  T  H  E  I  Y  D  L  L  N  A  A
                              330                         340
```

FIG. 4G

```
                                                           A (n2433)
                                                           |  |Intron 5
     CAAATGCTCCCCGTCTGGCGAATAAGCCGAAAATCGTTTTTGTGCAGGCTTGTCGAGGCG
5701 ---------+---------+---------+---------+---------+---------+ 5760
       N  A  P  R  L  A  N  K  P  K  I  V  F  V  Q  A  C  R  G  E
                          350                               360
                                                               |
     GTTCGTTTTTTATTTTAATTTTAATATAAATATTTTAAATAAATTCATTTTCAGAACGTC
5761 ---------+---------+---------+---------+---------+---------+ 5820
                                                            R  R GTGACAATGGATTCCCAGTCTTGGATTCTGTCGACGGAGTTCCTGCATTTCTTCGTCGTG
5821 ---------+---------+---------+---------+---------+---------+ 5880
        D  N  G  F  P  V  L  D  S  V  D  G  V  P  A  F  L  R  R  G
                          370                               380

T (n1165)
                                                           |
     GATGGGACAATCGAGACGGGCCATTGTTCAATTTTCTTGGATGTGTGCGGCCGCAAGTTC
5881 ---------+---------+---------+---------+---------+---------+ 5940
        W  D  N  R  D  G  P  L  F  N  F  L  G  C  V  R  P  Q  V  Q
                          390                               400

| Intron 6
     AGGTTGCAATTTAATTTCTTGAATGAGAATATTCCTTCAAAAAATCTAAAATAGATTTTT
5941 ---------+---------+---------+---------+---------+---------+ 6000
     ATTCCAGAAAGTCCCGATCGAAAAATTGCGATATAATTACGAAATTTGTGATAAAATGAC
6001 ---------+---------+---------+---------+---------+---------+ 6060

Repeat 4
     ------------------------------------------------------------
     AAACCAATCAGCATCGTCGATCTCCGCCCACTTCATCGGATTGGTTTGAAAGTGGGCGGA
6061 ---------+---------+---------+---------+---------+---------+ 6120

----------->
     GTGAATTGCTGATTGGTCGCAGTTTTCAGTTTAGAGGGAATTTAAAAATCGCCTTTTCGA
6121 ---------+---------+---------+---------+---------+---------+ 6180
     AAATTAAAAATTGATTTTTTCAATTTTTTCGAAAAATATTCCGATTATTTTATATTCTTT
6181 ---------+---------+---------+---------+---------+---------+ 6240

A (n717)
                                                           |
     GGAGCGAAAGCCCCGTCCTGTAAACATTTTTAAATGATAATTAATAAATTTTTGCAGCAA
6241 ---------+---------+---------+---------+---------+---------+ 6300
                                                               Q

T (n1949)
                 |
     GTGTGGAGAAAGAAGCCGAGCCAAGCTGACATTCTGATTCGATACGCAACGACAGCTCAA
6301 ---------+---------+---------+---------+---------+---------+ 6360
        V  W  R  K  K  P  S  Q  A  D  I  L  I  R  Y  A  T  T  A  Q
                          410                               420
```

FIG. 4H

```
                   A (n1286)
                      |
          TATGTTTCGTGGAGAAACAGTGCTCGTGGATCATGGTTCATTCAAGCCGTCTGTGAAGTG
6361      ---------+---------+---------+---------+---------+---------+ 6420
            Y  V  S  W  R  N  S  A  R  G  S  W  F  I  Q  A  V  C  E  V
                        430                              440

T (n1129, n1164)
                   |
          TTCTCGACACACGCAAAGGATATGGATGTTGTTGAGCTGCTGACTGAAGTCAATAAGAAG
6421      ---------+---------+---------+---------+---------+---------+ 6480
            F  S  T  H  A  K  D  M  D  V  V  E  L  L  T  E  V  N  K  K
                           450                              460

T (n2430)                                    A (n2426)
                 |                                          |  | Intron 7
          GTCGCTTGTGGATTTCAGACATCACAGGGATCGAATATTTTGAAACAGATGCCAGAGGTA
6481      ---------+---------+---------+---------+---------+---------+ 6540
            V  A  C  G  F  Q  T  S  Q  G  S  N  I  L  K  Q  M  P  E
                           470                              480

Repeat 5
                          ------------------------------
          CTTGAAACAAACAATGCATGTCTAACTTTTAAGGACACAGAAAAATAGGCAGAGGCTCCT
6541      ---------+---------+---------+---------+---------+---------+ 6600

--------------->
          TTTGCAAGCCTGCCGCGCGTCAACCTAGAATTTTAGTTTTTAGCTAAAATGATTGATTTT
6601      ---------+---------+---------+---------+---------+---------+ 6660
          GAATATTTTATGCTAATTTTTTTGCGTTAAATTTTGAAATAGTCACTATTTATCGGGTTT
6661      ---------+---------+---------+---------+---------+---------+ 6720
          CCAGTAAAAAATGTTTATTAGCCATTGGATTTTACTGAAAACGAAAATTTGTAGTTTTTC
6721      ---------+---------+---------+---------+---------+---------+ 6780
          AACGAAATTTATCGATTTTTAAATGTAAAAAAAAATAGCGAAAATTACATCAACCATCAA
6781      ---------+---------+---------+---------+---------+---------+ 6840
          GCATTTAAGCCAAAATTGTTAACTCATTTAAAAATTAATTCAAAGTTGTCCACGAGTATT
6841      ---------+---------+---------+---------+---------+---------+ 6900

Repeat 5
            <----------------------------------------------
          ACACGGTTGGCGCGCGGCAAGTTTGCAAAACGACGCTCCGCCTCTTTTTCTGTGCGGCTT
6901      ---------+---------+---------+---------+---------+---------+ 6960

T (n1163)
          ----                                         |             |
          GAAAACAAGGGATCGGTTTAGATTTTTCCCCAAAATTTAAATTAAATTTCAGATGACATC
6961      ---------+---------+---------+---------+---------+---------+ 7020
                                                                 M  T  S

CCGCCTGCTCAAAAAGTTCTACTTTTGGCCGGAAGCACGAAACTCTGCCGTCTAAAATTC
7021      ---------+---------+---------+---------+---------+---------+ 7080
            R  L  L  K  K  F  Y  F  W  P  E  A  R  N  S  A  V  *
                        490                              500
```

FIG. 4I

```
        ACTCGTGATTCATTGCCCAATTGATAATTGTCTGTATCTTCTCCCCCAGTTCTCTTTCGC
7081    ---------+---------+---------+---------+---------+---------+ 7140
        CCAATTAGTTTAAAACCATGTGTATATTGTTATCCTATACTCATTTCACTTTATCATTCT
7141    ---------+---------+---------+---------+---------+---------+ 7200
        ATCATTTCTCTTCCCATTTTCACACATTTCCATTTCTCTACGATAATCTAAAATTATGAC
7201    ---------+---------+---------+---------+---------+---------+ 7260
        GTTTGTGTCTCGAACGCATAATAATTTTAATAACTCGTTTTGAATTTGATTAGTTGTTGT
7261    ---------+---------+---------+---------+---------+---------+ 7320
        GCCCAGTATATATGTATGTACTATGCTTCTATCAACAAAATAGTTTCATAGATCATCACC
7321    ---------+---------+---------+---------+---------+---------+ 7380
        CCAACCCCACCAACCTACCGTACCATATTCATTTTTGCCGGGAATCAATTTCGATTAATT
7381    ---------+---------+---------+---------+---------+---------+ 7440
        TTAACCTATTTTTTCGCCACAAAAAATCTAATATTTGAATTAACGAATAGCATTCCCATC
7441    ---------+---------+---------+---------+---------+---------+ 7500
        TCTCCCGTGCCGGAATGCCTCCCGGCCTTTTAAAGTTCGGAACATTTGGCAATTATGTAT
7501    ---------+---------+---------+---------+---------+---------+ 7560
        AAATTTGTAGGTCCCCCCCATCATTTCCCGCCCATCATCTCAAATTGCATTCTTTTTTCG
7561    ---------+---------+---------+---------+---------+---------+ 7620
        CCGTGATATCCCGATTCTGGTCAGCAAAGATCT
7621    ---------+---------+---------+--- 7653
```

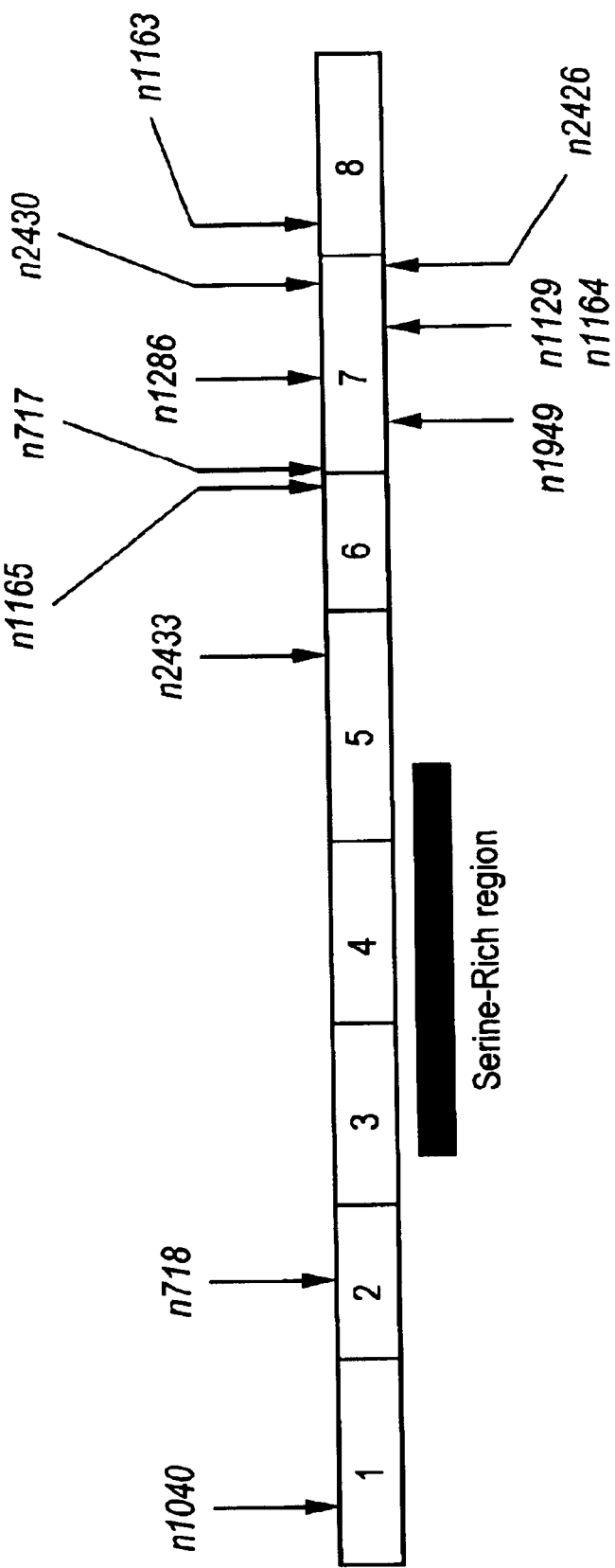

FIG. 7

```
Lines
  1   01 MMRQDRRSLLERNIMMFSSHLKVDEILEVLIAKQVLNSDNGDMINSCGTV  50
  2        .....W_.....LE...K.QA.L..D.............V....R.E
  3                        TVS.SLI..R....... M.....

1   51 REKRREIVKAVQRPGDVAFDAFYDALRSTGHEGLAEVLEPLARSVDSNAV 100
  2       .DNEK........R..E.........D...ND..D..M..S.P    .P.
  3

1  101 EFECPMSPASHRRSRALSPAGYTSPTRVHRDSVSSVSSFTS_YQDIYSRA 149
  2       PM......S..........P .A........I........T...V....
  3                                                      S 1  150 RSRSR_SRALHSSDRHNYSSPPVNAFPSQPSSANSSFTGCSSLGYSSSRN 198
  2       ..S..S..P.Q.......M.AA_TS..... ........A.........
  3       T...__..P..T......V..S_.S.Q...A........S.........T 1  199 RSFSKASGPTQYIFHEEDMNFVDAPTISRVFDEKTMYRNFSSPRGMCLI  247
  2       .....T.AQS..........Y......H................L...
  3       ..Y....AHS..........Y......H............T...L...

1  248 INNEHFEQMPTRNGTKADKDNLTNLFRCMGYTVICKDNLTGRGMLLTIRD 297
  2       ....................I.................E..S...S
  3       ................P....IS........I.H........ .M.....

1  298 FAKHESHGDSAILVILSHGEENVIIGVDDIPISTHEIYDLLNAANAPRLA 347
  2       .GRNDM................... .........VSVNV.............
  3       ...N.T....... ............VSVNV....X...........

1  348 NKPKIVFVQACRGERRDNGFPVLDSVDGVPAFLRRGWDNRDGPLFNFLGC 397
  2       ....L......................SLI................
  3       ....L.........V..............LI.....KG...  .....

1  398 VRPQVQQVWRKKPSQADILIRYATTAQYVSWRNSARGSWFIQAVCEVFST 447
  2       .................M..A.........................L
  3       ....A...............A.........................L 1  448 HAKDMDVVELLTEVNKKVACGFQTSQGSNILKQMPEMTSRLLKKFYFWPE 497
  2       .............................L..............
  3       .........................A.......L............

1  498 __ARN__SAV 503
  2       DRG..__...
  3       __D..RS...

Line 1  C. elegans
Line 2  C. briggsae
Line 3  C. vulgaris
```

FIG. 10

Summary of the experiments to localize ced-3 gene within C40D1

| DNA | ced-3 activity | No. lines |
|---|---|---|
| C48D1 | ++ | 2 |
| C48D1-20 | ++ | 2 |
| C48D1-43 | ++ | 1 |
| pJ40 | ++ | 1 |
| pJ107 | ++ | 1 |
| pJ107del28 & pJ107del34 | ++ | 3 |
| pJ107del12 & pJ107del27 | + | 1 |
| pJ55 & pJ56 | − | 12 |

CLONING SEQUENCING AND CHARACTERIZATION OF TWO CELL DEATH GENES AND USES THEREFOR

RELATED APPLICATION

This application is a continuation of USSN 08/287669, filed Aug. 9, 1994, now abandoned is a continuation-in-part of USSN 07/897,788, entitled "Cloning, Sequencing and Characterization of Two Cell Death Genes and Uses Therefor" by H. Robert Horvitz, Junying Yuan, and Shai Shaham, filed Jun. 12, 1992 now abandoned. The teachings of USSN 07/897,788 are incorporated by reference.

GOVERNMENT FUNDING

Work described herein was supported by grants GM24663 and GM24943 from the U.S. Public Health Service. The U.S. Government has certain rights in the invention.

BACKGROUND

Cell death is a fundamental aspect of animal development. Many cells die during the normal development of both vertebrates (Glucksmann, *Biol. Rev. Cambridge Philos. Soc.* 26:59–86 (1951)) and invertebrates (Truman, *Ann. Rev. Neurosci.* 7:171–188 (1984)). These deaths appear to function in morphogenesis, metamorphosis and tissue homeostasis, as well as in the generation of neuronal specificity and sexual dimorphism (reviewed by Ellis et al., *Ann. Rev. Cell Biol.* 7:663–698 (1991)). An understanding of the mechanisms that cause cells to die and that specify which cells are to live and which cells are to die is essential for an understanding of animal development.

The nematode *Caenorhabditis elegans* is an appropriate organism for analyzing naturally-occurring or programmed cell death (Horvitz et al., *Neurosci. Comment.* 1:56–65 (1982)). The generation of the 959 somatic cells of the adult *C. elegans* hermaphrodite is accompanied by the generation and subsequent deaths of an additional 131 cells (Sulston and Horvitz, *Dev. Biol.* 82:110–156 (1977); Sulston et al., *Dev. Biol.* 100:64–119 (1982)). The morphology of cells undergoing programmed cell death in *C. elegans* has been described at both the light and electron microscopic levels (Sulston and Horvitz, *Dev. Biol.* 82:100–156 (1977); Robertson and Thomson, *J. Embryol. Exp. Morph.* 67:89–100 (1982)).

Many genes that affect *C. elegans* programmed cell death have been identified (reviewed by Ellis et al., *Ann. Rev. Cell Biol.* 7:663–698 (1991)). The activities of two of these genes, ced-3 and ced-4, are required for the onset of almost all *C. elegans* programmed cell deaths (Ellis and Horvitz, *Cell* 44:817–829 (1986)). When the activity of either ced-3 or ced-4 is eliminated, cells that would normally die instead survive and can differentiate into recognizable cell types and even function (Ellis and Horvitz, *Cell* 44:817–829 (1986); Avery and Horvitz, *Cell* 51:1071–1078 (1987); White et al., *Phil. Trans. R. Soc. Lond. B.* 331:263–271 (1991)). Genetic mosaic analyses have indicated that the ced-3 and ced-4 genes most likely act in a cell autonomous manner within dying cells, suggesting that the products of these genes are expressed within dying cells and either are cytotoxic molecules or control the activities of cytotoxic molecules (Yuan and Horvitz, *Dev. Biol.* 138:33–41 (1990)).

SUMMARY OF THE INVENTION

This invention relates to genes shown to be essential for programmed cell death, referred to herein as cell death genes, to their encoded products (RNA and polypeptides), and to antibodies directed against the encoded polypeptides. Methods and probes for identifying and screening for other cell death genes, including those of vertebrates as well as invertebrates, and possibly, microbes and plants, are described. Agents which mimic or affect the activity of cell death genes and methods for identifying these agents are also described. Bioassays which detect the activity of cell death genes and which are useful for identifying cell death genes, for testing the effect of mutations in cell death genes, and for identifying agents which mimic or affect the activity of cell death genes are also provided. This invention further relates to methods for altering (increasing or decreasing) the activity of the cell death genes or their encoded products in cells and, thus, for altering the proliferative capacity or longevity of a cell population or organism.

Specifically, the ced-3 and ced-4 genes of the nematode *C. elegans* have been identified, sequenced, and characterized. These genes have been shown to be required for almost all the programmed cell deaths which occur during development in *C. elegans*. Thus, two cell death genes and their encoded products (RNA, polypeptide) are now available for a variety of uses.

As described herein, the ced-3 and ced-4 genes can be used to identify structurally related genes from a variety of sources. Some of these related genes are likely to also function as cell death genes. Structural comparison of related cell death genes, as well as mutational analysis, can provide insights into functionally important regions or features of cell death genes and gene products. This information is useful in the design of agents which mimic or which alter the activity of cell death genes.

This invention further provides methods and agents for altering (increasing or decreasing) the occurrence of cell death in a cell population or organism. Methods and agents, described herein, which decrease cell death are potentially useful for treatment (therapeutic and preventive) of disorders and conditions characterized by cell deaths, including myocardial infarction, stroke, traumatic brain injury, degenerative diseases (e.g., Huntington's disease, amyotrophic lateral sclerosis, Alzheimer's disease, Parkinson's disease, and Duchenne's muscular dystrophy), viral and other types of pathogenic infection (e.g., human immunodeficiency virus, HIV), aging and hair loss. Methods and agents which increase cell death are also provided and are potentially useful for reducing the proliferation or size of cell populations, such as cancerous cells,, cells infected with viruses (e.g., HIV) or other infectious agents, cells which produce autoreactive antibodies and hair follicle cells. Such methods and agents may also be used to incapacitate or kill undesired organisms, such as pests, parasites, and recombinant organisms.

BRIEF DESCRIPTION OF THE DRAWINGS

FIGS. 1A–1E show the genomic organization and nucleotide sequence (Seq. ID #1) of ced-4 and deduced amino acid sequence (Seq. ID #2). The genomic sequence of the ced-4 region was obtained from plasmid C1OD8-5, which rescues the ced-4 mutant phenotype. Two likely transcriptional start sites are marked with downward arrows. The start of the cDNA is marked with a solid arrowhead. The poitions of eight ced-4 mutations are indicated by upward arrows. Numbers on the sides indicate nucleotide positions, beginning at the start of C10D8-5. Numbers under the amino acid sequence indicate codon poitions. Vertical lines between nucleotides indicate splice junctions.

FIG. 3 shows the sequence similarities between the Ced-4 protein and some calcium-binding proteins. The consensus sequence of the calcium-binding loop is shown at the top. The positions indicated by X, Y, Z, –X, and –Z correspond to vertices of an octahedron. The numbers above the X, Y, Z, –X and –Z correspond to the positions of the residues within the 29 amino acid EF-hand sequence. Amino acids are indicated by the single letter code. O, amino acid with an oxygen-containing side chain. *, non-conserved amino acid. Positions Y, Z and –X can be any amino acid with oxygen-containing side chains. Position X is usually aspartic acid, and position –Z is usually glutamic acid. Conserved amino acids are shown in bold-face. Deviations from the EF-hand consensus sequence are underlined.

FIGS. 4A–4I show the nucleotide sequence (Seq. ID #18) of ced-3 and deduced amino acid sequence (Seq. ID #19). The genomic sequence of the ced-3 region was obtained from plasmid pJ107, which rescues the ced-3 mutant phenotype. The likely translation initiation site is indicated by a solid arrowhead. The SL1 splice acceptor of the RNA is boxed. The positions of 12 ced-3 mutations are indicated. Repetitive elements in the introns are indicated as arrows above the relevant sequence. Numbers on the sides indicate nucleotide positions, beginning with the start of pJ107. Numbers under the amino acid sequence indicate codon positions.

FIG. 5B shows the locations of the mutations relative to the exons (numbered 1–8) and the encoded serine-rich region.

FIG. 7 shows a comparison of the ced-3 proteins of *C. elegans* (line 1) and related nematodes, *C. briggsae* (line 2) and *C. vulgaris* (line 3). The conserved amino acids are indicated by ".". Gaps inserted in the sequence for the purpose of alignment are indicated by "_".

FIG. 10 summarizes experiments to localize ced-3 within C48D1. Restriction sites of plasmid C48D1 and subclone plasmids are shown. ced-3 activity was scored as the number of cell corpses in the head of L1 young animals. ++, the number of cell corpses above 10. +, the number of cell corpses below 10 but above 2. –, the number of cell corpses below 2.

DETAILED DESCRIPTION OF THE INVENTION

The ced-3 and ced-4 genes of *C. elegans* have been shown to be required for almost all programmed cell deaths in *C. elegans* development (Ellis and Horvitz, Cell 44:817–829 (1986)). The present work describes the cloning, sequencing and characterization of these genes. As a result of this work, two genes whose activities are required for cell death, referred to herein as cell death genes, and their encoded products (RNA, polypeptide) are available for a variety of uses. Described below are the cloning and characterization of the *C. elegans* ced-4 and ced-3 genes, methods and probes for identifying structurally related genes, methods for identifying cell death genes from a variety of organisms, methods for identifying agents which mimic or which affect the activity of cell death genes, and methods and agents for altering cell death activity and thus, for altering the occurrence of cell death in a cell population or organism.

The activity of a cell death gene is intended to include the activity of the gene itself and of the encoded products of the gene. Thus, agents and mutations which affect the activity of a gene include those which affect the expression as well as the function of the encoded RNA and protein. The agents may interact with the gene or with the RNA or protein encoded by the gene, or may exert their effect more indirectly.

THE CED-4 GENE

The cloning, sequencing and characterization of the *C. elegans* ced-4 gene are described in Example 1. Genomic clones were obtained from a ced-4 mutant allele generated by transposon tagging. A subclone containing as little as 4.4 kb of wild-type genomic DNA was shown to complement the ced-4 mutant phenotype (see Table 1; tables are located at the end of the Detailed Description).

A 2.2 kb mRNA was identified as the ced-4 transcript. The transcript was shown to be present at normal levels in a ced-3 mutant, suggesting that ced-3 is not a transcriptional regulator of ced-4 gene expression. Furthermore, the 2.2 kb transcript was shown to be expressed primarily during embryogenesis. This is consistent with the observation that 113 of the 131 programmed cell deaths in *C. elegans* are embryonic (Sulston and Horvitz, Dev. Biol. 82:110–156 (1977); Sulston et al., Dev. Biol. 100:64–119 (1983)).

cDNA clones were further obtained and sequenced. Analysis of the cDNA and its encoded product indicates that the putative Ced-4 protein is 549 amino acids in length (FIG. 1; Seq. ID #2) and about 62,877 in relative molecular mass. The Ced-4 protein is highly hydrophilic, with a predicted pI of 5.12; there are no obvious transmembrane regions. The longest hydrophobic region is a segment of 12 amino acids from residues 382 to 393.

Figure 2:
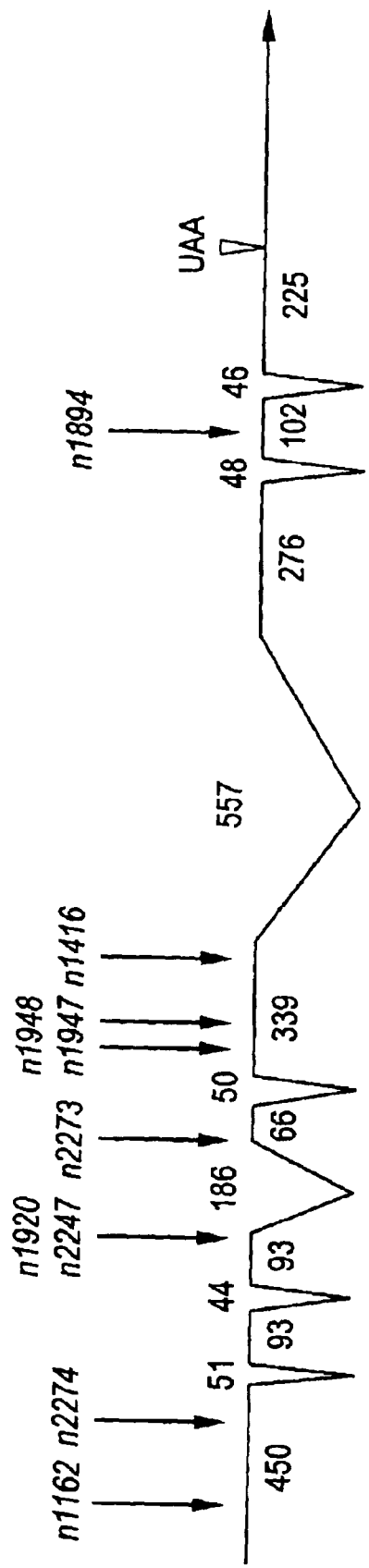
FIG. 2 shows the genomic structure of the ced-4 gene and positions of ced-4 mutations. The sizes of exons and introns are indicated in base pairs (bp). The downward arrows indicate the positions of the Tc4 insertion in the ced-4(nl416) mutant and of eight EMS-induced mutations of ced-4. The arrow pointing right indicates the direction of transcription. The solid arrowhead indicates the translation initiation site. The open arrowhead indicates the ochre termination codon.

Sequence analysis of the ced-4 genomic clone and comparison with the cDNA sequence revealed that the ced-4 gene contains 7 introns with sizes ranging from 44 bp to 557 bp (FIG. 2).

The nucleotide sequences of eight EMS-induced ced-4 mutations were also determined. Of the eight mutations, one results in a single amino acid substitution and the other seven appear to prevent either ced-4 RNA splicing or completion of Ced-4 protein synthesis (FIG. 2 and Table 2). These seven mutations establish the null phenotype of the ced-4 gene, confirming that ced-4 function is not essential for viability.

Two regions of the inferred Ced-4 protein have sequence similarity to known calcium-binding domains (Kretsinger, Cold Spring Harbor Symp. Quant. Biol. 52:499–510 (1987)), suggesting that Ced-4 activity and hence, programmed cell death may be modulated by calcium (see FIG. 3 and Example 1). Calcium has been implicated as an essential mediator of cell death in other organisms under a variety of conditions. For example, extracellular calcium is required for glucocorticoid-induced thymocyte death (Cohen and Duke, *J. Immunol.* 132:38–42 (1984)), for the deaths of adult rat hepatocytes induced by certain toxins in vitro (Schanne et al., *Science* 206:700–702 (1979)), for agonist-induced muscle degeneration in mice (Leonard and Salpeter, *J. Cell Biol.* 82:811–819 (1979)) and for neuronal cell death caused by oxygen deprivation or excitotoxicity (Coyle et al., *Neurosci. Res. Prog. Bull.* 19:331–427 (1981); Choi, *J. Neurosci.* 7:369–379 (1987), Choi, *Trends Neurosci.* 11:465–469 (1988)). It is possible that programmed cell death is initiated during *C. elegans* development by an increase in intracellular calcium, which activates the Ced-4 protein to become cytotoxic. On the other hand, certain cells seem to be protected against cell death by calcium (e.g., Koike et al., *Proc. Natl. Acad. Sci. USA* 86:6421–6425 (1989); Collins et al., *J. Neurosci.* 11:2582–2587 (1991)), suggesting that increases in intracellular calcium levels may inhibit the activity of the Ced-4 protein and thereby prevent programmed cell death.

The level of the ced-4 transcript in eggs is about 20% that of the actin 1 transcript, which is relatively abundant (Edwards and Wood, *Dev. Biol.* 97:375–390 (1983)). This level seems higher than might be expected if ced-4 were expressed only in dying cells, since in an embryo there are usually no more than two or three cells dying at the same time. These considerations suggest that ced-4 might be transcribed not only in dying cells but in other cells as well. Perhaps Ced-4 activity, at least during embryonic development, is regulated at a post-transcriptional level. For example, the Ced-4 protein might have to interact with other proteins or other factors (such as calcium) to cause cell death. Since the ced-3 gene is also essential for programmed cell death in *C. elegans*, one possibility is that the activity of the Ced-4 protein is dependent upon ced-3 function.

THE ced-3 GENE

The cloning, sequencing and characterization of the ced-3 gene are described in Example 2. The ced-3 gene was cloried by mapping DNA restriction fragment length polymorphisms (RFLPs) and chromosome walking. A 7.5 kb fragment of genomic DNA was shown to complement ced-3 mutant phenotypes. A 2.8 kb transcript was further identified. The ced-3 transcript was found to be most abundant in embryos, but was also detected in larvae and young adults, suggesting that ced-3 is not only expressed in cells undergoing programmed cell death.

Figure 5A:
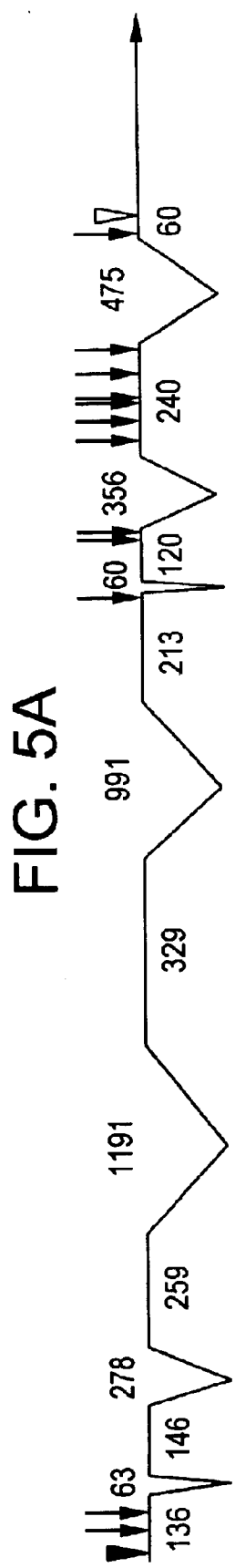
FIG. 5A shows the genomic structure of the ced-3 gene and the location of the mutations. The sizes of the introns and exons are given in bp. The downward arrows indicate the positions of 12 EMS-induced mutations of ced-3. The arrow pointing right indicates the direction of transcription. The solid arrowhead indicates the translation initiation site. The open -arrowhead indicates the termination codon.

A 2.5 kb cDNA corresponding to the ced-3 mRNA was sequenced. The genomic sequence was also determined (FIG. 4; Seq. ID #18) and a comparison with the cDNA sequence revealed that the ced-3 gene has 8 introns which range in size from 54 to 1195 bp (FIG. 5A). The four largest introns as well as sequences 5' of the start codon contain repetitive elements, some of which have been previously characterized in non-coding regions of other *C. elegans* genes such as fem-1 (Spence et al., *Cell* 60:981–990 (1990)), lin-12 (J. Yochem, personnal communication), and myoD (Krause et al., *Cell* 63:907–919 (1990)). The transcriptional start site was also mapped, and the ced-3 transcript was found to be trans-spliced to a *C. elegans* splice leader, SL1.

Twelve EMS-induced ced-3 alleles were also sequenced. Eight of the mutations are missense mutations, two are nonsense mutations, and two are putative splicing mutations (Table 3). The molecular nature of these mutations, together with results of genetic and developmental analyses of nematodes homozygous for these mutations, indicate that, like ced-4, ced-3 function is not essential to viability. In addition, 10 out of the 12 mutations are clustered in the C-terminal region of the gene (FIG. 5B), suggesting that this portion of the encoded protein may be important for activity.

Figure 6:
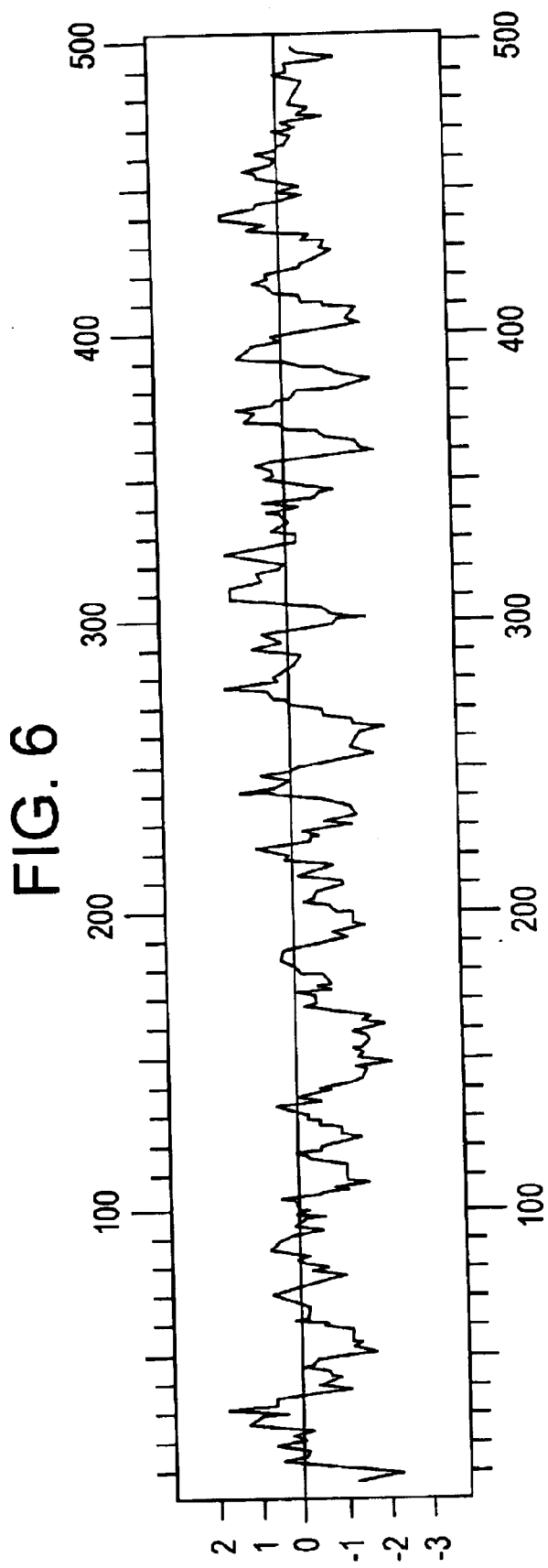
FIG. 6 is a Kyte-Doolittle hydrophobicity plot of the Ced-3 protein.

The ced3 gene encodes a putative protein of 503 amino acids (FIG. 4; Seq. ID #19). The protein is very hydrophilic and no significantly hydrophobic region can be found that might be a transmembrane domain (FIG. 6). One region of the ced-3 protein is very rich in serine. Sequence comparison of two additional ced-3 genes from related nematodes, *C. briggsae* and *C. vulgaris*, suggests that the exact sequence in this serine-rich region may not be important but that the serine-rich feature is (FIG. 7; Seq. ID #19–21). This hypothesis is supported by the analysis of ced-3 mutations: none of 12 EMS-induced ced-3 mutations is in the serine-rich region (FIG. 5B).

The conservation of the serine-rich feature among the ced-3 genes of different nematodes suggests that the serine-rich region may act in semi-specific protein-protein interactions, similar to acid blobs in transcription factors and basic residues in nuclear localization signals. In all these cases, the exact primary sequence is not important.

It is possible that the serine residues in the Ced-3 and Ced-4 proteins may be targets for a Ser/Thr kinase, and that the activity of these proteins may be regulated post-translationally by protein phosphorylation. McConkey et al. (*J. Immunol.*, 145:1227–1230 (1990)) have shown that phorbol esters, which stimulate protein kinase C, can block the death of cultured thymocytes induced by exposure to $Ca^{++}$ ionophores or glucocorticoids (Wyllie, *Nature* 284:555–556 (1980); Wyllie et al., *J. Path.* 142:67–77 (1984)). It is possible that protein kinase C may inactivate certain cell death proteins by phosphorylation, and thus, inhibit cell death and promote cell proliferation. Several agents that can elevate cytosolic cAMP levels have been shown to induce thymocyte death, suggesting that protein kinase A may also play a role in mediating thymocyte death. Further evidence suggests that abnormal phosphorylation may play a role in the pathogene,sis of certain cell-degenerative diseases. For example, abnormal phosphorylation of the microtubule-associated protein Tau is found in the brains of Alzheimer's disease and Down's syndrome patients (Grundke-Iqbal et al., *Proc. Natl. Acad. Sci. USA* 83:4913–4917 (1986); Flament et al., *Brain Res.* 516:15–19 (1990)). Thus, it is possible that phosphorylation may have a role in regulating programmed cell death in *C. elegans*. This is consistent with the fairly high levels of ced-3 and ced-4 transcripts which suggest that transcription regulation alone may be insufficient to regulate programmed cell death.

STRUCTURALLY AND FUNCTIONALLY RELATED GENES

As a result of the work described herein, it is possible to identify genes which are structurally and/or functionally related to ced-3 or ced-4. Such genes are expected to be found in a variety of organisms, including vertebrates (e.g., mammals and particularly humans), invertebrates (e.g., insects), microbes (e.g., yeast) and possibly plants. Structurally related genes refer herein to genes which have some structural similarity to the nucleotide sequences (genomic or cDNA) of one or both of the ced-3 or ced-4 genes, or whose encoded proteins have some similarity to one or both of the amino acid sequences of the Ced-3 or Ced-4 proteins. Functionally related genes refer to genes which have similar activity to that of ced-3 and ced-4 in that they cause cell death. Such genes can be identified by their ability to complement ced-3 or ced-4 mutations in bioassays, as described below.

Previous studies are consistent with the hypothesis that genes similar to the *C. elegans* ced-3 and ced-4 genes may be involved in the cell deaths that occur in both vertebrates and invertebrates. Some vertebrate cell deaths share certain characteristics with the programmed cell deaths in C. elegans that are controlled by ced-3 and ced-4. For example, up to 14% of the neurons in the chick dorsal root ganglia die immediately after their births, before any signs of differentiation (Carr and Simpson, *Dev. Brain Res.* 2:57–162 (1982)). Genes like ced-3 and ced-4 could well function in this class of vertebrate cell death. In addition, genes related to ced-3 and ced-4 could function in many other types of vertebrate cell death processes, including those involving cells that die long after their births and those that die as a result of stress (e.g., oxygen deprivation) or disease.

Genetic mosaic analysis has suggested that the ced-3 and ced-4 genes act within cells that undergo programmed cell death, rather than through cell-cell interactions or diffusible factors (Yuan and Horvitz, *Dev. Biol.* 138:33–41 (1990)). Many cell deaths in vertebrates seem different in that they appear to be controlled by interactions with target tissues. For example, it is thought that a deprivation of target-derived growth factors is responsible for vertebrate neuronal cell deaths (Hamburger and Oppenheim, *Neurosci. Comment.* 1:39–55 (1982)); Thoenen et al., in: *Selective Neuronal Death*, Wiley, N.Y., 1987, Vol. 126, pp. 82–85). However, even this class of cell death could involve genes like ced-3 and ced-4, since pathways of cell death involving similar genes and mechanisms might be triggered in a variety of ways. Supporting this idea are several in vitro and in vivo studies which show that the deaths of vertebrate as well as invertebrate cells can be prevented by inhibitors of RNA and protein synthesis, suggesting that activation of genes is required for these cell deaths (Martin et al., *J. Cell Biol.* 106:829–844 (1988); Cohen and Duke, *J. Immunol.* 132:38–42 (1984); Oppenheim and Prevette, *Neurosci. Abstr.* 14:368 (1988); Stanisic et al., *Invest. Urol.* 16:19–22 (1978); oppenheim et al., *Dev. Biol.* 138:104–113 (1990); Fahrbach and Truman, in: *Selective Neuronal Death, Ciba Foundation Symposium*, 1987, No. 126, pp. 65–81). It is possible that the genes induced in these dying vertebrate and invertebrate cells are cell death genes similar to the *C. elegans* genes ced-3 and ced-4.

Also supporting the hypothesis that cell death in *C. elegans* is mechanistically similar to cell death in vertebrates is the observation that the protein product of the *C. elegans* gene ced-9 is similar in sequence to the human protein Bcl-2. ced-9 has been shown to prevent cells from undergoing programmed cell death during nematode development by antagonizing the activities of ced-3 and ced-4 (Hengartner, et al., *Nature* 356:494–499 (1992)). The bcl-2 gene has also been implicated in protecting cells against cell death. It seems likely that the genes and proteins with which ced-9 and bcl-2 interact are similar as well.

Genes which are structurally related to ced-3 or ced-4 are likely to also act as cell death genes. Structurally related genes can be identified by any number of detection methods which utilize a defined nucleotide or amino acid sequence or antibodies as probes. For example, nucleic acid (DNA or RNA) containing all or part of the ced-3 or ced-4 gene can be used as hybridization probes or as polymerase chain reaction (PCR) primers. Degenerate oligonucleotides derived from the amino acid sequence of the Ced-3 or Ced-4 proteins can also be used. Nucleic acid probes can also be based on the consensus sequences of conserved regions of genes or their protein products. In addition, antibodies, both polyclonal and monoclonal, can be raised against the Ced-3 and/or Ced-4 proteins and used as immunoprobes to screen expression libraries of genes.

One strategy for detecting structurally related genes in other organisms is to initially probe animals which are taxonomically closely related to the source of the probes, for example, probing other worms with a ced-3 or ced-4 probe. Closely related species are more likely to possess related genes or gene products which are detected with the probe than more distantly related-organisms. Sequences conserved between ced-3 or ced-4 and these new genes can then be used to identify similar genes from less closely related species. Furthermore, these new genes provide additional sequences with which to probe the molecules of other animals, some of which may share conserved regions with the new genes or gene products but not with ced-3, ced-4, or their gene products. This strategy of using structurally related genes in taxonomically closer organisms as stepping stones to genes in more distantly related organisms can be referred to as walking along the taxonomic tree.

Groups of structurally related genes, such as those obtained by using the above-described strategy, can be referred to as gene families. Comparison of members within a gene family, or their encoded products, may indicate functionally important features of the genes or their gene products. Those features which are conserved are likely to be significant for activity. Such conserved sequences can then be used both to identify new members of the gene family and in drug design and screening. For example, as described in Example 2, genes similar to ced-3 from two other species of nematodes (*C. briggsae* and *C. vulgaris*) were identified and characterized. Serine-rich regions were found in the polypeptides encoded by all three genes. Although the sequence of the serine-rich region was not well conserved, the number of serines was conserved, suggesting that the serine-rich feature, but not the exact sequence of the serine-rich region, is significant for function.

Functionally important regions can also be identified by mutagenesis. For example, inactivating mutations of ced-3 were found to cluster within a region near the COOH-terminus (FIG. 5B), suggesting that this region is a functionally important domain of the Ced-3 protein. Further mutational analyses can be carried out on the ced-3 and ced-4 genes; mutants with novel properties, as well as other regions important for activity, may be discovered. Mutations and other alterations can be accomplished using known methods, such as in vivo and in vitro mutagenesis (see, e.g., Ausubel et al. (eds.), *Current Protocols in Molecular Biology*, Greene Publishing Associates and Wiley-Interscience, New York).

BIOASSAYS AND AGENTS WHICH AFFECT THE ACTIVITY OF CELL DEATH GENES

This invention further provides bioassays which detect the activity of cell death genes. The bioassays can be used to identify novel cell death genes, to identify mutations which affect the activity of cell death genes, to identify genes which are functionally related to known cell death genes, such as ced-3 or ced-4, to identify genes which interact with cell death genes, and to identify agents which mimic or affect the activity of cell death genes (e.g., agonists and antagonists). For example, the bioassays can be used to screen expression gene libraries for cell death genes from other organisms.

In this bioassay, genes or agents are introduced into nematodes to test their effect on cell deaths in vivo. Wild-type, mutant, and transgenic nematodes can be used as appropriate for the effect being tested. In one embodiment of this bioassay, transgenic nematodes are produced using a candidate cell death gene, a mutant cell death gene, or genes from an expression library, to observe the effect of the transgene on the pattern of programmed cell deaths during development of the nematode. For example, a gene which is structurally related to ced-3 can be used to produce a transgenic animal from a mutant nematode which underexpresses or expresses an inactivated ced-3 gene to see if the related gene can complement the ced-3 mutation and is thus, functionally as well as structurally related to ced-3. cDNA or genomic libraries can be screened for genes having cell death activity. Genes which interact with cell death genes to enhance or suppress their activity can also be identified by this method.

In another embodiment of the bioassay, wild-type, mutant, or transgenic nematodes are exposed to or administered peptides and other molecules in order to identify agents that mimic, increase, or decrease the activity of a cell death gene. For example, wild-type animals can be used to test agents that inactivate or antagonize the activity of ced-3 or ced-4 and hence, decrease cell deaths, or that activate or enhance ced-3 or ced-4 activity and increase cell deaths. Mutant animals in which ced-3 or ced-4 is inactivated can be used to identify agents or genes which mimic ced-3 or ced-4 in causing cell deaths. Mutant animals in which ced-3 or ced-4 is overexpressed or constitutively activated can similarly be used to identify agents that prevent ced-3 or ced-4 from causing cell death. Transgenic animals in which a wild-type or mutant form of an exogenous cell death gene causes excess cell deaths due to overexpression or hyperactivity can be used to identify agents that inactivate or inhibit the activity of the transgene. Similarly, transgenic animals in which a wild-type or mutant form of an exogenous cell death gene is underexpressed or inactive can be used to identify agents that activate or increase its activity. Test molecules can be introduced into nematodes by microinjection, diffusion, ingestion, shooting with a particle gun, or other method.

Mutated cell death genes with novel properties may be identified by the above bioassay. For example, constitutively activated or hyperactive cell death genes may be isolated which may be useful as agents to increase cell deaths. Mutations may also produce genes which do not cause cell death but which antagonize the activity of the wild-type gene.

Agents can be obtained from traditional sources, such as extracts (e.g., bacterial, fungal or plant) and compound libraries, or by newer methods of rationale drug design. Information on functionally important regions of the genes or gene products, gained by sequence and/or mutational analysis, as described above, may provide a basis for drug design. The activity of the agents can be verified both by in vivo bioassays using nematodes which express various forms of ced-3, ced-4, or related genes, as described above, and by in vitro systems, in which the genes are expressed in cultured cells, or in which isolated or synthetic gene products are tested directly in biochemical experiments. The agents may include all or portions of the ced-3, ced-4, or related genes, mutated genes, and all or portions of the gene products (RNA, including antisense RNA, and protein), as well as nucleic acid or protein derivatives, such as oligonucleotides and peptides, peptide and non-peptide mimetics, and agonists and antagonists which affect the activity or expression of the cell death genes. The agents can also be portions or derivatives of genes or gene products which are not cell death genes but which regulate the expression of, interact with, or otherwise affect the function of cell death genes or gene products.

USES OF THE INVENTION

Using the above-described probes and bioassays, the identification and expression of ced-3, ced-4 or related cell death genes in cultured cells, tissues, and whole organisms can be studied to gain insights into their role in development and pathology in various organisms. For example, the detection of abnormalities in the sequence, expression, or activity of a cell death gene or gene product may provide a useful diagnostic for diseases involving cell deaths.

This invention further provides means of altering or controlling the activity of a cell death gene in a cell, and, thus, affecting the occurrence of cell death. Activity of the cell death gene can be altered to either increase or decrease cell deaths in a population of cells and, thus, affect the proliferative capacity or longevity of a cell population, organ, or entire organism.

Agents which act as inactivators or antagonists of the activity of ced-3, ced-4, or other cell death genes can be used to prevent or decrease cell deaths. Such agents are useful for treating (i.e., for both preventive and therapeutic purposes) disorders and conditions characterized by cell deaths, including neural and muscular degenerative diseases, stroke, traumatic brain injury, myocardial infarction, viral (e.g., HIV) and other types of pathogenic infections, as well as cell death associated with normal aging and hair loss. The agent can be delivered to the affected cells by various methods appropriate for the cells or organs being treated, including gene therapy. For example, anti-sense RNA encoded by all or a part of a cell death gene which is complementary to the mRNA can be delivered to a population of cells by an appropriate-vector, such as a retroviral or adenoviral vector, or an antagonist of cell death activity can be infused into a wound area to limit tissue damage.

Methods and agents which cause or increase cell deaths are also useful, for example, for treating disorders characterized by an abnormally low rate or number of cell deaths or by excessive cell growth, such as neoplastic and other cancerous growth. Such methods and agents are also useful for controlling or eliminating cell populations, such as cells infected with viruses (e.g., HIV) or other infectious agents, cells producing autoreactive antibodies, and hair follicle cells. In addition, methods and agents which increase cell death can be used to kill or incapacitate undesired organisms, such as pests, parasites and genetically engineered organisms. All or portions of ced-3, ced-4, or related cell death genes, active mutant genes, their encoded products, agents which mimic the activity of cell death genes, and activators and agonists of cell death genes can be used for this purpose.

For example, cell death genes can be used to kill cells infected with the human immunodeficiency virus (HIV), and thus, prevent or limit HIV infection in an individual. A recombinant gene can be constructed, in which a cell death gene is under the control of a viral promoter which is specifically activated by a viral protein; the recombinant gene is introduced into HIV infected cells. HIV-infected cells containing the viral activator protein would express the cell death gene product and be killed, and uninfected cells would be unaffected.

Alternatively, an antagonist of ced-3 or ced-4 activity (such as antisense RNA) can be expressed under the control of a viral-specific promoter and in this way, be used to prevent the cell death associated with viral (e.g., HIV) infection.

In another example, cell death genes can be used as suicide genes for biological containment purposes. Genetic engineering of suicide genes into recombinant organisms has been reported in bacteria (*Genetic Engineering News*, Nov. 1991, p. 13): suicide genes were engineered to be expressed simultaneously with the desired recombinant gene product so that the recombinant bacteria die upon completion of their task. The present invention provides suicide genes which are useful in a variety of organisms in addition to bacteria, for example in insects, fungi, and transgenic rodents. Suicide genes can be constructed by placing the coding sequence of an exogenous cell death gene or an agonist of an endogenous cell death gene of the organism in an expression vector suitable for the organism.

In addition, agents which increase cell death are useful as pesticides (e.g., anthelminthics, nematicides). For example, many nematodes are human, animal, or plant parasites. ced-3, ced-4, or other nematode cell death genes, their gene products, mimetics, and agonists can be used to reduce the nematode population in an area, as well as to treat individuals already infected with the parasite or protect individuals from infection. A transgenic plant or animal carrying a constitutively activated ced-3 gene, ced-4 gene, or other cell death gene specific to nematodes can be protected from nematode infection in this way.

The subject invention will now be illustrated by the following examples, which are not intended to be limiting in any way.2

EXAMPLE 1

Cloning, Sequencing and Characterization of the CED-4 Gene

Materals and Methods
General Methods and Strains

Techniques used for the culturing of *C. elegans* were essentially as described by Brenner (*Genetics* 77:71–94 (1974)). All strains were grown at 20° C. DNA was prepared from worms grown on Petri dishes containing agarose seeded with *E. coli* strain HB101. RNA was prepared from mass cultures grown in liquid. Usually, the bacterial pellet from a 2 L overnight culture of *E. coli* HB101 grown in superbroth (12 g Bacto-tryptone, 24 g yeast extract, 8 ml 50% glycerol, 900 ml $H_2O$; after autoclaving, 100 ml 0.17 M $KH_2PO_4$ and 0.72 $K_2HPO_4$ were added) was resuspended in 500 ml S basal medium (Brenner, 1974 supra), and worms were added from one or two 10 cm Petri dishes in which the bacterial lawns had just been consumed. Worms were harvested about 4–5 days later by centrifugation and washed in M9 buffer (Brenner, 1974 supra). The yield was about 5–10 ml of packed worms.

Nomarski differential interference contrast microscopy was used to examine individual cells in living nematodes (Sulston and Horvitz, *Dev. Biol.* 82:110–156 (1977)). Methods for scoring the Ced phenotype of ced-1, ced-4 and ced-1; ced-4 double mutants have been described by Ellis and Horvitz, (*Cell* 44:817–829 (1986)) and by Yuan and Horvitz, (*Dev. Biol.* 138:33–41 (1990)).

The wild-type parent of all mutant strains used in these experiments was *C. elegans* variety Bristol strain N2 (Brenner, 1974 supra). The genetic markers used are listed below. These markers have been described (Brenner, 1974 supra; Hodgkin et al., in: *The Nematode Caenorhabditis elegans*, Wood and the Community of *C. elegans* Researchers (eds.), Cold Spring Harbor Laboratory, N.Y., 1988, pp. 491–584; Finney et al., *Cell* 55:757–769 (1988)). The strain TR679 carries the mutator mut-2(r459) (Collins et al., *Nature* 328:726–728 (1987)). The ced-4 alleles n1894, n1920, n1947, n1948, n2247, and n2273 were characterized in the present work. Genetic nomenclature follows the standard system for *C. elegans* (Horvitz et al., *Mol. Gen. Genet.* 175:129–133 (1979)):

LG I: ced-1(e1735), unc-54(r323)
LG III: unc-86(n1351), ced-4(n1162, n1416, n1894, n1920, n1947, n1948, n2247, n2273, n1416 n1712, n1416 n1713), unc-79(e1068), dpy-17(e164)
LG IV: unc-31(e928), ced-3(n717)
LG V: egl-1(n986), unc-76(e911)

GENOMIC LIBRARIES

A 4–6 kb size-selected phage library was constructed from ced-4(n1416) DNA as follows. Genomic DNA was digested with HindIII and run on a low-melting agarose gel. DNA migrating within the 4–6 kb size range was excised, and the low-melting agarose was removed by phenol extraction and precipitation (Maniatis et al., *Molecular Cloning: A Laboratory Manual*, Cold Spring Harbor Laboratory (1983)). These DNA fragments were ligated to HindIII-digested DNA from phage ANM1149 (Murray, *Phage Lambda and Molecular Cloning*, Cold Spring Harbor Laboratory, 1983, pp. 395–432). The product DNA was packaged with packaging extract from Promega. This library had a total of 140,000 plaque-forming units (pfu), of which 70% were recombinants, as estimated from the ratio of pfu on bacteria C600hfl and C600.

The phage genomic library (provided by J. Sulston) was prepared by partial digestion of wild-type C. elegans genomic DNA with Sau3A and cloning into the BamHI site of phage vector λ2001 (Karn et al., *Gene* 32:217–224 (1984)).

TC4 PROBE

The Tc4 probe used for cloning the ced-4 gene and for Southern blots was Tc4-n1351, which contains a Tc4 element isolated from an unc-86(n1351) mutant strain (Finney et al., *Cell* 55:757–769 (1988); Yuan et al., *Proc. Natl. Acad. Sci. USA* 88:3334–3338 (1991)). DNA was labelled with $^{32}P$ using either the nick-translation procedure described by Maniatis et al. (1983 supra) or the oligo-labelling procedure described by Feinberg and Vogelstein (*Anal. Biochem*, 132:6–13 (1983)).

RNA PREPARATION, NORTHERN BLOT AND PRIMER EXTENSION

Total *C. elegans* RNA was extracted using guanidine isothiocyanate (Kim and Horvitz, *Genes & Dev.* 4:357–371 (1990)). Poly(A)$^+$ RNA was selected from total RNA by a poly(dT)-column (Maniatis et al., 1983 supra). To prepare stage-synchronized animals, eggs were obtained from gravid *C. elegans* adults grown at 20° C. in liquid culture. A 5–10 ml sample of animals was treated with 50 ml of NaOCl/NaOH solution (10 ml NaOCl, 1 g NaOH, 40 ml $H_2O$) for about 10 minutes with vortexing until the adults were dissolved. Eggs were centrifuged and washed three times with M9 buffer. Isolated eggs were allowed to hatch in S basal medium without food for 14 hours at 20° C. with shaking. L1 larvae were collected by low-speed centrifugation after growth on *E. coli* HB101 for 2 hours, L2 larvae after 12 hours, L3 larvae after 24 hours, L4 larvae after 36 hours and adults after 48 hours. Northern blot analysis using DNA probes was performed essentially as described by Meyer and Casson (*Genetics* 106:29–44 (1986)), except that RNA was transferred from the gel to the Gene Screen filter (DuPont, Wilmington, Del.) by capillary action.

Quantitation of ced-4 expression during embryonic development was done by hybridizing two duplicate northern blots with ced-4 cDNA clone SK2-2 and with a genomic DNA clone for the actin 1 gene, pW-16-210, which hybridizes to the 3' untranslated region of the actin 1 transcript (Krause and Hirsh, in: *Molecular Biology of the Cytoskeleton*, Borisy et al. (eds.), Cold Spring Harbor Laboratory, 1984, pp. 287–292). The two probes were of the same specific activity ($4 \times 10^8$ counts/minute/µg). The emission of β particles from the ced-4 and actin 1 bands was counted using a β counter (Betagen, Waltham, Mass.). The readings were 7.7 counts/minute for the actin 1 band and 1.4 counts/minute for the ced-4 band.

The primer extension protocol was that of Sambrook et al. (*Molecular Cloning: A Laboratory Manual*, 2nd edition, Cold Spring Harbor Laboratory, 1989, pp. 7.79–7.83), using the primer ATTGGCGATCCTCTCGA (Seq. ID #22). To define the lengths of the reaction products, a sequencing reaction using this primer and C10D8-5 as template was run adjacent to the product of the primer extension reaction in the sequencing gel.

DIRECTION OF TRANSCRIPTION

The direction of transcription was determined by hybridizing northern blots with single-stranded RNA probes. The Bluescribe plasmid containing the insert pn1416 was linearized by digestion with either BamHI or HindIII, which cleaved at one or the other end of the insert. The linearized product was transcribed using T3 or T7 RNA polymerase, respectively, generating RNA from each strand. These RNA products were used to probe Northern blots according to a protocol developed by Z. Liu and V. Ambros: Filters were prehybridized in 50% formamide, 50 mM sodium phosphate (pH 6.5), 5×SSC, 8×Denhardt's, 0.5% SDS, 250 µg/ml salmon sperm DNA and then hybridized with probe at 55° C. and washed in 4×SSC, 0.1% SDS at 60° C. 3 times for 20 minutes each and then in 2×SSC, 0.1% SDS once at 60° C. for 20 minutes. Northern blot experiments showed that the single-stranded RNA probe transcribed by T3 RNA polymerase hybridized to the 2.2 kb ced-4 mRNA, while the probe made by T7 RNA polymerase did not. This result indicates that the direction of the transcription is from the BamHI site toward the HindIII site of pn1416.

DETERMINATION OF DNA SEQUENCE

For determining DNA sequences, serial deletions were made according to Henikoff (*Gene* 28:351–359 (1984)). DNA sequences were determined using Sequenase and protocols obtained from US Biochemicals (Cleveland, Ohio). The ced-4 DNA sequence was confirmed by sequencing both strands of cDNA and genomic DNA clones.

CLONING OF THE COSMID FRAGMENT C10D8-5

The cosmid C10D8 was digested with EcoRI. Two EcoRI fragments of 2.2 kb (r5) and 2.4 kb (r7), both of which hybridized to a mixture of ced-4 CDNA subclones SK2-1 and SK2-2, were isolated. r7, which hybridized to SK2-1, which contains the 3' half of ced-4 cDNA clone SK2, was cloned into the EcoRI site of plasmid pBSKII (Stratagene). The EcoRI site at the 3' end of r7 was deleted by digesting with StyI, which cut once at 0.2 kb from the 3' end of the insert, and SalI, which cut once in the polylinker, and then religating. The deleted r7 plasmid was linearized with EcoRI and ligated with EcoRI-digested r5, which hybridized to Sk2-2, the 5' half of ced-4 cDNA SK2. Clones were analyzed for the correct orientation of the r5 insert based on the cDNA restriction map. One such correctly oriented clone was named C10D8-5.

MICROINJECTION AND TRANSFORMATION

The procedure for microinjecting DNA into the gonad to obtain germline transformants was basically that of Fire (*EMBO J.* 5:2673–2680 (1986)) with modifications introduced by J. Sulston. Cosmid DNA to be injected was purified twice using CsCl-gradient centrifugation (Maniatis et al., 1983 supra). Plasmid DNA to be injected was prepared by alkaline minipreps (Maniatis et al., 1983 supra). DNA was treated with RNAase A (37° C., 30 minutes) and then with proteinase K (55° C., 30 minutes), extracted with phenol and then chloroform, precipitated twice (first in 0.3 M sodium acetate and then in 0.1 M potassium acetate, pH 7.2), and resuspended in 5 ul of injection buffer (Fire, 1986 supra). DNA concentrations used for injection were 0.1–1.0 mg/ml.

All transformation experiments used a ced-1; ced-4 (n1162); unc-31 strain as the recipient. The expression of the Ced-4 phenotype was quantified by counting the number of cell corpses in the heads of young L1 animals. The cosmid C10D8 or plasmid subclones of C10D8 were mixed with cosmid C14G10, which contains the wild-type unc-31(+) gene, at a ratio of 2:1 or 3:1 to increase the likelihood that a phenotypically non-Unc transformant would contain the cosmid or plasmid being tested. Generally, 20–30 animals were injected in one experiment. Non-Unc F1 progeny of injected animals were isolated three to four days later. About 1/2 to 1/3 of the non-Unc progeny transmitted the non-Unc phenotype to their progeny and could be established as lines of transformants. Young L1 non-Unc progeny of such non-Unc transformants were examined using Nomarski optics to determine the number of cell corpses present in the heads.

CED-4 FUSION AND ANTIBODY PREPARATION

To express a Ced-4 fusion protein in *E. coli*, a clone containing both the 5' and 3' halves of the ced-4 cDNA (SK2-2 and SK2-1) in the expression vector pET-5a (Rosenberg et al., *Gene* 56:125–135 (1987)) was constructed. The fusion protein expressed by this vector was expected to include 11 amino acids of phage T7 gene 10 protein, 5 amino acids of linker and the 546 amino acids encoded by ced-4 cDNA SK2. The pJ76 plasmid, which encodes this fusion protein, was transformed into bacterial strain BL21. ced-4 fusion protein was produced by this transformed strain, as expected, and subjected to electrophoresis on a polyacrylamide gel. A band, with mobility equivalent to about $64 \times 10^3$ Mr, specific to the transformed strain was exercised and used to immunize three rabbits. Sera from all three rabbits tested positive on western blots (Towbin et al., *Proc. Natl. Acad. Sci. USA* 76:4350–4354 (1979)). These sera were purified using immunoblots (Harlow and Lane, *Antibodies: A Laboratory Manual*, Cold Spring Harbor Laboratory, 1988).

RESULTS

Cloning of the ced-4 Gene by Transposon Tagging

The ced-4 allele n1416 in the *C. elegans* strain TR679 was isolated, which carries the mutator mut-2(r459) and shows an elevated frequency of transposition elements (Collins et al., *Nature* 328:72614 728 (1987); Yuan et al., *Proc. Natl. Acad. Sci. USA* 88:3334–3338 (1991)). The ced-4(n1416) mutation is closely linked to a newly transposed copy of the *C. elegans* transposon Tc4 (Yuan et al., 1991 supra). Using Tc4 as a probe, this novel Tc4 element and its flanking region was cloned as a 5 kb HindIII fragment from a 4–6 kb size-selected ced-4(n1416) genomic phage library. A 3 kb adjacent to this Tc4 element was isolated by digesting the 5 kb HindIII fragment with BamHI. This 3 kb fragment, called pn1416, was cloned into the Bluescribe M13+ plasmid vector (Stratagene).

When used as a probe on Southern blots, pn1416 hybridized to a 3.4 kb HindIII fragment in DNA of wild-type (strain N2) and two non-Ced revertants of ced-4(n1416), ced-4(n1416 n1712) and ced-4(n1416 n1713) (Yuan and Horvitz, *Dev. Biol.* 138:33–41 (1990)), and a 5 kb HindIII fragment in ced-4(n1416) animals. The hybridizing band in ced-4(n1416) DNA is 1.6 kb larger than that of the wild-type or the revertants, indicating that an insertion of this size is present in the ced-4(n1416) strain and is deleted in both revertants. These observations indicate that the Tc4 insertion in ced-4(n1416) animals is responsible for their Ced-4 mutant phenotype and suggest that pn1416 contains at least part of the ced-4 gene.

To isolate additional genomic DNA from the region of this Tc4 insertion, pn1416 was used to probe a *C. elegans* Bristol N2 genomic DNA phage library. Five phage clones with inserts of 10 to 15 kb were isolated and shown to share a 3 kb BamHI-HindIII fragment that hybridized to pn1416. These phage clones were used to identify cosmids that hybridized to them and that were members of a 600 kb contig of overlapping cosmids (Coulson et al., *Proc. Natl. Acad. Sci. USA* 83:7821–7825 (1986)). By using the phage clones as probes to hybridize to Southern blots, a cosmid C10D8 was identified as containing all regions of genomic DNA present in all five phage clones and in pn1416.

The ced-4 Mutant Phenotype Can Be Rescued by a 4.4 kb DNA Fragment

To identify ced-4(+) DNA capable of complementing the Ced-4 mutant phenotype, the cosmid C10D8 was injected into the oocytes of ced-4(n1162) animals. To facilitate the identification of transgenic animals, a mutation in the unc-31 gene, which affects locomotion, was included as a marker for co-transformation (Kim and Horvitz, *Genes & Dev.* 4:357–371 (1990)). Cosmid C14G10, which contains the wild-type allele of unc-31 and does not have Ced-4-rescuing activity was coinjected with cosmid C10D8 into ced-1 (e1735); unc-31(e928); ced-4(n1162) animals. The ced-1 mutation was included to facilitate the scoring of the ced-4 mutant phenotype (Ellis and Horvitz, *Cell* 44:817–829 (1986)). Specifically, when a cell undergoes programmed cell death in *C. elegans*, its corpse is quickiy engulfed and destroyed by a neighboring cell (Robertson and Thomson, *J. Embryol. Exp. Morph.* 67:89–100 (1982); Sulston et al., *Dev. Biol.* 100:64–119 (1983)). A ced-1 mutation prevents this engulfment, allowing the cell corpse to remain intact (Hedgecock et al., *Science* 220:1277–1280 (1983)). Thus, in a first or second stage (L1 or L2) ced-1 mutant larva, many cell corpses are present and can be easily visualized using Normaski optics. ced-4 mutations prevent cell death and the appearance of these corpses. Thus, suppression of the Ced-4 mutant phenotype by a wild-type ced-4 gene can be observed and readily quantified in a ced-1 mutant background based on an increase in the number of visible cell corpses.

From one such microinjection experiment, three non-Unc animals rescued for the Unc-31 mutant phenotype were picked from among the F1 progeny, and from one of them a line of non-Unc transformants was obtained. No true-breeding non-Unc animals could be isolated from this line: about 25% of the progeny of all non-Unc, animals were Unc. Since no inviable zygotes were observed among the progeny of these non-Unc animals, this transformant did not carry a recessive lethal insertion mutation. Rather, it seems likely that the injected DNA was maintained as an extrachromosomal array that was segregated to only some gametes, as has been reported previously for many other *C. elegans* transgenic strains (e.g., Stinchcomb et al., *Mol. Cell Biol.* 82:110–156 (1985); Fire, *EMBO J.* 5:2673–2680 (1986); Way and Chalfie, *Cell* 54:5–16 (1988)). This putative extrachromosomal array was named nEx1. Young L1 progeny of nEx1-containing animals were examined using Nomarski optics for the Ced-4 phenotype.

Young L1 ced-1 animals have an average of 23 cell corpses in the head, while ced-1(e1735); ced-4(n1162) animals have an average of 0.6 cell corpses (Ellis and Horvitz, *Cell* 44:817–829 (1986)). Young L1 ced-1; ced-4(n1162); nEx1 animals had an average of nine cell corpses in the head. These results indicate that cosmid C10D8 restored significant, but not total, ced-4(+) activity in the transformants.

To delineate the ced-4 gene within C10D8, various subclones of C10D8 were injected into ced-4 mutant animals and tested for their ability to rescue the Ced-4 mutant phenotype (Table 1). The smallest subclone plasmid that could rescue the ced-4 phenotype as effectively as cosmid C10D8 was a 4.4 kb fragment, called C10D8-5. C10D8-5 and the unc-31(+)-containing cosmid C14G10 were coinjected into ced-1; unc-31; ced-4(n1162) animals. Two lines of non-Unc transformants were isolated. Since these animals continued to segregate Unc animals and did not produce inviable zygotes, both appeared to carry extrachromosomal arrays, which were designated nEx7 and nEx8. Young L1 animals from these transformant strains had an average of 11.5 cell corpses in their heads, indicating that plasmid C10D8-5 restored ced-4(+) activity as well as did cosmid C10D8 (Table 1).

IDENTIFICATION OF A CED-4 TRANSCRIPT

Figure 8:
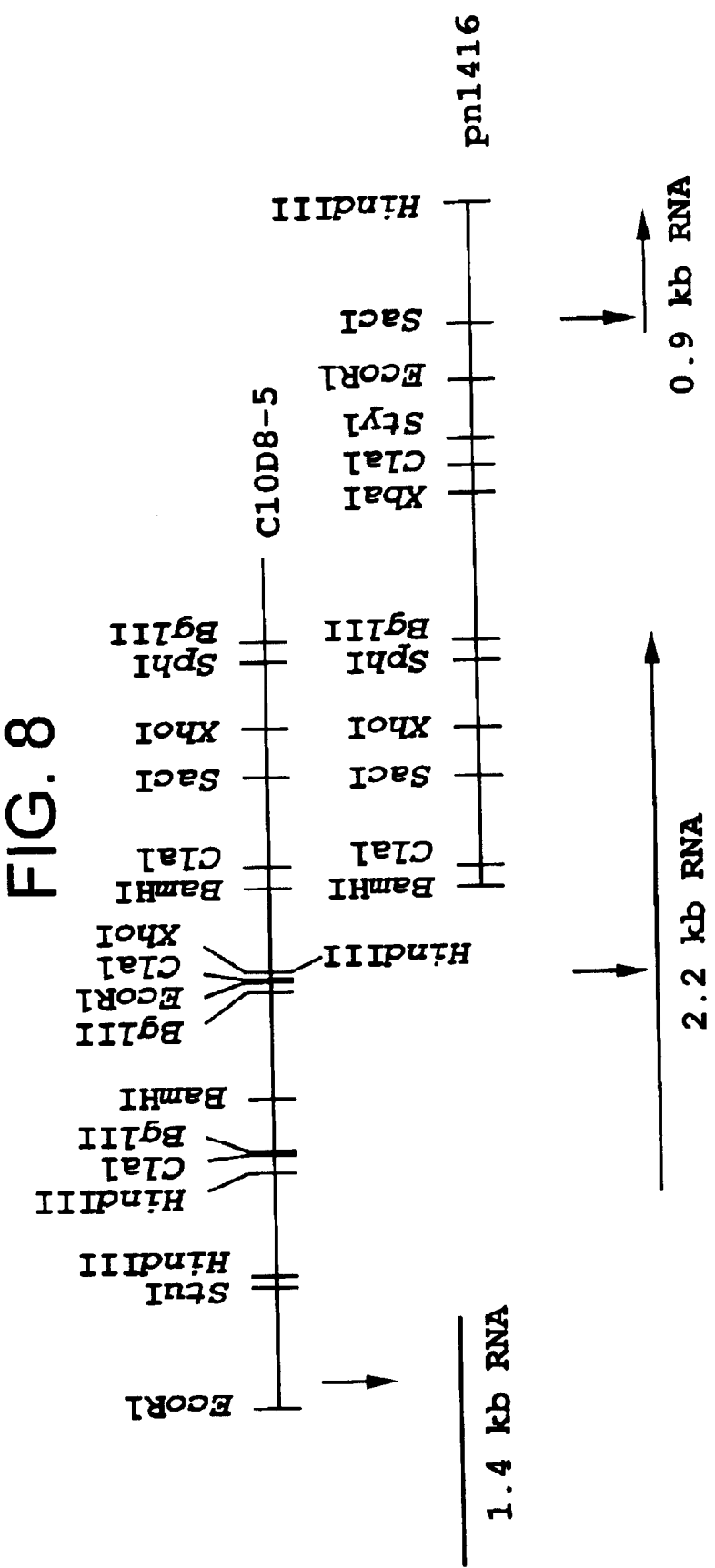
FIG. 8 shows a restriction site map of the ced-4 region and the relative positions of plasmid C10D8-5, plasmid insert pn1416, and three transcripts encoded by the region.

Restriction sites of plasmid C10D8-5 (which can rescue the Ced-4 phenotype) and pn1416 (which contains sequences adjacent to the Tc4 insertion site) were mapped. C10D805 was found to overlap with 2 kb of sequence in pn1416, including the Tc4 insertion site (FIG. 8).

In Northern blot experiments, both pn1416 and C10D8-5 were used to probe poly(A)⁺ RNA populations of mixed developmental stages of wild-type (strain N2), ced-4 (n1416), and ced-4(n1416 n1712). and ced-4(n1416 n1713) revertant animals. pn1416 hybridized to a 2.2 kb transcript and an 0.9 kb transcript in RNA from N2 animals, and a 3 kb transcript, a transcript slightly larger than the wild-type 2.2 kb transcript, and a transcript slightly smaller than the wild-type 0.9 kb transcript in ced-4(n1416) animals. The 3.8 kb RNA contained Tc4 sequence (see below), suggesting that this RNA resulted from the insertion of the 1.6 kb Tc4 sequence into the ced-4 sequence encoding 2.2 kb transcript. The transcript slightly larger than the 2.2 kb wild-type transcript did not contain Tc4 sequence. This ced-4( n1416) RNA might have been an aberrant transcript containing sequences adjacent to the ced-4 gene: when pn1416 was used as a probe, the wild-type 2.2 kb and the slightly larger transcript in this mutant were relatively similar in intensities, whereas when ced-4 cDNA clone SK2-1 was used as a probe, this mutant transcript was not detected (see below). These observations indicate that the ced-4(n1416) 2.2 kb transcript contains sequences from the ced-4 region but does not contain sequences corresponding to at least the 3' half of the ced-4 mRNA. The two revertants of ced-4(n1416), ced-4(n1416 n1712) and ced-4(n1416 n1713), contained both 2.2 kb and 0.9 kb transcripts with similar sizes to the wild-type transcripts. Thus, both the 2.2 kb and the 0.9 kb transcripts were altered in ced-4(n1416) animals, and both were restored in the two non-Ced revertants.

To determine if any of the transcripts contains Tc4 sequence, the Northern blots were probed with Tc4-n1351, which contains the 1.6 kb Tc4 element present in the Tc4-induced mutant unc-86(n1351) as well as 4 kb of unc-86 sequences. Tc4-n1351 hybridized both to a 3.8 kb transcript of the Tc4-induced mutant ced-4(n1416) and to a 1.5 kb unc-68 transcript in both ced-4(n1416) and N2 animals.

To determine whether one or both of the 2.2 kb and 0.9 kb transcripts are encoded by ced-4, subclone C10D8-5, which rescued the ced-4 phenotype, was used to probe the Northern blots. C10D8-5 detected the wild-type 2.2 kb transcript, the ced-4(n1416) transcript slightly larger than the 2.2 kb transcript, and the ced-4(n1416) 3.8 kb transcript. C10D8-5 did not hybridize to the 0.9 kb transcript, indicating that this transcript is unlikely to be encoded by ced-4. C10D8-5 also detected a 1.4 kb transcript, which was not altered by the Tc4 insertion in ced-4(n1416) animals. Only a 470 bp EcoRI-StuI fragment at one end of C10 D8-5 hybridized to this 1.4 kb RNA. Since C10D8-5 did not contain the complete coding region for this RNA, and since this RNA was unaffected in ced-4(n1416) animals, this 1.4 kb RNA seems unlikely to be a ced-4 transcript. The relationships among cosmid C10D8-5, pn1416 and the 0.9 kb, 1.4 kb and 2.2 kb transcripts are summarized in FIG. 8.

On Northern blots probed with the ced-4 CDNA clone SK2-1, the level of the 2.2 kb transcript showed significant reduction in all three independently derived EMS-induced ced-4 mutants examined, strongly supporting the hypothesis that this 2.2 kb transcript is a ced-4 transcript. Total RNA from N2, ced-4(n1162), ced-4(n1416), ced-4(n1894) and ced-4(n1920) eggs was probed with $^{32}$P-labelled ced-4 cDNA SK2-1. An actin 1 probe (Krause and Hirsh, in: *Molecular Biology of the Cytoskeleton*, Borisy et al. (eds.), Cold Spring Harbor Laboratory, 1984, pp. 287–292) was used as an internal control for the amount of RNA loaded in each lane. The ratios of the intensity of the ced-4 band to that of actin band in N2, n1162, n1416 and n1894 were 0.5, 0.17, 0 and 0.12, respectively. A Northern blot of poly(A)+ RNA from stage-synchronized animals was probed with pn1416, which hybridizes both to the 2.2 kb ced-4 transcript and to a 0.9 kb transcript. The 0.9 kb transcript seems to be expressed mostly in eggs and adults. The presence of RNA in all lanes was confirmed by loading 1/10 of each sample on another gel and probing a Northern blot from this gel using the *C. elegans* actin 1 gene (Krause and Hirsh, 1984 supra). That all of these distinct ced-4 mutations cause reduced levels of a ced-4 transcript could reflect either instability of all three mutant transcripts or a role for ced-4 in regulating its own expression.

Based upon these results, it can be concluded that the 2.2 kb RNA is a ced-4 transcript. It is not known why the 0.9 kb RNA is also altered in ced-4(n1416) animals. Perhaps transcription of the 0.9 kb RNA is initiated incorrectly as a consequence of the nearby Tc4 element.

ced-4 EXPRESSION IS PRIMARILY EMBRYONIC

A Northern blot containing RNAs from stage-synchronized animals of different developmental stages probed with pn1416 showed that the 2.2 kb ced-4 transcript was expressed primarily during embryogenesis. This result is consistent with the observation that 113 of the 131 programmed cell deaths in the *C. elegans* hermaphrodite are embryonic (Sulston and Horvitz, *Dev. Biol.* 82:110–156 (1977); Sulston et al., *Dev. Biol.* 100:64–119 (1983)). The 2.2 kb RNA was relatively abundant during embryonic development. The 0.9 kb transcript was expressed mostly in eggs and adults. The presence of RNA in all lanes was confirmed by loading 1/10 of each sample on another gel and probing a Northern blot from this gel with the *C. elegans* actin 1 gene (Krause and Hirsh, 1984 supra).

THE ced-4 TRANSCRIPT IS PRESENT IN A ced-3 MUTANT

The activities of both ced-3 and ced-4 are required for programmed cell death (Ellis and Horvitz, *Cell* 44:817–819 (1986)). One possibility is that one of these genes positively regulates the expression of the other. For this reason, a Northern blot of wild-type strain N2 and ced-3(n717) poly (A)$^+$ RNA was probed with pn1416. This experiment showed that the 2.2 kb ced-4 transcript was present at an apparently normal level in this ced-3 mutant. Thus, the activity of the ced-3 gene is unlikely to be necessary for the expression of the ced-4 2.2 kb transcript.

IDENTIFICATION OF ced-4 cDNA CLONES

To isolate cDNA clones of ced-4, pn1416 was used to probe a *C. elegans* cDNA phage library made from wild-type strain N2 mixed-stage RNA (Kim and Horvitz, *Genes & Dev.* 4:357–371 (1990)). Two cDNA clones were isolated. The two CDNA clones (named SK1 and SK2) hybridized to the 2.2 kb ced-4 transcript. Both are about 1.8 kb in size, and both contain one 0.8 kb and one 1.0 kb EcoRI fragment. These EcoRI fragments were subcloned into plasmid vector Bluescribe M13+ (Stratagene). The two subclones derived from SK1 were named SK1-1 and SK1-2, and the two subclones derived from SK2 were named SK2-1 and SK2-2. The restriction maps of the SK1- and SK2-derived clones were the same. Sequence analysis of the ends of the four cDNA subclones confirmed the equivalence of the SK1 and SK2 clones, except that SK1-2 contains a poly(A) sequence of more than 50 bp at its 5' end. This poly(A) sequence is probably a cDNA cloning artifact, since SK1-2 contains the 5' half of the cDNA (see below).

THE ced-4 SEQUENCE

The DNA sequence of the SK2 1.8 kb cDNA clone was determined. This sequence includes an open reading frame encoding 546 amino acids (FIG. 1; Seq. ID #2), which is consistent with the results of Northern blot analysis using single-stranded RNA probes. An ochre termination codon (TAA) is located in-frame near the 3' end, indicating that the 3' end of the 2.2 kb transcript is most likely included in this cDNA. The open reading frame extends to the 5' end of the 1.8 kb cDNA, suggesting that this cDNA might lack the 5' end of the ced-4 coding region.

A primer extension experiment was performed to determine the ced-4 transcription initiation site(s) using the primer ATTGGCGATCCTCTCGA (Seq. ID #23) and C10D8-5 as template. A major transcriptional initiation site was identified at 54 bp before (5' of) the beginning of the ced-4 cDNA SK2 and a minor initiation site at 54 bp after (3' of) the beginning of this cDNA (FIG. 1). The first AUG codon after the presumptive major start site is located at 9 bp before the beginning of the cDNA (FIG. 1). If this site is used to initiate protein synthesis, the Ced-4 protein would be 549 amino acids in length. The first AUG codon after the presumptive minor start site is located at 130 bp after the beginning of the cDNA. If this site is used, the Ced-4 protein would be 503 amino acids in length. Preliminary results using an anti-Ced-4 antibody raised against a Ced-4 fusion protein showed that endogenous Ced-4 protein is slightly smaller in molecular weight than a Ced-4 fusion protein of 562 amino acids expressed in *E. coli*. Thus, most Ced-4 protein is probably initiated near the start of the cDNA and is presumably 549 amino acids in length and 62,977 in relative molecular mass. The direction of the open reading frame is consistent with the direction of transcription, as demonstrated by probing Northern blots with single-stranded RNA probes. The presumptive Ced-4 protein is highly hydrophilic, with a pI of 5.12. The longest hydrophobic region is a segment of 12 amino acids from residues 382 to 393.

A Western blot of wild-type strain N2 mixed-stage, ced-4(n1416) mixed-stage, wild-type egg, and bacterially expressed protein (pJ76) was probed using anti-Ced-4 antibody. Ced-4 fusion protein (pJ76) was made by cloning ced-4 cDNA SK2 into the T7 expression vector pET-5a (Rosenberg et al., *Gene* 56:125–135 (1987)), so that 546 amino acids of Ced-4 sequence were fused to 11 amino acids of T7 gene 10 protein and 5 amino acids of linker sequence. This Ced-4 fusion protein is similar in relative molecular mass to the endogenous Ced-4 protein, which is present in wild,-type (N2) but missing in ced-4(n1416) animals. The proteins phosphorylase b, $97\times10^3$; bovine serum albumin, $66\times10^3$ (Hirayama et al., *Biochem. Biophys, Res. Comm.* 173:639–646 (1990)); and ovalbumin, $43\times10^3$, were used as molecular weight standards.

To confirm the DNA sequence obtained from the ced-4 cDNAs and to study the structure of the ced-4 gene, the sequences of the 4.4 kb cosmid subclone C10D8-5, the 3 kb insert pn1416, and the 2 kb HindIII-BamHI fragment that contains the Tc4 insertion in the ced-4( n1416) mutant were determined. Comparison of the ced-4 genomic and cDNA sequences revealed that the ced-4 gene has seven introns of sizes ranging from 44 bp to 557 bp (FIG. 2). The exon sequences of genomic clone C10D8-5 are identical to the sequences of ced-4 cDNA SK2. Comparison of the Tc4 insertion site in ced-4(n1416) DNA with the ced-4(+) genomic and cDNA sequences indicated that Tc4 inserted into an exon in the ced-4 gene in ced-4(n1416) animals (FIG. 2).

The DNA sequences of eight EMS-induced ced-4 alleles were also determined (Table 2). One of the eight, n1948, is a missense mutation. Of the seven others, four create stop codons and three are predicted to affect splicing of the ced-4 transcript. The positions of these mutations are indicated in FIG. 2. These findings indicate that the phenotypes of these mutants (Ellis and Horvitz, *Cell* 44:817–829 (1986)) result from a complete loss of ced-4 gene function. These mutations establish the null phenotype of the ced-4 gene, confirming that ced-4 function is not essential for viability.

The Ced-4 Protein Has Two Regions Similar to Known Calcium-Binding Domains

By direct inspection, the sequence of the putative Ced-4 protein was compared with the consensus sequence of the calcium-binding loop of the EF-hand domain (Tufty and Kretsinger, *Science* 187:161–171 (1975); Kretsinger, *Cold Spring Harbor Symp. Quant. Biol.* 52:499–510 (1987); Szebenyi and Moffat, *J. Biol. Chem.* 26:8761–8777(1986)). Two regions of the Ced-4 protein were identified that might bind calcium (FIG. 3).

The EF-hand is a 29 amino acid domain consisting of a helix-loop-helix region, with the loop portion (residues 10–21) coordinating calcium-binding via the side-chain oxygens of serine, threonine, asparagine, aspartic acid, glutamine or glutamic acid. These residues occur at five of the vertices of an octahedron: X (position 10), Y (12), Z (14), –X (18), –Z (21). EF-hand amino acid sequences vary considerably in the residues present in the calcium-binding loop (FIG. 3), and some EF-hand domains have only one helical region (Kretsinger, 1987 supra). The consensus sequence is shown at the top of FIG. 3. Positions Y, Z, and –X can have any of a number of amino acids which have oxygen-containing side chains. Position X is usually aspartic acid, and position –Z is usually glutamic acid.

The sequences of parvalbumins from carp muscle (Seg. ID #3; Nockolds et al., *Proc. Natl. Acad. Sci. USA* 69:581–584 (1972)), the intestinal calcium-binding protein (ICaBP) (Seq. ID #7–8; Szebenyi et al., *Nature* 294:327–332 (1981)), troponin C (Seq. ID #9–12; Collins et al., *FEBS Lett.* 36:268–272 (1973)) and calmodulin (Seq. ID #13; Zimmer et al., *J. Biol. Chem.* 263:19,370–19,383 (1988); Babu et al., *Nature* 315:37–40 (1985)) show canonical EF-hands. The hake and ray parvalbumins (Seq. ID #4–5; Capony et al. *Eur. J. Biochem.* 32:97–108 (1973)); Thatcher and Pechere, *Eur. J. Biochem.* 75:121–132 (1977)), sarcoplasmic calcium-binding protein (SCBP) from the protochordate Amphioxus (Seq. ID #6; Takagi et al., *Biochemistry* 25: 3585–3592 (1986)), trypsinogen (Seq. ID #14; Bode and Schwager, *J. Mol. Biol.* 98:693–717 (1975)), fibrinogen (Seq. ID #15; Doolittle, *Ann. Rev. Biochem.* 53:195–229 (1984); Dang et al., *J. Biol. Chem.* 260:9713–9719 (1985)), villin (Seg. ID #16; Hesterberg and Weber, *J. Biol. Chem.* 258:365–369 (1983)) and galactose-binding protein (GBP) (Seg. ID #17; Vyas et al., *Nature* 327:635–638 (1987)) show variations from the consensus sequence. GBP does not contain the helices of the EF-hand.

The potential calcium-binding loops of sequence 1 and sequence 2 are located at amino acids 77–88 and amino acids 292–303 of the Ced-4 protein, respectively (FIG. 3). In its putative calcium-binding loop, the first potential EF-hand-like sequence of the Ced-4 protein has four (positions Y, Z, –X, –Z) of the five conserved residues with oxygen-containing side chains (shown in bold), and the fifth position (X) has a tyrosine rather than an aspartic acid; tyrosine contains oxygen in its side chain. The second potential EF-hand-like sequence of the Ced-4 protein has three residues (positions Z, –X, –Z) that match the consensus sequence, and amino acids with oxygen-containing side chains at the other two positions. These observations suggest that these two regions of the Ced-4 protein might bind calcium. Like the Ced-4 protein, a number of known calcium-binding proteins, such a bovine intestinal calcium-binding protein (ICaBP) (Szebenyi and Moffat, 1986 supra), rabbit troponin C (Collins et al., 1973 supra), trypsinogen and villin (Doolittle, 1984 supra; Danget et al., 1985 supra) have only three or four conserved residues at these five positions (FIG. 3). The EF-hand domains in ICaBP and troponin C have been shown by X-ray crystallography to bind calcium.

One major difference between the Ced-4 protein and the calcium-binding loop of the EF-hand consensus sequence is at position 15. Here, the two Ced-4 sequences have a histidine and a glutamic acid, respectively, whereas most ET-hand-containing proteins have a glycine; this glycine has been suggested to be important for the turning of the loop (Kretsinger, 1987 supra). However, a histidine is present at this position in a parvalbumin and an aspartic acid is present in another parvalbumin and also in a sarcoplasmic calcium-binding protein (Kretsinger, 1987 supra) (FIG. 3). Thus, the presence of histidine or glutamic acid at position 15 does not rule out the possibility that these regions bind calcium.

The calcium-binding loop (positions 10–21) of the EF-hand is thought to be preceded (positions 1–9) and followed by alpha-helical domains (positions 22–29) (Kretsinger, 1987 supra). Since position 3 of Ced-4 sequence 1 and positions 26 and 28 of Ced-4 sequence 2 are prolines, these regions might not form alpha-helices. However, the known calcium-binding protein galactose-binding protein (GBP) has a calcium-binding domain similar to that of the EF-hand (FIG. 3) but without the two helices; furthermore, position 29 of GBP is proline (Vyas et al., 1987 supra). Thus, the Ced-4 protein need not contain such alpha-helical calcium-binding domains.

Based upon these considerations, it seems likely that the Ced-4 protein binds calcium or a similar divalent cation.

EXAMPLE 2

Cloning, Sequencing, and Characterization of the ced-3 Gene

Materials and Methods
General Methods and Strains

The techniques used for the culturing of C. elegans were as described by Brenner (*Genetics* 77:71–94 (1974)). All strains were grown at 20° C. The wild-type parent strains were C. elegans variety Bristol strain N2, Bergerac strain EM1002 (Emmons et al., *Cell* 32:55–65 (1983)), C. briggsae and C. vulgaris (obtained from V. Ambros). The genetic markers used are described below. These markers have been described by Brenner (1974 supra), and Hodgkin et al. (In: *The Nematode Caenorhabditis elegans*, Wood and the Community of C. elegans Researchers (eds.), Cold Spring Harbor Laboratory, 1988, pp 491–584). Genetic nomenclature follows the standard system (Horvitz et al., *Mol. Gen. Genet.* 175:129–133 (1979)).

LG I: ced-1(e1375); unc-54(r323)

LG VI: unc-31(e928), unc-30(e191), ced-3(n717, n718, n1040, n1129, n1163, n1164, n1165, n1286, n1949, n2426, n2430, n2433), unc-26(e205), dpy-4 (e1166)

LG V: eg1-1(n986); unc-76(e911)

LG X: dpy-3(e27)

ISOLATION OF ADDITIONAL ALLELES OF ced-3

A non-complementation screen was designed to isolate new alleles of ced-3. Because animals heterozygous for ced-3(n717) in trans to a deficiency are viable (Ellis and Horvitz, *Cell* 44:817–829 (1986)), animals carrying a complete loss-of-function ced-3, allele generated by mutagenesis were expected to be viable in trans to ced-3(n717), even if the new allele was inviable in homozygotes. Fourteen EMS mutagenized eg1-1 males were mated with ced-3 (n717) unc-26(e205); eg1-1 (n487); dpy-3(e27) hermaphrodites. eg1-1 was used as a marker in this screen. Dominant mutations in eg1-1 cause the two hermaphrodite specific neurons, the HSNs, to undergo programmed cell death (Trent et al., *Genetics* 104:619–647 (1983)). The HSNs are required for normal egg-laying, and eg1-1(n986) hermaphrodites, which lack HSNs, are egg-laying defective (Trent et al., 1983 supra). The mutant phenotype of eg1-1 is suppressed in a ced-3; eg1-1 strain because mutations in ced-3 block programmed cell deaths. eg1-1 males were mutagenized with EMS and crossed with ced-3(n717), unc-26(e205); eg1-1 (n487); dpy-3(e27). Most cross progeny were egg-laying defective because they were heterozygous for ced-3 and homozygous for eg1-1. Rare egg-laying competent animals were picked as candidates for carrying new alleles of ced-3. Four such animals were isolated from about 10,000 F1 cross progeny of EMS-mutagenized animals. These new mutations were made homozygous to confirm that they carried recessive mutations of ced-3.

MOLECULAR BIOLOGY

Standard techniques of molecular biology were used (Maniatis et al., *Molecular Cloning: A Laboratory Manual*, Cold Spring Harbor Laboratory, 1983).

Two cosmid libraries were used extensively in this work: a Sau3AI partial digest genomic library of 7000 clones in the vector pHC79 and a Sau3AI partial digest genomic library of 6000 clones in the vector pJB8 (Ish-Horowicz and Burke, *Nucleic Acids Res.* 9:2989 (1981)).

The "right" end of MMM-C1 was cloned by cutting it with HindIII and self-ligating. The "left" end of MMM-C1 was cloned by cutting it with BglII or SalI and self-ligating.

The "right" end of Jc8 was made by digesting Jc8 with EcoRI and self-ligating. The "left" end of Jc8 was made by digesting Jc8 by SalI and self-ligating.

C. elegans RNA was extracted using guanidine isothiocyanate (Kim and Horvitz, *Genes & Dev.* 4:357–371 (1990)). Poly(A)$^+$ RNA was selected from total RNA by a poly(dT) column (Maniatis et al., 1983 supra). To prepare stage-synchronized animals, worms were synchronized at different developmental stages (Meyer and Casson, *Genetics* 106:29–44 (1986)).

For DNA sequencing, serial deletions were made according to a procedure developed by Henikoff (Gene 28:351–359 (1984)). DNA sequences were determined using Sequenase and protocols obtained from US Biochemicals with minor modifications.

The Tc1 DNA probe for Southern blots was pCe2001, which contains a Bergerac Tc1 element (Emmons et al., *Cell* 32:55–65 (1983)). Enzymes were purchased from New England Biolabs, and radioactive nucleotides were from Amersham.

Primer extension procedures followed the protocol by Robert E. Kingston (In: *Current Protocols in Molecular Biology*, Ausubel et al. (eds.), Greene Publishing Associates and Wiley-Interscience, New York, p. 4.8.1) with minor modifications.

Polymerase chain reaction (PCR) was carried out using standard protocols supplied by the GeneAmp Kit (Perkin Elmer). The primers used for primer extension and PCR are as follows:

Pex2: 5' TCATCGACTTTTAGATGACTAGAGAA-CATC 3' (Seq. ID #24);

Pex1: 5' GTTGCACTGCTTTCACGATCTC-CCGTCTCT 3' (Seq. ID #25);

SL1: 5' GTTTAATTACCCAAGTTTGAG 3' (Seq. ID #26);

SL2: 5' GGTTTTAACCAGTTACTCAAG 3' (Seq. ID #27);

Log5: 5' CCGGTGACATTGGACACTC 3' (Seq. ID #28); and

Oligo10: 5' ACTATTCAACACTTG 3' (Seq. ID #29).

GERMLINE TRANSFORMATION

The procedure for microinjection basically follows that of A. Fire (*EMBO J.* 5:2673–2680 (1986)) with modifications:

Cosmid DNA was twice purified by CsCl-gradient. Miniprep DNA was used when deleted cosmids were injected. To prepare miniprep DNA, DNA from 1.5 ml overnight bacterial culture in superbroth (12 g Bacto-tryptone, 24 g yeast extract, 8 ml 50% glycerol, 900 ml H$_2$O, autoclaved; after autoclaving, 100 ml 0.17 M KH$_2$PO$_4$ and 0.72 M KH$_2$PO$_4$ were added) was extracted by alkaline lysis method as described in Maniatis et al. (1983 supra). DNA was treated with RNase A (37°, 30 minutes) and then with protease K (55°, 30 minutes), extracted with phenol and then chloroform, precipitated twice (first in 0.3 M sodium acetate and second in 0.1. M potassium acetate, pH 7.2), and resuspended in 5 µl injection buffer as described by A. Fire (1986 supra). The DNA concentration for injection is in the range of 100 ug to 1 mg per ml.

All transformation experiments used ced-1(e1735); unc-31(e928) ced-3(n717) strain. unc-31 was used as a marker for co-transformation (Kim and Horvitz, 1990 supra). ced-1 was present to facilitate scoring of the ced-3 phenotype. The mutations in ced-1 block the engulfment process of cell death, which makes the corpses of the dead cells persist much longer than in wild-type animals (Hedgecock et al., *Science* 220:1277–1280 (1983)). The ced-3 phenotype was scored as the number of dead cells present in the head of young L1 animals. The cosmid C10D8 or the plasmid subclones of C10D8 were mixed with C14G10 (unc-31(+)-containing) at a ratio of 2:1 or 3:1 to increase the chances that a Unc-31(+) transformant would contain the cosmid or plasmid being tested as well. Usually, 20–30 animals were injected in one experiment. Non-Unc F1 progeny of the injected animal were isolated three to four days later. About ½ to ⅓ of the non-Unc progeny transmitted the non-Unc phenotype to F2 progeny and established a transformant line. The young L1 progeny of such non-Unc transformant were checked for the number of dead cells present in the head using Nomarski optics.

RESULTS

Isolation of Additional ced-3 Alleles

All of the ced-3 alleles that existed previously were isolated in screens designed to detect viable mutants displaying the Ced phenotype (Ellis and Horvitz, *Cell* 44:817–829 (1986)). Such screens may have systematically missed any class of ced-3 mutations that is inviable as homozygotes. For this reason, a scheme was designed that could isolate recessive lethal alleles of ced-3. Four new alleles of ced-3 (n1163, n1164, n1165, n1286) were isolated in this way. Since new alleles were isolated at a frequency of about 1 in 2500, close to the frequency expected for the generation of null mutations by EMS in an average *C. elegans* gene (Brenner, *Genetics* 77:71–94 (1974); Greenwald and Horvitz, *Genetics* 96:147–160 (1980)), and all four alleles are homozygous viable, it was concluded that the null allele of ced-3 is viable.

MAPPING RFLPs NEAR ced-3

Tc1 is a *C. elegans* transposable element that is thought to be immobile in the common laboratory Bristol strain and in the Bergerac strain (Emmons et al., *Cell* 32:55–65 (1983)). In the Bristol strain, there are 30 copies of Tc1, while in the Bergerac strain, there are more than 400 copies of Tc1 (Emmons et al., 1983 supra; Finney, Ph.D. thesis, Massachusetts Institute of Technology, Cambridge, Mass., 1987). Because the size of the *C. elegans* genome is small (haploid genome size 8×10$^7$ bp) (Sulston and Brenner, *Genetics* 77:95–104 (1976)), a polymorphism due to Tc1 between the Bristol and Bergerac strains would be expected to occur about once every 200 kb. Restriction fragment length polymorphisms (RFLPs) can be used as genetic markers and mapped in a manner identical to conventional mutant phenotypes. A general scheme has been designed to map Tc1 elements that are dimorphic between the Bristol and Bergerac strains near any gene of interest (Ruvkun et al., *Genetics*, 121:501–516 (1989)). Once tight linkage of a particular Tc1 to a gene of interest has been established, that Tc1 can be cloned and used to initiate chromosome walking.

A 5.1 kb Bristol-specific Tc1 EcoRI fragment was tentatively identified as containing the Tc1 closest to ced-3. This Tc1 fragment was cloned using cosmids from a set of Tc1-containing *C. elegans* Bristol genomic DNA fragments. DNA was prepared from 46 such TC1-containing cosmids, and this DNA was screened using Southern blots to identify the cosmids that contain a 5.1 kb EcoRI Tc1-containing fragment. Two such cosmids were identified: MMM-C1 and MMM-C9. The 5.1 kb ECoRI fragment was subcloned from MMM-C1 into pUC13 (Promega). Since both ends of Tc1 contain an EcoRV site (Rosenzweig et al., *Nucleic Acids Res.* 11:4201–4209 (1983)), EcoRV was used to remove Tc1 from the 5.1 kb EcoRI fragment, generating a plasmid that contains only the unique flanking region of this Tc1-containing fragment. This plasmid was then used to map the specific Tc1 without the interference of other Tc1 elements.

unc-30 (e191) ced-3 (n717) dpy-4 (e1166)/+++ males were crossed with Bergerac (EM1002) hermaphrodites, and Unc non-Dpy or Dpy non-Unc recombinants were picked from among the F2 progeny. The recombinants were allowed to self-fertilize, and strains that were homozygous for either unc-30(e191) dpy-4(Bergerac) or unc-30 (Bergerac) dpy-4(e1166) were isolated. After identifying the ced genotypes of these recombinant strains, DNA was prepared from these strains. A Southern blot of DNA from these recombinants was probed with the flanking sequence of the 5.1 kb EcoRI TC1 fragment. This probe detects a 5.1 kb fragment in Bristol N2 and a 3.4 kb fragment in Bergerac. Five out of five unc-30 ced-3 dpy(+Berg) recombinants, and one of one unc-30(+Berg) ced-3 dpy-4 recombinants showed the Bristol pattern. Nine of ten unc-30(+Berg) dpy-4 recombinants showed the Bergerac pattern. Only one recombinant of unc-30(+Berg) dpy-4 resulted from a cross-over between ced-3 and the 5.1 kb Tc1 element. The genetic distance between ced-3 and dpy-4 is 2 map units (mu). Thus, this Tc1 element is located 0.1 mu on the right side of ced-3.

Cosmids MMM-C1 and MMM-C9 were used to test whether any previously mapped genomic DNA cosmids overlapped with these two cosmids. A contig of overlapping cosmids was identified that extended the cloned region near ced-3 in one direction.

To orient MMM-C1 with respect to this contig, both ends of MMM-C1 were subcloned and these subclones were used to probe the nearest neighboring cosmid C48D1. The "right" end of MMM-C1 does not hybridize to C48D1, while the "left" end does. Therefore, the "right" end of MMM-C1 extends further away from the contig. To extend this contig, the "right" end of MMM-C1 was used to probe the filters of two cosmid libraries (Coulson et al., *Proc. Natl. Acad. Sci. USA* 83:7821–7825 (1986)). One clone, Jc8, was found to extend MMM-C1 in the opposite direction of the contig.

RFLPs between the Bergerac and Bristol strains were used to orient the contig with respect to the genetic map. Bristol (N2) and Bergerac (EM1002) DNA was digested with various restriction enzymes and probed with different cosmids to look for RFLPs. Once such an RFLP was found, DNA from recombinants of the Bristol and Bergerac strains between ced-3 and unc-26, and between unc-30 and ced-3 was used to determine the position of the RFLP with respect to ced-3.

The "right" end of Jc8, which represents one end of the contig, detects an RFLP (nP33) when N2 and EM1002 DNA was digested with HindIII. A Southern blot of DNA from recombinants between three ced-3(+Berg) unc-26 was probed with the "right" end of Jc8. Three of three +Berg unc-26 recombinants showed the Bristol pattern, while two of two ced-3 unc-26(+Berg) recombinants showed the Bergerac pattern. Thus, nP33 mapped very close or to the right side of unc-26.

The "left" end of Jc8 also detects a HindIII RFLP (nP34). The same Southern blot was reprobed with the Jc8 "left" end. Two of the two ced-3 unc-26(+Berg) recombinants and two of the three ced-3(+Berg) unc-26 recombinants showed the Bergerac pattern. One of the three ced-3(+Berg) unc-26 recombinants showed the Bristol pattern. The genetic distance between ced-3 and unc-26 is 0.2 mu. Thus, nP34 was mapped between ced-3 and unc-26, about 0.1 mu on the right side of ced-3.

The flanking sequence of the 5.1 kb EcoRI Tc1 fragment (named nP35) was used to probe the same set of recombinants. Two of three ced-3(+Berg) unc-26 recombinants and two of two ced-3 unc-26(+Berg) recombinants showed the Bristol pattern. Thus, nP35 was also found to be located between ced-3 and unc-26, about 0.1 mu on the right side of ced-3.

A similar analysis using cosmid T10H5 which contains the HindIII RFLP (nP36), and cosmid B0564, which contains a HindIII RFLP (nP37), showed that nP36 and nP37 mapped very close or to the right of unc-30.

Figure 9:
FIG. 9 shows physical and genetic maps of the ced-3 region on chromosome IV.

These experiments localized the ced-3 gene to an interval of three cosmids. The positions of the RFLPS, and of ced-3, unc-30 and unc-26 on chromosome IV, and their relationships to the cosmids are shown in FIG. 9. It was has been further demonstrated by microinjection that cosmids C37G8 and C33F2 carry the unc-30 gene (John Sulston, personnel communication). Thus, the region containing the ced-3 gene was limited to an interval of two cosmids. These results are summarized in FIG. 9.

COMPLEMENTATION OF ced-3 BY GERMLINE TRANSFORMATION

Cosmids that were candidates for containing the ced-3 gene were microinjected into a ced-3 mutant to see if they rescue the mutant phenotype. The procedure for microinjection was that of A. Fire (*EMBO J.* 5:2673–2680 (1986)) with modifications. unc-31, a mutant defective in locomotion, was used as a marker for cotransformation (Kim and Horvitz, *Genes & Dev.* 4:357–371 (1990)), because the phenotype of ced-3 can be examined only by using Nomarski optics. Cosmid C14G10 (containing unc-31(+)) and a candidate cosmid were coinjected into ced-1 (e1375); unc-31 (e928) ced-3(n717) hermaphrodites, and F1 non-Unc transformants were isolated to see if the non-Unc phenotype could be transmitted and established as a line of transformants. Young L1 progeny of such transformants were examined for the presence of cell deaths using Nomarski optics to see whether the ced-3 phenotype was suppressed. Cosmid C14G10 containing unc-31 alone does not rescue ced-3 activity when injected into a ced-3 mutant. Table 4 summarizes the results of these transformation experiments.

As shown in Table 4, of the three cosmids injected (C43C9, W07H6 and C48D1), only C48D1 rescued the ced-3 phenotype (⅔ non-Unc transformants rescued the ced-3 phenotype). One of the transformants, nEX2, appears to be rescued by an extra-chromosomal array of injected cosmids (Way and Chalfie, *Cell* 54:5–16 (1988)), which is maintained as an unstable duplication, since only 50% of the progeny of a non-Unc Ced(+) animal are non-Unc Ced(+). Since the non-Unc Ced(+) phenotype of the other transformant (nIS1) is transmitted to all of its progeny, it is presumably an integrated transformant. L1 ced-1 animals contain an average of 23 cell corpses in the head (Table 5). L1 ced-1; ced-3 animals contain an average of 0.3 cell corpses in the head. ced-1; unc-31 ced-3; nIS1 and ced-1; unc-31 ced-3; nEX2 animals contain an average of 16.4 and 14.5 cell corpses in the head, respectively. From these results, it was concluded that C48D1 contains the ced-3 gene.

In order to locate ced-3 more precisely within the cosmid C48D1, this cosmid was subcloned and the subclones were tested for the ability to rescue ced-3 mutants (Table 5). C48D1 DNA was digested with restriction enzymes that cut rarely within the cosmid and the remaining cosmid was self-ligated to generate a subclone. Such subclones were then injected into a ced-3 mutant to look for complementation; young L1 non-Unc progeny of the transformants were examined using Nomarski optics for the presence of cell death in the head. When C48D1 was digested with BamHI and self-ligated, the remaining 14 kb subclone (named C48D1-28) was found to rescue the ced-3 phenotype when injected into a ced-3 mutant (FIG. 10 and Table 5). C48D1-28 was then partially digested with BglII and self-ligated. Clones of various lengths were isolated and tested for their ability to rescue ced-3.

One clone, C48D1-43, which did not contain a 1.7 kb BglII fragment of C48D1-28, was able to rescue ced-3 (FIG. 10 and Table 5). C48D1-43 was further subcloned by digesting with BamHI and ApaI to isolate a 10 kb BamHI-ApaI fragment. This fragment was subcloned into pBSKII+ to generate pJ40. pJ40 can restore ced-3+ phenotype when microinjected into a ced-3 mutant. pJ40 was subcloned by deleting a 2 kb BglII-ApaI fragment to generate pJ107. pJ107 was also able to rescue the ced-3 phenotype when microinjected into a ced-3 mutant. Deletion of 0.5 kb on the left side of pJ107 could be made by ExoIII digestion (as in pJ107del28 and pJ107del34) without affecting ced-3 activity; in fact, one transgenic line, nEX17, restores full ced-3 activity. However, the ced-3 rescuing ability was significantly reduced when 1 kb was deleted on the left side of pJ107 (as in pJ107del12 and pJ107del27), and the ability was completely eliminated when a 1.8 kb SalI-BglII fragment was deleted on the right side of pJ107 (as in pJ55 and pJ56), suggesting that this SalI site is likely to be in the ced-3 coding region. From these experiments, ced-3 was localized to a DNA fragment of 7.5 kb. These results are summarized in FIG. 10 and Table 5.

ced-3 TRANSCRIPT pJ107 was used to probe a Northern blot of N2 RNA and detected a band of 2.8 kb. Although this transcript is present in 12 ced-3 mutant animals, subsequent analysis showed that all 12 ced-3 mutant alleles contain mutations in the genomic DNA that codes for this mRNA (see below), thus establishing this RNA as a ced-3 transcript.

The developmental expression pattern of ced-3 was determined by hybridizing a Northern blot of RNA from animals of different stages (eggs, L1 through L4 larvae and young adult) with the ced-3 cDNA subclone pJ118. Such analysis revealed that the ced-3 transcript is most abundant during embryonic development, which is the period when most programmed cell deaths occur, but it was also detected during the L1 through L4 larval stages and is present in relatively high levels in young adults. This result suggests that ced-3 is not only expressed in cells undergoing programmed cell death.

Since ced-3 and ced-4 are both required for programmed cell death in *C. elegans*, one of the genes might-act as a regulator of transcription of the other gene. To examine if ced-4 regulates the transcription of ced-3, RNA was prepared from eggs of ced-4 mutants (n1162, n1416, n1894, and n1920), and a Northern blot was probed with the ced-3 cDNA subclone pJ118. The presence of RNA in each lane was confirmed with an actin I probe. Such an experiment showed that the level of ced-3 transcript is normal in ced-4 mutants. This indicates that ced-4 is unlikely to be a transcriptional regulator of ced-3.

ISOLATION OF A ced-3 cDNA

To isolate cDNA of ced-3, pJ40 was used as a probe to screen a CDNA library of N2 (Kim and Horvitz, *Genes & Dev.* 4:357–371 (1990)). Seven cDNA clones were isolated. These cDNAs can be divided into two groups: one is 3.5 kb and the other 2.5 kb. One cDNA from each group was subcloned and analyzed further. pJ85 contains the 3.5 kb cDNA. Experiments showed that pJ85 contains a ced-3 cDNA fused to an unrelated cDNA; on Northern blots of N2 RNA, the pJ85 insert hybridizes to two RNA transcripts, and on Southern blots of N2 DNA, pJ85 hybridizes to more than one band than pJ4O (ced-3 genomic DNA) does. pJ87 contains the 2.5 kb CDNA. On Northern blots, pJ87 hybridizes to a 2.8 kb RNA and on Southern blots, it hybridizes only to bands to which pJ40 hybridizes. Thus, pJ87 contains only ced-3 CDNA.

To show that pJ87 does contain the ced-3 cDNA, a frameshift mutation was made in the SalI site of pJ40 corresponding to the SaiII site in the pJ87 cDNA. Constructs containing the frameshift mutation failed to rescue the ced-3 phenotype when microinjected into ced-3 mutant animals, suggesting that ced-3 activity has been eliminated.

ced-3 SEQUENCE

The DNA sequence of pJ87 was determined (see FIG. 4; Seq. ID #18). pJ87 contains an insert of 2.5 kb which has an open reading frame of 503 amino acids (FIG. 4; Seq. ID #19). The 5' end of the cDNA contains 25 bp of poly-A/T sequence, which is probably an artifact of cloning and is not present in the genomic sequence. The cDNA ends with a poly-A sequence, suggesting that it contains the complete 3' end of the transcript. 1 kb of pJ87 insert is untranslated 3' region and not all of it is essential for ced-3 expression, since genomic constructs with deletions of 380 bp of the 3' end can still rescue ced-3 mutants (pJ107 and its derivatives, see FIG. 10).

To confirm the DNA sequence obtained from the ced-3 cDNA and to study the structure of the ced-3 gene, the genomic sequence of the ced-3 gene in the plasmid pJ107 was determined (FIG. 4; Seq. ID #18). Comparison of the ced-3 genomic and cDNA sequences revealed that the ced-3 gene has seven introns that range in size from 54 bp to 1195 bp (FIG. 5A). The four largest introns, as well as sequences 5' of the start codon, were found to contain repetitive elements. Five types of repetitive elements were found, some of which have been previously characterized in non-coding regions of other *C. elegans* genes such as fem-1 (Spence et al., *Cell* 60:981–990 (1990)), lin-12 (J. Yochem, personal communication), and myoD (Krause et al., *Cell* 63:907–919 (1990)) (FIG. 4). Of these, repeat 1 was also found in fem-1 and myoD, repeat 3 in lin-12 and fem-1, repeat 4 in lin-12, and repeats 2 and 5 were novel repetitive elements.

A combination of primer extension and PCR amplification was used to determine the location and nature of the 5' end of the ced-3 transcript. Two primers (Pex1 and Pex2) were used for the primer extension reaction. The Pex1 reaction yielded two major bands, whereas the Pex2 reaction gave one band. The Pex2 band corresponded in size to the smaller band from the Pex1 reaction, and agreed in length with a possible transcript that is trans-spliced to a *C. elegans* splice leader (Bektesh, *Genes & Dev.*, 2:1277–1283 (1988)) at a consensus splice acceptor at position 2166 of the genomic sequence (FIG. 4). The nature of the larger Pex1 band is unclear.

To confirm the existence of this trans-spliced message in wild-type worms, total *C. elegans* RNA was PCR amplified using the SL1-Log5 and SL2-Log5 primer pairs, followed by a reamplification using the SL1-oligolo and SL2-Oligo10 primer pairs. The SL1 reaction yielded a fragment of the predicted length. The identity of this fragment was confirmed by sequencing. Thus, at least some, if not most, of the ced-3 transcript is trans-spliced to SL1. Based on this result, the start codon of the ced-3 message was assigned to the methionine encoded at position 2232 of the genomic sequence (FIG. 4).

The DNA sequences of 12 EMS-induced ced-3 alleles were also determined (FIG. 4 and Table 3). Nine of the 12 are missense mutations. Two of the 12 are nonsense mutations, which might prematurely terminate the translation of ced-3. These nonsense ced-3 mutants confirmed that the ced-3 gene is not essential for viability. One of the 12 mutations is an alteration of a conserved splicing acceptor G, and another has a change of a 70% conserved C at the splice site, which could also generate a stop codon even if the splicing is correct. Interestingly, these EMS-induced mutations are in either the N-terminal quarter or C-terminal half of the protein. In fact, 9 of the 12 mutations occur within the region of ced-3 that encodes the last 100 amino acids of the protein. Mutations are notably absent from the middle part of the ced-3 gene (FIG. 5).

Ced-3 contains A Region Rich in Serines

The Ced-3 protein is very hydrophilic and no significantly hydrophobic region can be found that might be a transmembrane domain (FIG. 6). The Ced-3 protein is rich in serine. From amino acid 78 to amino acid 205 of the Ced-3 protein, 34 out of 127 amino acids are serine. Serine is often the target of serinel threonine protein kinases (Edelman, *Ann. Rev. Biochem.* 56:567–613 (1987)). For example, protein kinase C can phosphorylate serines when they are flanked on their amino and carboxyl sides by basic residues (Edelman, 1987 supra). Four of the serines in the Ced-3 protein are flanked by arginines (FIG. 4). The same serine residues might also be the target of related Ser/Thr kinases.

To identify the functionally important regions of the Ced-3 protein, genomic DNAs containing the ced-3 genes from two related nematode species, *C. briggsae* and *C. vulgaris* were cloned and sequenced (FIG. 7; Seq. ID #20 and 21). Sequence comparison of the three ced-3 genes showed that the non-serine-rich region of the proteins is highly conserved. In *C. briggsae* and *C. vulgaris*, many amino acids in the serine-rich region are dissimilar compared to the *C. elegans* Ced-3 protein (FIG. 7). It seems that what is important in the serine-rich region is the overall serine-rich feature rather than the exact amino acid sequence.

This hypothesis is also supported by analysis of ced-3 mutations in *C. elegans*: none of the 12 EMS-induced mutations is in the serine-rich region, suggesting that mutations in this region might not affect the function of the Ced-3 protein and thus, could not be isolated in the screen for ced-3 mutants.

TABLE 1

Rescue of the Ced-4 Phenotype by Germline Transformation

| Genotype | DNA Injected | Avg. No. Cell Corpses (L1 Head) | No. Animals Scored |
| --- | --- | --- | --- |
| ced-1; ced-4; unc-31; nEx1 | C10D8; C14G10 | 9.4 | 10 |
| ced-1; ced-4; unc-31; nEx7 | C10D8-5 C14G10 | 11.5 | 10 |
| ced-1; ced-4 unc-31; nEx8 | C10D8-5 C14G10 | 11.5 | 10 |
| ced-1 | None | 23 | 20 |
| ced-1; ced-4 | None | 0.6 | 20 |

TABLE 2

Sites of Mutations in the ced-4 Gene

| Allele | Mutation | Nucleotide | Codon | Consequence |
| --- | --- | --- | --- | --- |
| n1162 | C to T | 1131 | 40 | Q to ochre (TAA) |
| n2274 | C to T | 1428 | 139 | R to opal (TGA) |
| n1920 & n2247 | G to A | 1744 | first base of 5' splice donor of intron 3 | Altered splicing |
| n2273 | G to A | 1929 | first base of 3' splice acceptor of intron 3 | Altered splicing |
| n1948 | T to A | 2117 | 258 | I to N |
| n1947 | C to T | 2128 | 262 | Q to amber |
| n1894 | G to A | 3131 | 401 | W to opal (TGA) |

Nucleotide and codon positions correspond to the numbering in FIG. 1.

TABLE 3

Sites of Mutations in the ced-3 Gene

| Allele | Mutation | Nucleotide | Codon | Consequence |
| --- | --- | --- | --- | --- |
| n1040 | C to T | 2310 | 27 | L to F |
| n718 | G to A | 2487 | 65 | G to R |
| n2433 | G to A | 5757 | 360 | G to S |
| n1164 | C to T | 5940 | 403 | Q to termination |
| n717 | G to A | 6297 | — | Splice acceptor loss |
| n1949 | C to T | 6322 | 412 | Q to termination |
| n1286 | G to A | 6342 | 428 | W to termination |
| n1129 | C to T | 6434 | 449 | A to V |
| n1165 | C to T | 6434 | 449 | A to V |
| n2430 | C to T | 6485 | 466 | A to V |
| n2426 | G to A | 6535 | 483 | E to K |
| n1163 | C to T | 7020 | 486 | S to F |

Nucleotide and codon positions correspond to the numbering in FIG. 4.

TABLE 4

Summary of Transformation Experiments Using Cosmids in the ced-3 Region

| Cosmid injected | No. of non-Unc transformants | Ced-3 phenotype | Strain name |
| --- | --- | --- | --- |
| C43C9; C14G10 | 1 | − | MT4302 |
| W07H6; C14G10 | 3 | − | MT4299 |
| | | − | MT4300 |
| | | − | MT4301 |
| C48D1; C14G10 | 2 | + | MT4298 |
| | | + | MT4303 |

Animals injected were of genotype: ced-1 (e1735); unc-31 (e929) ced-3 (n717).

TABLE 5

The expression of ced-3(+) transformants

| Genotype | DNA injected | Average No. cell deaths in L1 head | No. Animals scored |
| --- | --- | --- | --- |
| ced-1 | — | 23 | 20 |
| ced-1; ced-3 | — | 0.3 | 10 |
| ced-1; nIS1 unc-31 ced-3 | C48D1; C14G10 | 16.4 | 20 |
| ced-1; unc-31 ced-3; nIS1/+ | | 14.5 | 20 |
| ced-1; unc-31 ced-3; nEX2 | C48D1; C14G10 | 13.2 | 10/14 |
| | | 0 | 4/14 |
| ced-1; unc-31 ced-3; nEX10 | C48D1-28; C14G10 | 12 | 9/10 |
| | | 0 | 1 of 10 |
| ced-1; unc-31 ced-3; nEX9 | C48D1-28; C14G10 | 12 | 10 |
| ced-1; unc-31 ced-3; nEX11 | C48D1-43 C14G10 | 16.7 | 10/13 |
| | | Abnormal cell deaths | 3/13 |
| ced-1; unc-31 ced-3; nEX13 | pJ40; C14G10 | 13.75 | 4/4 |
| ced-1; unc-31 ced-3; nEX17 | pJ107de128, pJ107de134 C14G10 | 23 | 12/14 |
| | | 0 | 2/14 |
| ced-1; unc-31 ced-3; nEX18 | pJ107de128, pJ107de1134 C14G10 | 12.8 | 9/10 |
| | | 0 | 1/10 |
| ced-1; unc-31 ced-3; nEX19 | pJ107de128, pJ107de134 G14G10 | 10.6 | 5/6 |
| | | 0 | 1/6 |
| ced-1; unc-31 ced-3; nEX16 | pJ107de112, pJ107de127 C14G10 | 7.8 | 12/12 |

Alleles of the genes used are ced-1(e1735), unc-31(e928), and ced-3 (n717).

EQUIVALENTS

Those skilled in the art will recognize, or be able to ascertain using no more than routine experimentation, many equivalents to the specific embodiments of the invention described herein. Such equivalents are intended to be encompassed by the following claims. For example, functional equivalents of DNAs and RNAs may be nucleic acid sequences which, through the degeneracy of the genetic code, encode the same proteins as those specifically claimed. Functional equivalents of proteins may be substituted or modified amino acid sequences, wherein the substitution or modification does not change the activity or function of the protein. A "silent" amino acid substitution, such that a chemically similar amino acid (e.g., an acidic amino acid with another acidic amino acid) is substituted, is an example of how a functional equivalent of a protein can be produced. Functional equivalents of nucleic acids or proteins can also be produced by deletion of nonessential sequences.

What is claimed is:

1. An isolated and purified ced-3 nucleic acid comprising a nucleic acid which encodes the amino acid sequence of SEQ ID NO: 19.

2. The isolated and purified ced-3 nucleic acid of claim 1, comprising the sequence of SEQ ID NO: 18.

3. An isolated RNA encoded by the nucleic acid of claim 1.

4. An isolated and purified ced-3 nucleic acid comprising a mutation in SEQ ID NO: 18, wherein said mutation in ced-3 is selected from the group consisting of:
  a) n1040;
  b) n718;
  c) n2433;
  d) n1164;
  e) n717;
  f) n1949;
  g) n1286;
  h) n1129;
  i) n1165;
  j) n2430;
  k) n2426; and
  l) n1163.

5. An isolated and purified ced-3 nuclcic acid comprising a mutation in SEQ ID NO:18, wherein said mutation is selected from the group consisting of:
  a) a C to T at nucleotide 2310 of SEQ ID NO: 18, resulting in a L to F alteration at position 27 of SEQ ID. NO:19;
  b) a G to A at nucleotide 2487 of SEQ ID NO:18, resulting in a G to R alteration at position 65 of SEQ ID NO: 19;
  c) a G to A at nucleotide 5757 of SEQ ID NO:18, resulting in a G to S alteration at position 360 of SEQ ID NO: 19;
  d) a C to T at nucleotide 5940 of SEQ ID NO:18, resulting in a Q to termination alteration at position 403 of SEQ ID NO: 19;
  e) a C to T at nucleotide 6322 of SEQ ID NO:18, resulting in a Q to termination alteration at position 412 of SEQ ID NO: 19;
  f) a G to A at nucleotide 6342 of SEQ ID NO:18, resulting in a W to termination alteration at pocition 428 of SEQ ID NO: 19;
  g) a C to T at nucleotide 6434 of SEQ ID NO:18, resultng in a A to V alteration at position 449 of SEQ ID NO:19;
  h) a C to T at nucleotide 6485, resulting in a A to V alteration at position 466 of SEQ ID NO:19;
  i) a G to A at nucleotide 6535, resulting in a E to K alteration at position 483 of SEQ ID NO: 19;
  j) a C to T at nucleotide 7020, resulting in an S to F alteration at position 486 of SEQ ID NO:19;
  k) an alteration in mRNA splicing at nucleotide 6297.

6. An isolated and purified ced-3 nucleic acid comprising a mutation in SEQ ID NO:18, wherein said mutation in ced-3 is selected from the group consisting of:
  a) C to T at nucleotide 2310 of SEQ ID NO: 18;
  b) G to A at nucleotide 2487 of SEQ ID NO: 18;
  c) G to A at nucleotide 5757 of SEQ ID NO: 18;
  d) C to T at nucleotide 5940 of SEQ ID NO: 18;
  e) G to A at nucleotide 6297 of SEQ ID NO: 18;
  f) C to T at nucleotide 6322 of SEQ ID NO: 18;
  g) G to A at nucleotide 6342 of SEQ ID NO: 18;
  h) C to T at nucleotide 6434 of SEQ ID NO: 18;
  i) C to T at nucleotide 6485 of SEQ ID NO: 18;
  j) G to A at nucleotide 6535 of SEQ ID NO: 18;
  k) C to T at nucleotide 7020 of SEQ ID NO: 18.

* * * * *

SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
       (A) LENGTH: 4407 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 1:

```
GAATTCGCGT CGAATCATTG TCTGTTCGGT ATCGATTCAG AAACCGAAAC TTGTGATCGA      60

TAACAAGTCA TTCAAACACG GCGAAGATGT CTATGCGTAT AACAGAATAT TTGGAGAAAT     120

GCTCGCAAAA CTCGAAATTG TCACCGATAA AATGATTAAC TTGAAGGGGC TAATGTAAGT     180

TATCTGATGT TTCTACAATT AAAAAAATTG TTTTTTTTTC AAATTAATT TTCGAAGATT      240

AACGAAAAAC GATTAAAAAT CAATAAAACG CAATAAAGAG GGCTTGGCTT TCTTTTTAAT     300

TTAAATTATA ATTTTTCTGA TTGTTGTATG AAGCTACAAA ATGTACTGTT TTTGTATTTG     360

AATATTGTAT TACAGGGTTG GGATTCTCGG CAAATATCAG CGACAGTGGA AGATTTAGAA     420

GAAGGACGTG TGACAATCAC TAAGTCAAAG AGGGAAAGGA TAAAGGATTG TGATATTTCA     480

CTGTTTTACT CATTCGCTTT TTAAATAAGA ACTATATGCC GATTTGCCGA TATATTTTG     540

TTTATTAGGC CTCTCACATT CCTGTACAAT GTTTCTACCA AATAAACTGC ATTTTTATCT     600

GAAAATTCGA ATTTATTTTT GTCTACTTTT TACTCGTTGC ATTCGAGATC AGCATATCTT     660

CCGGTCTATT TATATTCAAC GATTTTTATA AATTAGTACT CCTTCATGTT TAATTTCATT     720

TTATCTGTAA GCTTTACTGT ATTTTTTTAA AATCTTTCTT GCTTCTATCT GATTATACAA     780

TGTTCTTTAC TCATTTTCAA GGTATTTTTA TGCCTCACAA TTTATGCACA TTTCGGGCTT     840

GGAGATTTAT CCTCTATATT ACATGCCTGT TTTTTAAAG GATATAATGT TTAACAAATA      900

ATTTTTTATC AATGCTATTG TATATTCTCC AGCTAACCGT TGTTTCGAAA ACATCACCTA     960

GCATTTAAA ATTCACAAAA TCTTGCTTCC TTATAATCAA GAAGATTTTT CAGATGCTCT     1020

GCGAAATCGA ATGCCGCGCT TTGAGCACGG CACACACGAG GCTCATCCAC GACTTTGAAC    1080

CACGTGACGC ATTGACTTAT TTAGAAGGCA AAAACATTTT CACAGAAGAT CATTCTGAAC    1140

TTATCAGTAA AATGTCAACT CGCCTCGAGA GGATCGCCAA TTTTCTTCGA ATCTATCGAC    1200

GTCAAGCTTC TGAACTTGGA CCACTCATCG ACTTTTTCAA CTACAACAAT CAAAGTCACC    1260

TTGCTGATTT CCTCGAAGAC TACATCGATT TTGCGATAAA TGAGCCAGAT CTACTTCGTC    1320

CAGTAGTGAT TGCTCCACAA TTTTCCCGAC AAATGCTCGA TAGGAAACTA TTGCTTGGGA    1380

ATGTTCCAAA ACAAATGACA TGCTATATTC GAGAGTATCA CGTGGATCGA GTGATCAAAA    1440

AGCTCGACGA GATGTGTGAT TTAGGTGAGA AAACTGGAAG CTCTCGTGTT TATTATAATC    1500

TTGCTTAAAC TTCAGACTCC TTTTTTCTGT TTCTACACGG CCGAGCTGGA TCCGGAAAAT    1560

CAGTAATTGC ATCACAAGCT CTTTCGAAAT CTGACCAACT TATTGGAATG TGAGTGGTAT    1620

TATCTGAATC TACGGATCTT CATTCTATTA CAGAAATTAT GATTCAATCG TTTGGCTCAA    1680

AGATAGTGGA ACAGCTCCAA AATCTACATT CGATTTATTT ACGGATATTT TGCTGATGCT    1740

AAAGTGAGTG AATAGAGTGC ATGTAACATT CAGCATGATT TTGAAATTAT GAAAATTTGA    1800
```

-continued

```
CCTGGTTAGC TTTTAATTTG ATATTTCGTG ACGCTTGCAT GTTTTGTGTG TTTGAAGACG   1860

AGCCCGTGTT GTGAGCGACA CGGATGACTC GCATTCGATC ACCGACTTCA TTAACCGTGT   1920

TCTTTCAAGA AGCGAAGACG ATCTTCTCAA TTTCCCATCG GTGGAGCATG TCACGTCAGT   1980

TGTACTCAAA AGGATGGTAA GTTGCTTGCC GATTCTGGTA CAATATCTTA AATTATTGGT   2040

TTTTAGATCT GCAACGCACT CATTGATCGT CCAAATACTT TATTCGTATT TGATGACGTA   2100

GTTCAAGAAG AAACAATTCG TTGGGCTCAG GAGCTACGTC TTCGATGTCT TGTAACTACT   2160

CGTGACGTGG AAATATCAAA TGCTGCTTCT CAAACATGCG AATTCATTGA AGTGACATCA   2220

TTGGAAATCG ATGAATGTTA TGATTTTCTA GAAGCTTATG GAATGCCGAT GCCTGTTGGA   2280

GAAAAGAAG AAGATGTGCT TAATAAAACA ATCGAACTAA GCAGTGGAAA TCCAGCAACG    2340

CTTATGATGT TTTTCAAGTC TTGTGAACCG AAAACATTTG AAAAGTGAGT GGGACATACC   2400

AATTTGAGAC TTTTAAAATA ATTTATTCTA CAATAAAAGT TAATCAAAAA GTTTCATAGC   2460

TGATTGTCTT TAAATTTTAC GAATTGAGGA TCAAAATCAA GAATTAGGAT CCTGGCACGA   2520

GAGAAAACTG TGTAGCTACC GTACCCGAGA GATTTTCTTG ATATTTGCCA TCGATTTAAT   2580

TTTTTAAGAA AATTATCGTT TTACATAATT GAACAAGAGA TACACGGTCT CGACCCGACG   2640

GAAATTTTTT AAATGAAAGC GAGTATGAGC CTGTTTTCAT TATTTTTCGA TTTTCTCTTG   2700

TTGTTTCTTT TTATTTAAAG CCTTTTATTT TGAAACAAGT CTAAAAATAT TAAAAACTGA   2760

ATAAATATT TAAAAAAAAT CAAGTAAAAT AGAAAAACAG CAAGGCTGGA GACTACTGTA    2820

CTTCTTAAAT CCGCATACTC TTTTTATTTA ATCATTTTCC GGAATGTCGA AACGAAATAA   2880

TACATTTTTA GTCCAAAATC GCTAGGTATA TTCTTAAAAT TATCAAACAT TTGCATTCA    2940

GAATGGCACA GCTTAATAAC AAATTGGAAA GTCGAGGATT AGTCGGTGTT GAATGTATCA   3000

CCCCTTACTC GTACAAGTCA CTCGCAATGG CTCTTCAAAG ATGTGTTGAA GTTTTGTCAG   3060

ATGAGGATCG AAGTGCTCTT GCTTTCGCAG TTGTGATGCC TCCTGGAGTT GATATACCCG   3120

TCAAGCTATG GTCATGTGTT ATTCCAGTTG ATATTTGTTC AAATGAAGAA GAACAATTGG   3180

ATGATGAAGT TGCGGATCGG TTGAAAAGAC TCAGCAAGTA TGAGTCTTGA AATTTGAAGA   3240

TTTAAATTAA CACTTAAAAT TTCAGACGTG GAGCTCTTCT CAGTGGAAAA CGAATGCCCG   3300

TTTTGACATT CAAAATTGAT CATATTATCC ATATGTTCTT GAAACACGTC GTTGATGCAC   3360

AAACTATCGC CGTATGCTGA AAATGTCTCA ACTTTCAATT AAATTTTAAA TTTTCAGAAT   3420

GGAATCTCAA TTCTCGAGCA GCGTCTTCTT GAAATAGGAA ACAATAATGT ATCAGTACCG   3480

GAGCGACATA TACCATCACA TTTCCAAAAA TTCCGTCGTT CATCAGCCAG TGAGATGTAT   3540

CCAAAAACTA CAGAAGAAAC TGTGATCCGT CCTGAAGACT TCCCAAAGTT CATGCAATTG   3600

CACCAGAAAT TCTATGACTC CCTCAAAAAT TTTGCATGCT GTTAAAACCT ATCGTGTACA   3660

ATATTGCCTG TATATTCCCC TCGAAATACG TTTATACTTT TTCGCACGAG TTTTCTCATT   3720

TTTTCATTTG TACTTGTTTT ATTTCTCTCC AAAATTTCAG ATCTATCCCA AATGTTCTTA   3780

AATTTAATGT TTTCTACAGA TACTCAACAC ATCTTGTTTC ATCTCATCCT TGCTTTTTTT   3840

TTTCAAATAT ATTCAGTTTC TTTTATAATT TTAATTAATC GAATTAATAC ATTCACGTAA   3900

AGAATTTCGT GGACTATTAT TTTATCGCAT CCAAATGATT TATTCCCTAT TGTTCGAAAC   3960

TTCCAAATTG ATCATTTTTA AACACGCCTC ATTAAATTGA AAGTCGTACT TTTAGTCTCG   4020

AACATGAAGT AAGTTATTTT CTGTGTTCTA AATTCAAAGT GCATTCCAAA AGGACATTTG   4080

ATGAGTTTTC ACGAAAACCG TAATTTTTAC AATTTCCTTT CAGTTTTGAA GATGTTCGAT   4140
```

-continued

```
TTCTTTCCTC TGTTGGCGTC ATTACTACAT TTGCTTTGCT GCTTCACTTT ATCGAGATTC    4200

TTGCCATCAA TGGAGTTCCA TCTAGACCGA TAGCAGTCTT CATATCATTA TCCCTGTATA    4260

TTGTACTGTT TCAGTATTTT AACTTATCGA TTACGTACTA TATTCAGTGG TTCACTGTTT    4320

TCGGTCAATG GGTGACACGT GCTCGACGAN NAATTTTCAA CGAACGCAAT CTCCTAGTCA    4380

CTTATCAACC AAGAGCCCTC ACCCATG                                        4407
```

(2) INFORMATION FOR SEQ ID NO: 2:

(i) SEQUENCE CHARACTERISTICS:
        (A) LENGTH: 549 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 2:

```
Met Leu Cys Glu Ile Glu Cys Arg Ala Leu Ser Thr Ala His Thr Arg
1               5                   10                  15

Leu Ile His Asp Phe Glu Pro Arg Asp Ala Leu Thr Tyr Leu Glu Gly
            20                  25                  30

Lys Asn Ile Phe Thr Glu Asp His Ser Glu Leu Ile Ser Lys Met Ser
        35                  40                  45

Thr Arg Leu Glu Arg Ile Ala Asn Phe Leu Arg Ile Tyr Arg Arg Gln
    50                  55                  60

Ala Ser Glu Leu Gly Pro Leu Ile Asp Phe Phe Asn Tyr Asn Asn Gln
65                  70                  75                  80

Ser His Leu Ala Asp Phe Leu Glu Asp Tyr Ile Asp Phe Ala Ile Asn
                85                  90                  95

Glu Pro Asp Leu Leu Arg Pro Val Val Ile Ala Pro Gln Phe Ser Arg
            100                 105                 110

Gln Met Leu Asp Arg Lys Leu Leu Gly Asn Val Pro Lys Gln Met
        115                 120                 125

Thr Cys Tyr Ile Arg Glu Tyr His Val Asp Arg Val Ile Lys Lys Leu
    130                 135                 140

Asp Glu Met Cys Asp Leu Asp Ser Phe Phe Leu Phe Leu His Gly Arg
145                 150                 155                 160

Ala Gly Ser Gly Lys Ser Val Ile Ala Ser Gln Ala Leu Ser Lys Ser
                165                 170                 175

Asp Gln Leu Ile Gly Ile Asn Tyr Asp Ser Ile Val Trp Leu Lys Asp
            180                 185                 190

Ser Gly Thr Ala Pro Lys Ser Thr Phe Asp Leu Phe Thr Asp Ile Leu
        195                 200                 205

Leu Met Leu Lys Ser Glu Asp Asp Leu Leu Asn Phe Pro Ser Val Glu
    210                 215                 220

His Val Thr Ser Val Val Leu Lys Arg Met Ile Cys Asn Ala Leu Ile
225                 230                 235                 240

Asp Arg Pro Asn Thr Leu Phe Val Phe Asp Asp Val Val Gln Glu Glu
                245                 250                 255

Thr Ile Arg Trp Ala Gln Glu Leu Arg Leu Arg Cys Leu Val Thr Thr
            260                 265                 270

Arg Asp Val Glu Ile Ser Asn Ala Ala Ser Gln Thr Cys Glu Phe Ile
        275                 280                 285

Glu Val Thr Ser Leu Glu Ile Asp Glu Cys Tyr Asp Phe Leu Glu Ala
    290                 295                 300
```

```
Tyr Gly Met Pro Met Pro Val Gly Glu Lys Glu Glu Asp Val Leu Asn
305                 310                 315                 320

Lys Thr Ile Glu Leu Ser Ser Gly Asn Pro Ala Thr Leu Met Met Phe
            325                 330                 335

Phe Lys Ser Cys Glu Pro Lys Thr Phe Glu Lys Met Ala Gln Leu Asn
            340                 345                 350

Asn Lys Leu Glu Ser Arg Gly Leu Val Gly Val Glu Cys Ile Thr Pro
            355                 360                 365

Tyr Ser Tyr Lys Ser Leu Ala Met Ala Leu Gln Arg Cys Val Glu Val
370                 375                 380

Leu Ser Asp Glu Asp Arg Ser Ala Leu Ala Phe Ala Val Val Met Pro
385                 390                 395                 400

Pro Gly Val Asp Ile Pro Val Lys Leu Trp Ser Cys Val Ile Pro Val
                405                 410                 415

Asp Ile Cys Ser Asn Glu Glu Glu Gln Leu Asp Asp Glu Val Ala Asp
                420                 425                 430

Arg Leu Lys Arg Leu Ser Lys Arg Gly Ala Leu Leu Ser Gly Lys Arg
            435                 440                 445

Met Pro Val Leu Thr Phe Lys Ile Asp His Ile Ile His Met Phe Leu
            450                 455                 460

Lys His Val Val Asp Ala Gln Thr Ile Ala Asn Gly Ile Ser Ile Leu
465                 470                 475                 480

Glu Gln Arg Leu Leu Glu Ile Gly Asn Asn Asn Val Ser Val Pro Glu
                485                 490                 495

Arg His Ile Pro Ser His Phe Gln Lys Phe Arg Arg Ser Ser Ala Ser
                500                 505                 510

Glu Met Tyr Pro Lys Thr Thr Glu Glu Thr Val Ile Arg Pro Glu Asp
            515                 520                 525

Phe Pro Lys Phe Met Gln Leu His Gln Lys Phe Tyr Asp Ser Leu Lys
530                 535                 540

Asn Phe Ala Cys Cys
545

(2) INFORMATION FOR SEQ ID NO: 3:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 3:

Asp Gln Asp Lys Ser Gly Phe Ile Glu Glu Asp Glu
1               5                   10

(2) INFORMATION FOR SEQ ID NO: 4:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 4:

Asp Gln Asp Lys Asp Asp Phe Ile Gly Glu Asp Glu
```

```
           1               5                   10
```

(2) INFORMATION FOR SEQ ID NO: 5:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 5:

```
Asp Ser Asp Gly Asp His Lys Ile Gly Val Asp Glu
1               5                   10
```

(2) INFORMATION FOR SEQ ID NO: 6:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 6:

```
Asp Ile Asn Lys Asp Asp Val Val Ser Trp Glu Glu
1               5                   10
```

(2) INFORMATION FOR SEQ ID NO: 7:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 7:

```
Ala Lys Glu Gly Asp Pro Gln Leu Ser Lys Glu Glu
1               5                   10
```

(2) INFORMATION FOR SEQ ID NO: 8:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 8:

```
Asp Lys Asn Gly Asp Gly Glu Cys Ser Phe Glu Glu
1               5                   10
```

(2) INFORMATION FOR SEQ ID NO: 9:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 9:

-continued

```
Asp Ala Asp Gly Gly Gly Asp Ile Ser Val Lys Glu
1               5                   10
```

(2) INFORMATION FOR SEQ ID NO: 10:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 10:

```
Asp Glu Asp Gly Ser Gly Thr Ile Asp Phe Glu Glu
1               5                   10
```

(2) INFORMATION FOR SEQ ID NO: 11:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO: 11:

```
Asp Arg Asn Ala Asp Gly Tyr Ile Asp Ala Glu Glu
1               5                   10
```

(2) INFORMATION FOR SEQ ID NO: 12:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 12:

```
Asp Lys Asn Asn Asp Gly Arg Ile Asp Phe Asp Glu
1               5                   10
```

(2) INFORMATION FOR SEQ ID NO: 13:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 13:

```
Asp Lys Asp Gly Asn Gly Thr Ile Thr Thr Lys Glu
1               5                   10
```

(2) INFORMATION FOR SEQ ID NO: 14:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 14:

Leu Gly Glu Asp Asn Ile Asn Val Val Glu Gly Asn Glu
1               5                   10

(2) INFORMATION FOR SEQ ID NO: 15:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 15:

Asp Asn Asp Asn Asp Lys Phe Glu Gly Asn Cys Ala Glu
1               5                   10

(2) INFORMATION FOR SEQ ID NO: 16:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 16:

Gly Val Asp Pro Ser Arg Lys Glu Asn His Leu Ser
1               5                   10

(2) INFORMATION FOR SEQ ID NO: 17:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 17:

Asp Leu Asn Lys Asp Gly Gln Ile Gln Ile Glu
1               5                   10

(2) INFORMATION FOR SEQ ID NO: 18:

(i) SEQUENCE CHARACTERISTICS:
        (A) LENGTH: 7653 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

```
AGATCTGAAA TAAGGTGATA AATTAATAAA TTAAGTGTAT TTCTGAGGAA ATTTGACTGT      60

TTTAGCACAA TTAATCTTGT TTCAGAAAAA AAGTCCAGTT TTCTAGATTT TTCCGTCTTA     120

TTGTCGAATT AATATCCCTA TTATCACTTT TTCATGCTCA TCCTCGAGCG GCACGTCCTC     180

AAAGAATTGT GAGAGCAAAC GCGCTCCCAT TGACCTCCAC ACTCAGCCGC CAAAACAAAC     240

GTTCGAACAT TCGTGTGTTG TGCTCCTTTT CCGTTATCTT GCAGTCATCT TTTGTCGTTT     300

TTTTCTTTGT TCTTTTTGTT GAACGTGTTG CTAAGCAATT ATTACATCAA TTGAAGAAAA     360

GGCTCGCCGA TTTATTGTTG CCAGAAAGAT TCTGAGATTC TCGAAGTCGA TTTTATAATA     420
```

-continued

| | |
|---|---|
| TTTAACCTTG GTTTTTGCAT TGTTTCGTTT AAAAAAACCA CTGTTTATGT GAAAAACGAT | 480 |
| TAGTTTACTA ATAAAACTAC TTTTAAACCT TTACCTTTAC CTCACCGCTC CGTGTTCATG | 540 |
| GCTCATAGAT TTTCGATACT CAAATCCAAA AATAAATTTA CGAGGGCAAT TAATGTGAAA | 600 |
| CAAAAACAAT CCTAAGATTT CCACATGTTT GACCTCTCCG GCACCTTCTT CCTTAGCCCC | 660 |
| ACCACTCCAT CACCTCTTTG GCGGTGTTCT TCGAAACCCA CTTAGGAAAG CAGTGTGTAT | 720 |
| CTCATTTGGT ATGCTCTTTT CGATTTTATA GCTCTTTGTC GCAATTTCAA TGCTTTAAAC | 780 |
| AATCCAAATC GCATTATATT TGTGCATGGA GGCAAATGAC GGGGTTGGAA TCTTAGATGA | 840 |
| GATCAGGAGC TTTCAGGGTA AACGCCCGGT TCATTTTGTA CCACATTTCA TCATTTTCCT | 900 |
| GTCGTCCTTG GTATCCTCAA CTTGTCCCGG TTTTGTTTTC GGTACACTCT TCCGTGATGC | 960 |
| CACCTGTCTC CGTCTCAATT ATCGTTTAGA AATGTGAACT GTCCAGATGG GTGACTCATA | 1020 |
| TTGCTGCTGC TACAATCCAC TTTCTTTTCT CATCGGCAGT CTTACGAGCC ATCATAAAC | 1080 |
| TTTTTTTTCC GCGAAATTTG CAATAAACCG GCCAAAAACT TTCTCCAAAT TGTTACGCAA | 1140 |
| TATATACAAT CCATAAGAAT ATCTTCTCAA TGTTTATGAT TTCTTCGCAG CACTTTCTCT | 1200 |
| TCGTGTGCTA ACATCTTATT TTTATAATAT TTCCGCTAAA ATTCCGATTT TTGAGTATTA | 1260 |
| ATTTATCGTA AAATTATCAT AATAGCACCG AAAACTACTA AAAATGGTAA AAGCTCCTTT | 1320 |
| TAAATCGGCT CGACATTATC GTATTAAGGA ATCACAAAAT TCTGAGAATG CGTACTGCGC | 1380 |
| AACATATTTG ACGGCAAAAT ATCTCGTAGC GAAAACTACA GTAATTCTTT AAATGACTAC | 1440 |
| TGTAGCGCTT GTGTCGATTT ACGGGCTCAA TTTTTGAAAA TAATTTTTTT TTTCGAATTT | 1500 |
| TGATAACCCG TAAATCGTCA CAACGCTACA GTAGTCATTT AAAGGATTAC TGTAGTTCTA | 1560 |
| GCTACGAGAT ATTTTGCGCG CCAAATATGA CTGTAATACG CATTCTCTGA ATTTGTGTT | 1620 |
| TCCGTAATAA TTTCACAAGA TTTTGGCATT CCACTTTAAA GGCGCACAGG ATTTATTCCA | 1680 |
| ATGGGTCTCG GCACGCAAAA AGTTTGATAG ACTTTTAAAT TCTCCTTGCA TTTTTAATTC | 1740 |
| AATTACTAAA ATTTTCGTGA ATTTTTCTGT TAAAATTTTT AAAATCAGTT TTCTAATATT | 1800 |
| TTCCAGGCTG ACAAACAGAA ACAAAAACAC AACAAACATT TTAAAAATCA GTTTTCAAAT | 1860 |
| TAAAAATAAC GATTTCTCAT TGAAAATTGT GTTTTATGTT TGCGAAAATA AAAGAGAACT | 1920 |
| GATTCAAAAC AATTTTAACA AAAAAAAACC CCAAAATTCG CCAGAAATCA AGATAAAAAA | 1980 |
| TTCAAGAGGG TCAAAATTTT CCGATTTTAC TGACTTTCAC CTTTTTTTTC GTAGTTCAGT | 2040 |
| GCAGTTGTTG GAGTTTTTGA CGAAAACTAG GAAAAAAATC GATAAAAATT ACTCAAATCG | 2100 |
| AGCTGAATTT TGAGGACAAT GTTTAAAAAA AAACACTATT TTTCCAATAA TTTCACTCAT | 2160 |
| TTTCAGACTA AATCGAAAAT CAAATCGTAC TCTGACTACG GGTCAGTAGA GAGGTCAACC | 2220 |
| ATCAGCCGAA GATGATGCGT CAAGATAGAA GGAGCTTGCT AGAGAGGAAC ATTATGATGT | 2280 |
| TCTCTAGTCA TCTAAAAGTC GATGAAATTC TCGAAGTTCT CATCGCAAAA CAAGTGTTGA | 2340 |
| ATAGTGATAA TGGAGATATG ATTAATGTGA GTTTTAATC GAATAATAAT TTTAAAAAAA | 2400 |
| AATTGATAAT ATAAAGAATA TTTTTGCAGT CATGTGGAAC GGTTCGCGAG AAGAGACGGG | 2460 |
| AGATCGTGAA AGCAGTGCAA CGACGGGGAG ATGTGGCGTT CGACGCGTTT TATGATGCTC | 2520 |
| TTCGCTCTAC GGGACACGAA GGACTTGCTG AAGTTCTTGA ACCTCTCGCC AGATCGTAGG | 2580 |
| TTTTTAAAGT TCGGCGCAAA AGCAAGGGTC TCACGGAAAA AAGAGGCGGA TCGTAATTTT | 2640 |
| GCAACCCACC GGCACGGTTT TTTCCTCCGA AAATCGGAAA TTATGCACTT TCCCAAATAT | 2700 |
| TTGAAGTGAA ATATATTTTA TTTACTGAAA GCTCGAGTGA TTATTTATTT TTTAACACTA | 2760 |
| ATTTTCGTGG CGCAAAAGGC CATTTTGTAG ATTTGCCGAA AATACTTGTC ACACACACAC | 2820 |

-continued

```
ACACACATCT CCTTCAAATA TCCCTTTTTC CAGTGTTGAC TCGAATGCTG TCGAATTCGA        2880

GTGTCCAATG TCACCGGCAA GCCATCGTCG GAGCCGCGCA TTGAGCCCCG CCGGCTACAC        2940

TTCACCGACC CGAGTTCACC GTGACAGCGT CTCTTCAGTG TCATCATTCA CTTCTTATCA        3000

GGATATCTAC TCAAGAGCAA GATCTCGTTC TCGATCGCGT GCACTTCATT CATCGGATCG        3060

ACACAATTAT TCATCTCCTC CAGTCAACGC ATTTCCCAGC CAACCTTGTA TGTTGATGCG        3120

AACACTAAAT TCTGAGAATG CGCATTACTC AACATATTTG ACGCGCAAAT ATCTCGTAGC        3180

GAAAAATACA GTAACCCTTT AAATGACTAT TGTAGTGTCG ATTTACGGGC TCGATTTTCG        3240

AAACGAATAT ATGCTCGAAT TGTGACAACG AATTTTAATT TGTCATTTTT GTGTTTTCTT        3300

TTGATATTTT TGATCAATTA ATAAATTATT TCCGTAAACA GACACCAGCG CTACAGTACT        3360

CTTTTAAAGA GTTACAGTAG TTTTCGCTTC AAGATATTTT GAAAGAATT TTAAACATTT        3420

TGAAAAAAAA TCATCTAACA TGTGCCAAAA CGCTTTTTTC AAGTTTCGCA GATTTTTTGA        3480

TTTTTTTCAT TCAAGATATG CTTATTAACA CATATAATTA TCATTAATGT GAATTTCTTG        3540

TAGAAATTTT GGGCTTTTCG TTCTAGTATG CTCTACTTTT GAAATTGCTC AACGAAAAAA        3600

TCATGTGGTT TGTTCATATG AATGACGAAA AATAGCAATT TTTTATATAT TTTCCCCTAT        3660

TCATGTTGTG CAGAAAAATA GTAAAAAAGC GCATGCATTT TTCGACATTT TTTACATCGA        3720

ACGACAGCTC ACTTCACATG CTGAAGACGA GAGACGCGGA GAAATACCAC ACATCTTTCT        3780

GCGTCTCTCG TCTTCAGCAT GTGAAATGGG ATCTCGGTCG ATGTAAAAAA ATGTCGAATA        3840

ATGTAAAAAA TGCATGCGTT TTTTTACACT TTTCTGCACA AATGAATAGG GGGAAAATGT        3900

ATTAAAATAC ATTTTTTGTA TTTTTCAACA TCACATGATT AACCCCATTA TTTTTTCGTT        3960

GAGCAACTTA AAAAGTAGAG AATATTAGAG CGAAAACCAA AATTTCTTCA AGATATTACC        4020

TTTATTGATA ATTATAGATG TTAATAAGCA TATCTTGAAT GAAAGTCAGC AAAAAATATGT       4080

GCGAAACACC TGAAAAAAAT CAAAAATTCT GCGAAAATTG AAAAAATGCA TTAAAATACA        4140

TTTTTGCATT TTTCTACATC ACATGAATGT AGAAAATTAA AAGGGAAATC AAAATTTCTA        4200

GAGGATATAA TTGAATGAAA CATTGCGAAA TTAAAATGTG CGAAACGTCA AAAAAGAGGA        4260

AATTTGGGTA TCAAAATCGA TCCTAAAACC AACACATTTC AGCATCCGCC AACTCTTCAT        4320

TCACCGGATG CTCTTCTCTC GGATACAGTT CAAGTCGTAA TCGCTCATTC AGCAAAGCTT        4380

CTGGACCAAC TCAATACATA TTCCATGAAG AGGATATGAA CTTTGTCGAT GCACCAACCA        4440

TAAGCCGTGT TTTCGACGAG AAAACCATGT ACAGAAACTT CTCGAGTCCT CGTGGAATGT        4500

GCCTCATCAT AAATAATGAA CACTTTGAGC AGATGCCAAC ACGGAATGGT ACCAAGGCCG        4560

ACAAGGACAA TCTTACCAAT TTGTTCAGAT GCATGGGCTA TACGGTTATT TGCAAGGACA        4620

ATCTGACGGG AAGGGTACGG CGAAATTATA TTACCCAAAC GCGAAATTTG CCATTTTGCG        4680

CCGAAAATGT GGCGCCCGGT CTCGACACGA CAATTTGTGT TAAATGCAAA AATGTATAAT        4740

TTTGCAAAAA ACAAAATTTT GAACTTCCGC GAAAATGATT TACCTAGTTT CGAAATTTTC        4800

GTTTTTTCCG GCTACATTAT GTGTTTTTTC TTAGTTTTTC TATAATATTT GATGTAAAAA        4860

ACCGTTGTA AATTTTCAGA CAATTTTCCG CATACAAAAC TTGATAGCAC GAAATCAATT        4920

TTCTGAATTT TCAAAATTAT CCAAAAATGC ACAATTTAAA ATTTGTGAAA ATTGGCAAAC        4980

GGTGTTTCAA TATGAAATGT ATTTTTAAAA ACTTTAAAAA CCACTCCGGA AAAGCAATAA        5040

AAATCAAAAC AACGTCACAA TTCAAATTCA AAAGTTATTC ATCCGATTTG TTTATTTTTG        5100

CAAAATTTGA AAAAATCATG AAGGATTTAG AAAAGTTTTA TAACATTTTT TCTAGATTTT        5160
```

```
TCAAAATTTT TTTTAACAAA TCGAGAAAAA GAGAATGAAA AATCGATTTT AAAAATATCC    5220

ACAGCTTCGA GAGTTTGAAA TTACAGTACT CCTTAAAGGC GCACACCCCA TTTGCATTGG    5280

ACCAAAAATT TGTCGTGTCG AGACCAGGTA CCGTAGTTTT TGTCGCAAAA ATTGCACCAT    5340

TGGACAATAA ACCTTCCTAA TCACCAAAAA GTAAAATTGA AATCTTCGAA AAGCCAAAAA    5400

ATTCAAAAAA AAAGTCGAAT TTCGATTTTT TTTTTGGTTT TTTGGTCCCA AAAACCAAAA    5460

AAATCAATTT TCTGCAAAAT ACCAAAAAGA AACCCGAAAA AATTTCCCAG CCTTGTTCCT    5520

AATGTAAACT GATATTTAAT TTCCAGGGAA TGCTCCTGAC AATTCGAGAC TTTGCCAAAC    5580

ACGAATCACA CGGAGATTCT GCGATACTCG TGATTCTATC ACACGGAGAA GAGAATGTGA    5640

TTATTGGAGT TGATGATATA CCGATTAGTA CACACGAGAT ATATGATCTT CTCAACGCGG    5700

CAAATGCTCC CCGTCTGGCG AATAAGCCGA AAATCGTTTT TGTGCAGGCT TGTCGAGGCG    5760

GTTCGTTTTT TATTTTAATT TTAATATAAA TATTTTAAAT AAATTCATTT TCAGAACGTC    5820

GTGACAATGG ATTCCCAGTC TTGGATTCTG TCGACGGAGT TCCTGCATTT CTTCGTCGTG    5880

GATGGGACAA TCGAGACGGG CCATTGTTCA ATTTTCTTGG ATGTGTGCGG CCGCAAGTTC    5940

AGGTTGCAAT TTAATTTCTT GAATGAGAAT ATTCCTTCAA AAAATCTAAA ATAGATTTTT    6000

ATTCCAGAAA GTCCCGATCG AAAAATTGCG ATATAATTAC GAAATTTGTG ATAAAATGAC    6060

AAACCAATCA GCATCGTCGA TCTCCGCCCA CTTCATCGGA TTGGTTTGAA AGTGGGCGGA    6120

GTGAATTGCT GATTGGTCGC AGTTTTCAGT TTAGAGGGAA TTTAAAAATC GCCTTTTCGA    6180

AAATTAAAAA TTGATTTTTT CAATTTTTTC GAAAATATT CCGATTATTT TATATTCTTT     6240

GGAGCGAAAG CCCCGTCCTG TAAACATTTT TAAATGATAA TTAATAAATT TTTGCAGCAA    6300

GTGTGGAGAA AGAAGCCGAG CCAAGCTGAC ATTCTGATTC GATACGCAAC GACAGCTCAA    6360

TATGTTTCGT GGAGAAACAG TGCTCGTGGA TCATGGTTCA TTCAAGCCGT CTGTGAAGTG    6420

TTCTCGACAC ACGCAAAGGA TATGGATGTT GTTGAGCTGC TGACTGAAGT CAATAAGAAG    6480

GTCGCTTGTG GATTTCAGAC ATCACAGGGA TCGAATATTT TGAAACAGAT GCCAGAGGTA    6540

CTTGAAACAA ACAATGCATG TCTAACTTTT AAGGACACAG AAAAATAGGC AGAGGCTCCT    6600

TTTGCAAGCC TGCCGCGCGT CAACCTAGAA TTTTAGTTTT TAGCTAAAAT GATTGATTTT    6660

GAATATTTTA TGCTAATTTT TTTGCGTTAA ATTTTGAAAT AGTCACTATT TATCGGGTTT    6720

CCAGTAAAAA ATGTTTATTA GCCATTGGAT TTTACTGAAA ACGAAAATTT GTAGTTTTTC    6780

AACGAAATTT ATCGATTTTT AAATGTAAAA AAAAATAGCG AAAATTACAT CAACCATCAA    6840

GCATTTAAGC CAAAATTGTT AACTCATTTA AAAATTAATT CAAAGTTGTC CACGAGTATT    6900

ACACGGTTGG CGCGCGGCAA GTTTGCAAAA CGACGCTCCG CCTCTTTTTC TGTGCGGCTT    6960

GAAAACAAGG GATCGGTTTA GATTTTTCCC CAAAATTTAA ATTAAATTTC AGATGACATC    7020

CCGCCTGCTC AAAAGTTCT ACTTTTGGCC GGAAGCACGA AACTCTGCCG TCTAAAATTC      7080

ACTCGTGATT CATTGCCCAA TTGATAATTG TCTGTATCTT CTCCCCCAGT TCTCTTTCGC    7140

CCAATTAGTT TAAAACCATG TGTATATTGT TATCCTATAC TCATTTCACT TTATCATTCT    7200

ATCATTTCTC TTCCCATTTT CACACATTTC CATTTCTCTA CGATAATCTA AAATTATGAC    7260

GTTTGTGTCT CGAACGCATA ATAATTTTAA TAACTCGTTT TGAATTTGAT TAGTTGTTGT    7320

GCCCAGTATA TATGTATGTA CTATGCTTCT ATCAACAAAA TAGTTTCATA GATCATCACC    7380

CCAACCCCAC CAACCTACCG TACCATATTC ATTTTTGCCG GGAATCAATT TCGATTAATT    7440

TTAACCTATT TTTTCGCCAC AAAAAATCTA ATATTTGAAT TAACGAATAG CATTCCCATC    7500

TCTCCCGTGC CGGAATGCCT CCCGGCCTTT TAAAGTTCGG AACATTTGGC AATTATGTAT    7560
```

```
AAATTTGTAG GTCCCCCCCA TCATTTCCCG CCCATCATCT CAAATTGCAT TCTTTTTTCG      7620

CCGTGATATC CCGATTCTGG TCAGCAAAGA TCT                                  7653
```

(2) INFORMATION FOR SEQ ID NO: 19:

(i) SEQUENCE CHARACTERISTICS:
        (A) LENGTH: 503 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 19:

```
Met Met Arg Gln Asp Arg Arg Ser Leu Leu Glu Arg Asn Ile Met Met
1               5                   10                  15

Phe Ser Ser His Leu Lys Val Asp Glu Ile Leu Glu Val Leu Ile Ala
                20                  25                  30

Lys Gln Val Leu Asn Ser Asp Asn Gly Asp Met Ile Asn Ser Cys Gly
            35                  40                  45

Thr Val Arg Glu Lys Arg Arg Glu Ile Val Lys Ala Val Gln Arg Arg
50                  55                  60

Gly Asp Val Ala Phe Asp Ala Phe Tyr Asp Ala Leu Arg Ser Thr Gly
65                  70                  75                  80

His Glu Gly Leu Ala Glu Val Leu Glu Pro Leu Ala Arg Ser Val Asp
                85                  90                  95

Ser Asn Ala Val Glu Phe Glu Cys Pro Met Ser Pro Ala Ser His Arg
                100                 105                 110

Arg Ser Arg Ala Leu Ser Pro Ala Gly Tyr Thr Ser Pro Thr Arg Val
            115                 120                 125

His Arg Asp Ser Val Ser Ser Val Ser Ser Phe Thr Ser Tyr Gln Asp
130                 135                 140

Ile Tyr Ser Arg Ala Arg Ser Arg Ser Arg Ser Arg Ala Leu His Ser
145                 150                 155                 160

Ser Asp Arg His Asn Tyr Ser Ser Pro Pro Val Asn Ala Phe Pro Ser
                165                 170                 175

Gln Pro Ser Ser Ala Asn Ser Ser Phe Thr Gly Cys Ser Ser Leu Gly
            180                 185                 190

Tyr Ser Ser Arg Asn Arg Ser Phe Ser Lys Ala Ser Gly Pro Thr
            195                 200                 205

Gln Tyr Ile Phe His Glu Glu Asp Met Asn Phe Val Asp Ala Pro Thr
            210                 215                 220

Ile Ser Arg Val Phe Asp Glu Lys Thr Met Tyr Arg Asn Phe Ser Ser
225                 230                 235                 240

Pro Arg Gly Met Cys Leu Ile Ile Asn Asn Glu His Phe Glu Gln Met
                245                 250                 255

Pro Thr Arg Asn Gly Thr Lys Ala Asp Lys Asp Asn Leu Thr Asn Leu
                260                 265                 270

Phe Arg Cys Met Gly Tyr Thr Val Ile Cys Lys Asp Asn Leu Thr Gly
            275                 280                 285

Arg Gly Met Leu Leu Thr Ile Arg Asp Phe Ala Lys His Glu Ser His
            290                 295                 300

Gly Asp Ser Ala Ile Leu Val Ile Leu Ser His Gly Glu Glu Asn Val
305                 310                 315                 320

Ile Ile Gly Val Asp Asp Ile Pro Ile Ser Thr His Glu Ile Tyr Asp
```

-continued

```
                  325                 330                 335
Leu Leu Asn Ala Ala Asn Ala Pro Arg Leu Ala Asn Lys Pro Lys Ile
                340                 345                 350
Val Phe Val Gln Ala Cys Arg Gly Glu Arg Arg Asp Asn Gly Phe Pro
                355                 360                 365
Val Leu Asp Ser Val Asp Gly Val Pro Ala Phe Leu Arg Arg Gly Trp
                370                 375                 380
Asp Asn Arg Asp Gly Pro Leu Phe Asn Phe Leu Gly Cys Val Arg Pro
385                 390                 395                 400
Gln Val Gln Val Trp Arg Lys Lys Pro Ser Gln Ala Asp Ile Leu
                405                 410                 415
Ile Arg Tyr Ala Thr Thr Ala Gln Tyr Val Ser Trp Arg Asn Ser Ala
                420                 425                 430
Arg Gly Ser Trp Phe Ile Gln Ala Val Cys Glu Val Phe Ser Thr His
                435                 440                 445
Ala Lys Asp Met Asp Val Val Glu Leu Leu Thr Glu Val Asn Lys Lys
                450                 455                 460
Val Ala Cys Gly Phe Gln Thr Ser Gln Gly Ser Asn Ile Leu Lys Gln
465                 470                 475                 480
Met Pro Glu Met Thr Ser Arg Leu Leu Lys Lys Phe Tyr Phe Trp Pro
                485                 490                 495
Glu Ala Arg Asn Ser Ala Val
                500

(2) INFORMATION FOR SEQ ID NO: 20:

(i) SEQUENCE CHARACTERISTICS:
        (A) LENGTH: 505 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 20:

Met Met Arg Gln Asp Arg Trp Leu Leu Glu Arg Asn Ile Leu Glu Phe
1               5                   10                  15
Ser Ser Lys Leu Gln Ala Asp Leu Ile Leu Asp Val Leu Ile Ala Lys
                20                  25                  30
Gln Val Leu Asn Ser Asp Asn Gly Asp Val Ile Asn Ser Cys Arg Thr
                35                  40                  45
Glu Arg Asp Asn Glu Lys Glu Ile Val Lys Ala Val Gln Arg Arg Gly
    50                  55                  60
Asp Glu Ala Phe Asp Ala Phe Tyr Asp Ala Leu Arg Asp Thr Gly His
65                  70                  75                  80
Asn Asp Leu Ala Asp Val Leu Met Pro Leu Ser Arg Pro Xaa Xaa Xaa
                85                  90                  95
Asn Pro Val Pro Met Glu Cys Pro Met Ser Pro Ser His Arg Arg
                100                 105                 110
Ser Arg Ala Leu Ser Pro Pro Xaa Tyr Ala Ser Pro Thr Arg Val His
                115                 120                 125
Arg Asp Ser Ile Ser Ser Val Ser Ser Phe Thr Ser Thr Tyr Gln Asp
                130                 135                 140
Val Tyr Ser Arg Ala Arg Ser Ser Ser Arg Ser Arg Pro Leu Gln
145                 150                 155                 160
Ser Ser Asp Arg His Asn Tyr Met Ser Ala Ala Thr Ser Phe Pro Ser
```

-continued

```
                165                 170                 175
Gln Pro Xaa Ser Ala Asn Ser Ser Phe Thr Gly Cys Ala Ser Leu Gly
            180                 185                 190
Tyr Ser Ser Ser Arg Asn Arg Ser Phe Ser Lys Thr Ser Ala Gln Ser
        195                 200                 205
Gln Tyr Ile Phe His Glu Glu Asp Met Asn Tyr Val Asp Ala Pro Thr
    210                 215                 220
Ile His Arg Val Phe Asp Glu Lys Thr Met Tyr Arg Asn Phe Ser Ser
225                 230                 235                 240
Pro Arg Gly Leu Cys Leu Ile Ile Asn Asn Glu His Phe Glu Gln Met
                245                 250                 255
Pro Thr Arg Asn Gly Thr Lys Ala Asp Lys Asp Asn Leu Thr Asn Ile
            260                 265                 270
Phe Arg Cys Met Gly Tyr Thr Val Ile Cys Lys Asp Asn Leu Thr Gly
        275                 280                 285
Arg Glu Met Leu Ser Thr Ile Arg Ser Phe Gly Arg Asn Asp Met His
    290                 295                 300
Gly Asp Ser Ala Ile Leu Val Ile Leu Ser His Gly Glu Xaa Asn Val
305                 310                 315                 320
Ile Ile Gly Val Asp Asp Val Ser Val Asn Val His Glu Ile Tyr Asp
                325                 330                 335
Leu Leu Asn Ala Ala Asn Ala Pro Arg Leu Ala Asn Lys Pro Lys Leu
            340                 345                 350
Val Phe Val Gln Ala Cys Arg Gly Glu Arg Arg Asp Asn Gly Phe Pro
        355                 360                 365
Val Leu Asp Ser Val Asp Gly Val Pro Ser Leu Ile Arg Arg Gly Trp
    370                 375                 380
Asp Asn Arg Asp Gly Pro Leu Phe Asn Phe Leu Gly Cys Val Arg Pro
385                 390                 395                 400
Gln Val Gln Gln Val Trp Arg Lys Lys Pro Ser Gln Ala Asp Met Leu
                405                 410                 415
Ile Ala Tyr Ala Thr Thr Ala Gln Tyr Val Ser Trp Arg Asn Ser Ala
            420                 425                 430
Arg Gly Ser Trp Phe Ile Gln Ala Val Cys Glu Val Phe Ser Leu His
        435                 440                 445
Ala Lys Asp Met Asp Val Val Glu Leu Leu Thr Glu Val Asn Lys Lys
    450                 455                 460
Val Ala Cys Gly Phe Gln Thr Ser Gln Gly Ser Asn Ile Leu Lys Gln
465                 470                 475                 480
Met Pro Glu Leu Thr Ser Arg Leu Leu Lys Lys Phe Tyr Phe Trp Pro
                485                 490                 495
Glu Asp Arg Gly Arg Asn Ser Ala Val
                500                 505
```

(2) INFORMATION FOR SEQ ID NO: 21:

(i) SEQUENCE CHARACTERISTICS:
        (A) LENGTH: 479 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO: 21:

Thr Val Ser Ile Ser Leu Ile Ile Ala Arg Gln Val Leu Asn Ser Asp

|   |   |   |   |   |   |   |   |   |   |
|---|---|---|---|---|---|---|---|---|---|
| 1 |   |   |   | 5 |   |   |   |   | 10 |   |   |   |   | 15 |

Asn Gly Asp Met Ile Asn Ser Cys Gly Thr Val Arg Glu Lys Arg Arg
                    20                      25                      30

Glu Ile Val Lys Ala Val Gln Arg Arg Gly Asp Val Ala Phe Asp Ala
                35                      40                      45

Phe Tyr Asp Ala Leu Arg Ser Thr Gly His Glu Gly Leu Ala Glu Val
            50                      55                      60

Leu Glu Pro Leu Ala Arg Ser Val Asp Ser Asn Ala Val Glu Phe Glu
65                      70                      75                      80

Cys Pro Met Ser Pro Ala Ser His Arg Arg Ser Arg Ala Leu Ser Pro
                    85                      90                      95

Ala Gly Tyr Thr Ser Pro Thr Arg Val His Arg Asp Ser Val Ser Ser
                100                     105                     110

Val Ser Ser Phe Thr Ser Tyr Gln Asp Ile Tyr Ser Arg Ser Thr Ser
            115                     120                     125

Ser Ser Ser Arg Pro Leu His Thr Ser Asp Arg His Asn Tyr Val Ser
    130                     135                     140

Pro Ser Asn Ser Phe Gln Ser Gln Pro Ala Ser Ala Asn Ser Ser Phe
145                     150                     155                     160

Thr Gly Ser Ser Ser Leu Gly Tyr Ser Ser Arg Thr Arg Ser Tyr
                    165                     170                     175

Ser Lys Ala Ser Ala His Ser Gln Tyr Ile His Glu Glu Asp Met Asn
                180                     185                     190

Tyr Val Asp Ala Pro Thr Ile His Arg Val Phe Asp Glu Lys Thr Met
            195                     200                     205

Tyr Arg Asn Phe Ser Thr Pro Arg Gly Leu Cys Leu Ile Ile Asn Asn
    210                     215                     220

Glu His Phe Glu Gln Met Pro Thr Arg Asn Gly Thr Lys Pro Asp Lys
225                     230                     235                     240

Asp Asn Ile Ser Asn Leu Phe Arg Cys Met Gly Tyr Ile Val His Cys
                    245                     250                     255

Lys Asp Asn Leu Thr Gly Arg Gly Met Met Leu Thr Ile Arg Asp Phe
                260                     265                     270

Ala Lys Asn Glu Thr His Gly Asp Ser Ala Ile Leu Val Ile Leu Ser
            275                     280                     285

His Gly Glu Glu Asn Val Ile Ile Gly Val Asp Asp Val Ser Val Asn
    290                     295                     300

Val His Glu Ile Tyr Xaa Leu Leu Asn Ala Ala Asn Ala Pro Arg Leu
305                     310                     315                     320

Ala Asn Lys Pro Lys Leu Val Phe Val Gln Ala Cys Arg Gly Glu Arg
                    325                     330                     335

Arg Asp Val Gly Phe Pro Val Leu Asp Ser Val Asp Gly Val Pro Ala
                340                     345                     350

Leu Ile Arg Arg Gly Trp Asp Lys Gly Asp Gly Pro Leu Phe Asn Phe
            355                     360                     365

Leu Gly Cys Val Arg Pro Gln Ala Gln Val Trp Arg Lys Lys Pro
    370                     375                     380

Ser Gln Ala Asp Ile Leu Ile Ala Tyr Ala Thr Thr Ala Gln Tyr Val
385                     390                     395                     400

Ser Trp Arg Asn Ser Ala Arg Gly Ser Trp Phe Ile Gln Ala Val Cys
                    405                     410                     415

Glu Val Phe Ser Leu His Ala Lys Asp Met Asp Val Val Glu Leu Leu
                420                     425                     430

```
Thr Glu Val Asn Lys Lys Val Ala Cys Gly Phe Gln Thr Ser Gln Gly
        435                 440                 445

Ala Asn Ile Leu Lys Gln Met Pro Glu Leu Thr Ser Arg Leu Leu Lys
        450                 455                 460

Lys Phe Tyr Phe Trp Pro Glu Asp Arg Asn Arg Ser Ser Ala Val
465                 470                 475
```

(2) INFORMATION FOR SEQ ID NO: 22:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

```
ATTGGCGATC CTCTCGA                                              17
```

(2) INFORMATION FOR SEQ ID NO: 23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

```
TCATCGACTT TTAGATGACT AGAGAACATC                                30
```

(2) INFORMATION FOR SEQ ID NO: 24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

```
GTTGCACTGC TTTCACGATC TCCCGTCTCT                                30
```

(2) INFORMATION FOR SEQ ID NO: 25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

```
GTTTAATTAC CCAAGTTTGA G                                         21
```

(2) INFORMATION FOR SEQ ID NO: 26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear -continued (ii) MOLECULE TYPE: DNA (xi) SEQUENCE DESCRIPTION: SEQ ID NO: 26:

GGTTTTAACC AGTTACTCAA G                                    21

(2) INFORMATION FOR SEQ ID NO: 27:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 27:

CCGGTGACAT TGGACACTC                                       19

(2) INFORMATION FOR SEQ ID NO: 28:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 28:

ACTATTCAAC ACTTG                                           15